(12) United States Patent
Alitalo et al.

(10) Patent No.: US 9,260,526 B2
(45) Date of Patent: Feb. 16, 2016

(54) FLT4 (VEGFR-3) AS A TARGET FOR TUMOR IMAGING AND ANTI-TUMOR THERAPY

(71) Applicant: VEGENICS PTY LIMITED, South Yarra (AU)

(72) Inventors: Kari Alitalo, Helsinki (FI); Taija Makinen, Helsinki (FI)

(73) Assignee: VEGENICS PTY LIMITED, South Yarra (AU)

( * ) Notice: Subject to any disclaimer, the term of this patent is extended or adjusted under 35 U.S.C. 154(b) by 0 days.

(21) Appl. No.: 14/543,277

(22) Filed: Nov. 17, 2014

(65) Prior Publication Data

US 2015/0141622 A1    May 21, 2015

Related U.S. Application Data

(60) Division of application No. 11/327,075, filed on Jan. 6, 2006, now Pat. No. 8,940,695, which is a continuation of application No. 09/765,534, filed on Jan. 19, 2001, now Pat. No. 7,034,105.

(51) Int. Cl.
| | |
|---|---|
| C12N 15/62 | (2006.01) |
| C12N 15/63 | (2006.01) |
| C07H 21/00 | (2006.01) |
| C07K 16/28 | (2006.01) |
| A61K 9/00 | (2006.01) |
| C07K 14/71 | (2006.01) |
| C12N 9/12 | (2006.01) |
| A61K 38/00 | (2006.01) |
| A61K 48/00 | (2006.01) |
| A61K 39/00 | (2006.01) |

(52) U.S. Cl.
CPC .............. *C07K 16/2863* (2013.01); *A61K 9/00* (2013.01); *C07K 14/71* (2013.01); *C12N 9/1205* (2013.01); *A61K 38/00* (2013.01); *A61K 48/00* (2013.01); *A61K 2039/505* (2013.01); *C07H 21/00* (2013.01); *C07K 2316/96* (2013.01); *C07K 2317/21* (2013.01); *C07K 2317/24* (2013.01); *C07K 2319/00* (2013.01); *C07K 2319/30* (2013.01); *C12N 15/62* (2013.01); *C12N 15/63* (2013.01)

(58) Field of Classification Search
None
See application file for complete search history.

(56) References Cited

U.S. PATENT DOCUMENTS

| | | |
|---|---|---|
| 4,543,439 A | 9/1985 | Frackelton, Jr. et al. |
| 4,652,639 A | 3/1987 | Stabinsky |
| 4,933,294 A | 6/1990 | Waterfield et al. |
| 5,183,884 A | 2/1993 | Kraus et al. |
| 5,185,438 A | 2/1993 | Lemischka |
| 5,198,359 A | 3/1993 | Taniguchi et al. |
| 5,231,001 A | 7/1993 | Kaplan et al. |
| 5,256,766 A | 10/1993 | Coughlin |
| 5,270,458 A | 12/1993 | Lemischka |
| 5,283,354 A | 2/1994 | Lemischka |
| 5,367,057 A | 11/1994 | Lemischka |
| 5,635,177 A | 6/1997 | Bennett et al. |
| 5,643,759 A | 7/1997 | Pfreundschuh et al. |
| 5,693,762 A | 12/1997 | Queen et al. |
| 5,700,822 A | 12/1997 | Hirth et al. |
| 5,712,395 A | 1/1998 | App et al. |
| 5,747,651 A | 5/1998 | Lemischka |
| 5,750,078 A | 5/1998 | Shitara et al. |
| 5,763,441 A | 6/1998 | App et al. |
| 5,763,733 A | 6/1998 | Whitlow et al. |
| 5,776,427 A | 7/1998 | Thorpe et al. |
| 5,776,755 A | 7/1998 | Alitalo et al. |
| 5,798,097 A | 8/1998 | McKenzie et al. |
| 5,807,548 A | 9/1998 | Shitara et al. |
| 5,932,540 A | 8/1999 | Hu et al. |
| 5,935,820 A | 8/1999 | Hu et al. |
| 5,952,199 A | 9/1999 | Davis-Smyth et al. |
| 6,011,003 A | 1/2000 | Charnock-Jones et al. |
| 6,040,157 A | 3/2000 | Hu et al. |
| 6,100,071 A | 8/2000 | Davis-Smyth et al. |
| 6,107,046 A | 8/2000 | Alitalo et al. |
| 6,130,071 A | 10/2000 | Alitalo et al. |
| 6,221,839 B1 | 4/2001 | Alitalo et al. |
| 6,235,713 B1 | 5/2001 | Achen et al. |
| 6,245,530 B1 | 6/2001 | Alitalo et al. |
| 6,331,302 B1 | 12/2001 | Bennett et al. |
| 6,361,946 B1 | 3/2002 | Alitalo et al. |
| 6,383,484 B1 | 5/2002 | Achen et al. |
| 6,383,486 B1 | 5/2002 | Davis-Smyth et al. |
| 6,403,088 B1 | 6/2002 | Alitalo et al. |
| 6,451,764 B1 | 9/2002 | Lee et al. |

(Continued)

FOREIGN PATENT DOCUMENTS

| | | |
|---|---|---|
| EP | 0 325 224 A2 | 7/1989 |
| EP | 0 935 001 | 8/1999 |

(Continued)

OTHER PUBLICATIONS

"Angiogenesis Inhibitors in Cancer Research," Cancer Trials, at cancertrials.nci.nih.gov/news/angio/fsangio/fsangio.html (visited Jan. 24, 2001).
"Angiogenesis Inhibitors in Clinical Trials," Cancer Trials, at cancertrials.nci.nih.gove/news/angio/table.html (visited Jan. 24, 2001).
"Angiogenesis Inhibitors in Clinical Trials," Cancer Trials, at cancertrials.nci.nih.gove/news/angio/table.html (visited Sep. 25, 2001).
"Angiogenesis Inhibitors in Clinical Trials: Expanded Trial Information," Cancer Trials, at cancertrials.nci.nih.gove/news/angio/table.html (visited Sep. 25, 2001).

(Continued)

*Primary Examiner* — Jeffrey Stucker
*Assistant Examiner* — Stephen Gucker
(74) *Attorney, Agent, or Firm* — Marshall, Gerstein & Borun LLP

(57) ABSTRACT

The present invention provide purified Flt4 receptor tyrosine kinase polypeptides and fragments thereof, polynucleotides encoding such polypeptides, antibodies that specifically bind such polypeptides, and uses therefor.

33 Claims, 13 Drawing Sheets

(56) References Cited

U.S. PATENT DOCUMENTS

| | | | |
|---|---|---|---|
| 6,576,608 B1 | 6/2003 | Lee et al. |
| 6,608,182 B1 | 8/2003 | Rosen et al. |
| 6,645,933 B1 | 11/2003 | Alitalo et al. |
| 6,673,343 B2 | 1/2004 | Bennett et al. |
| 6,689,580 B1 | 2/2004 | Achen et al. |
| 6,730,658 B1 | 5/2004 | Alitalo et al. |
| 7,422,741 B2 | 9/2008 | Alitalo et al. |
| 7,829,091 B2 | 11/2010 | Alitalo |
| 7,855,178 B2 | 12/2010 | Alitalo et al. |
| 8,444,957 B2 | 5/2013 | Alitalo et al. |
| 2001/0038842 A1 | 11/2001 | Achen et al. |
| 2002/0065218 A1 | 5/2002 | Achen et al. |
| 2002/0102260 A1 | 8/2002 | Achen et al. |
| 2002/0120123 A1 | 8/2002 | Rosen et al. |
| 2002/0123481 A1 | 9/2002 | Oliviero |
| 2002/0127222 A1 | 9/2002 | Achen et al. |
| 2002/0146420 A1 | 10/2002 | Bennett et al. |
| 2002/0151489 A1 | 10/2002 | Gravereaux et al. |
| 2002/0182683 A1 | 12/2002 | Hu et al. |
| 2003/0008357 A1 | 1/2003 | Hu et al. |
| 2003/0028007 A1 | 2/2003 | Hu et al. |
| 2003/0091567 A1 | 5/2003 | Alitalo et al. |
| 2003/0092604 A1 | 5/2003 | Davis-Smyth et al. |
| 2003/0125537 A1 | 7/2003 | Achen et al. |
| 2003/0166523 A1 | 9/2003 | Achen et al. |
| 2003/0166547 A1 | 9/2003 | Oliviero |
| 2003/0166873 A1 | 9/2003 | Lee et al. |
| 2003/0180294 A1 | 9/2003 | DeVries |
| 2003/0211101 A1 | 11/2003 | Wise et al. |
| 2003/0211988 A1 | 11/2003 | Epstein |
| 2003/0215921 A1 | 11/2003 | Coleman |
| 2004/0037820 A1 | 2/2004 | Alitalo et al. |
| 2006/0177901 A1 | 8/2006 | Alitalo et al. |

FOREIGN PATENT DOCUMENTS

| | | |
|---|---|---|
| WO | WO-90/14425 | 11/1990 |
| WO | WO-92/14748 | 3/1992 |
| WO | WO-92/13867 | 8/1992 |
| WO | WO-93/14124 | 7/1993 |
| WO | WO-93/15201 | 8/1993 |
| WO | WO-94/10202 | 5/1994 |
| WO | WO-95/24473 | 9/1995 |
| WO | WO-95/33772 | 12/1995 |
| WO | WO-96/39515 | 12/1996 |
| WO | WO-97/05250 A2 | 2/1997 |
| WO | WO-97/09427 | 3/1997 |
| WO | WO-97/12972 | 4/1997 |
| WO | WO-98/02543 | 1/1998 |
| WO | WO-98/07832 | 2/1998 |
| WO | WO-98/33917 | 8/1998 |
| WO | WO-99/33485 | 8/1999 |
| WO | WO-00/45835 | 8/2000 |
| WO | WO-00/75319 A1 | 12/2000 |
| WO | WO-2004/009773 | 1/2004 |

OTHER PUBLICATIONS

Achen, M. G., et al., "Localization of Vascular Endothelial Growth Factor-D in Malignant Melanoma Suggests a Role in Tumour Angiogenesis" J. Pathol. 193(2): 147-54 (2001).
Achen, M.G. et al., "Monoclonal antibodies to vascular endothelial growth factor-D block its interactions with both VEGF receptor-2 and VEGF receptor-3," Eur. J. Biochem, 267(9):2505-15 (May 2000).
Achen, M.G. et al., "Vascular endothelial growth factor D (VEGF-F) is a ligand for the tyrosine kinases VEGF receptor 2 (Flk1) and VEGF receptor 3 (Flt4)," Proc. Natl. Acad. Sci., USA, 95(2):548-553 (Jan. 1998).
Akagi, K., et al., "Vascular endothelial growth factor-C (VEGF-C) expression in colorectal cancer tissues," Br. J. Cancer, 83(7):887-91 (Oct. 2000).
Alon et al., Vascular endothelial growth factor acts as a survival factor for newly formed retinal vessels and has implications for retinopathy of prematurity, Nat. Med., 1(10):1024-8 (1995).
Andersson et al., "Structural and Functional Markers During Induced Differentiation in Human Leukemia Cell Lines," In R. F. Revoltella (ed.), Expression of Differentiated Functions in Cancer Cells. 239 245, Raven Press, New York (1982).
Andre, T., et al., "Vegf, Vegf-B, Vegf-C and their receptors KDR, FLT-1 and FL the neoplastic progression of human colonic mucosa," Int. J. Cancer, 86(2):174-81 (Apr. 15, 2000).
Aprelikova et al., "FLT4, A Novel Class III Receptor Tyrosine Kinase in Chromosome 5q33-qter," Cancer Research, 52(3):746-748 (Feb. 1, 1992).
Aujame, L. et al., "High affinity human antibodies by phage display," Human Antibodies, 8(4):155-168 (1997).
Banerji, S. et al., "LYVE 1, a new homologue of the CD44 glycoprotein, is a lymph specific receptor for hyaluronan," J Cell Biol. 144(4):789 801 (1999).
Beckstead, J.H. et al., "Evidence for the Origin of Kaposi's Sarcoma From Lymphatic Endothelium," Am. J. Pathol., 119(2):294-300 (May 1985).
Bell et al., Human epidermal growth factor precursor: cDNA sequence, expression in vitro and gene organization, Nucleic Acids Res., 14(21):8427-46 (1986).
Benjamin et al., Selective ablation of immature blood vessels in established human tumors follows vascular endothelial growth factor withdrawal, J. Clin. Invest., 103(2):159-65 (1999).
Benz, C. C. et al., "Estrogen dependent, tamoxifen resistant tumorigenic growth of MCF 7 cells transfected with HER2/neu," Breast Cancer Res Treat. 24(2):85 95 (1993).
Berridge et al., "Cell-Lineage Antigens of the Stem Cell-Megakaryocyte-Platelet Linkage are Associated with the Platelet IIb-IIIa Glycoprotein Complex," Blood, 66(1):76 85 (Jul. 1985).
Bolen, J.B., "Nonreceptor Tyrosine Protein Kinases," Oncogene, 8:2025-2031 (1993).
Bolhuis, R.L. et al., "T cell targeting in cancer therapy," Cancer Immunology Immunotherapy, 34(1):1-8 (1991).
Borg et al., "Biochemical Characterization of Two Isoforms of FLT4, a VEGF Receptor-Related Tyrosin Kinase," Oncogene, 10:973-984 (1995).
Brown, L.F. et al., "Expression of Vascular Permeability Factor (Vascular Endothelial Growth Factor) and Its Receptors in Breast Cancer," Human Pathology, 26(1):86-91 (Jan. 1995).
Brüggemann, M. et al., "Production of human antibody repertoires in transgenic mice," Curr. Opin. Biotechnol., 8:455-458 (1997).
Brüggemann, M. et al., "Strategies for expressing human antibody repertoires in transgenic mice," Immunol. Today, 17(8):391-397 (Aug. 1996).
Bunone, G., et al., "Expression of Angiogenesis Stimulators and Inhibitors in Human Thyroid Tumors and Correlation with Clinical Pathological Features," Am. J. Pathol, 155(6):1967-76 (Dec. 1999).
Byrne, C. et al., "Programming Gene Expression in Developing Epidermis," Development, 120(9):2369 83 (1994).
Cantley et al., "Oncogenes and Signal Transduction," Cell, 64:281 302 (Jan. 25, 1991).
Cao, Y., et al., "Vascular Endothelial Growth Factor C Induces Angiogenesis in Vivo," Proc. Natl. Acad. Sci. USA, 95:14389-94 (Nov. 1998).
Carmeliet et al., Abnormal blood vessel development and lethality in embryos lacking a single VEGF allele, Nature, 380(6573):435-9 (1996).
Carter, P. et al., "Toward the Production of Bispecific Antibody Fragments for Clinical Applications," Journal of Hematotherapy, 4:463-470 (1995).
Catoretti et al., "Monoclonal Antibodies Against Recombinant Parts of the Ki-67 Antigen (MIB 1 and MIB 3) Detect Proliferating Cells in Microwave-Processed Formalin-Fixed Paraffin Section," J. of Pathol., 168:357-363 (1992).
Cheng & Flanagan, "Identification and Cloning of ELF-1, a Developmentally Expressed Ligand for the Mek4 and Sek Receptor Tyrosine Kinases," Cell, 79:157-168 (Oct. 7, 1994).
Cole et al., "The EBV-Hybridoma Technique and Its Application to Human Lung Cancer," Monoclonal Antibodies and Cancer Therapy, Alan R Liss, Inc., pp. 77 96 (1985).

(56) References Cited

OTHER PUBLICATIONS

Collins et al., "Continuous Growth and Differentiation of Human Myeloid Leukaemic Cells in Suspension Culture," Nature, 270:347 349 (1977).
Corson et al., Fibrillin binds calcium and is coded by cDNAs that reveal a multidomain structure and alternatively spliced exons at the 5' end, Genomics, 17:476-84 (1993).
De Gast, G.C. et al., "Clinical perspectives of bispecific antibodies in cancer," Cancer Immunol Immunother, 45:121-123 (1997).
De Vries et al., "The fms-Like Tyrosine Kinase, a Receptor for Vascular Endothelial Growth Factor," Science, 255:989-991 (Feb. 21, 1992).
De Waal, R. et al., "Technical Advance: Lack of Lymphangiogenesis in Human Primary Cutaneous Melanoma," American Journal of Pathology, 150(6):1951-1957 (Jun. 1997).
Devereux et al., "A Comprehensive Set of Sequence Analysis Programs for the VAX," Nucleic Acids Res., 12(1):387 395 (1984).
Dias, et al., "Vascular endothelial growth factor (VEGF)-C signaling through FLt-4 (VEGFR-3) mediates leukemic cell proliferation, survival, and resistance to chemotherapy," Blood, 99:2179-2184 (2002).
Dictor, M. et al., "Lymphaticovenous Differentiation in Kaposi's Sarcoma: Cellular Phenotypes by Stage," American Journal of Pathology, 130(2):411-417 (Feb. 1988).
Dignam et al., "Balbiani Ring 3 in Chironomus Tentans Encodes a 185 kDa Secretory Protein Which Is Synthesized Throughout the Fourth Larval Instar," Gene, 88:133-40 (1990).
Dumont, D. J. et al., "Cardiovascular Failure in Mouse Embryos Deficient in VEGF Receptor 3," Science, 282(5390):946 49 (1998).
Edgell et al., "Permanent Cell Line Expressing Human Factor VIII-Related Antigen Established by Hybridization," Proc. Nat'l. Acad. Sci. USA, 50:3734 3737 (Jun. 1983).
Egeblad, M. and Jaattela, M. "Cell death induced by TNF or serum starvation is independent of ErbB receptor signaling in MCF 7 breast carcinoma cells," Int J Cancer, 86(5):617 25 (2000).
Eggert, A., et al., "High-Level Expression of Angiogenic Factors Is Associated with Advanced Tumor Stage in Human Neuroblastomas," Clin. Cancer Res., 6(5):1900-8 (May 2000).
Eichmann et al., "Molecular cloning of Quek 1 and 2, two quail vascular endothelial growth factor (VEGF) receptor-like molecules," Gene, 174(1):3-8 (1996).
Enholm et al., Adenoviral expression of vascular endothelial growth factor-C induces lymphangiogenesis in the skin, Circ. Res., 88(6):623-9 (2001).
Enholm, B. et al., "Vascular Endothelial Growth Factor-C, a Growth Factor for Lymphatic and Blood Vascular Endothelial Cells," TCM, 8(7):292-297 (1998).
Evans et al., Mapping of primary congenital lymphedema to the 5q35.3 region, Am. J. Hum. Genet., 64:547-55 (1999).
Fanger, M.W. et al., "Bispecific Antibodies," Critical Reviews in Immunology, 12(3,4):101-124 (1992).
Fellmer, P.T., et al., "Vascular endothelial growth factor-C gene expression in papillary and follicular thyroid carcinomas," Surgery, 126(6):1056-61 (Dec. 1999).
Fernandez-Botran, R., "Soluble Cytokine Receptors: Novel Immunotherapeutic Agents," Exp. Opin. Invest. Drugs, 9:497-514 (2000).
Ferrara et al., Heterozygous embryonic lethality induced by targeted inactivation of the VEGF gene, Nature, 380(6573):439-42 (1996).
Ferrara, N. et al., "Molecular and Biological Properties of Vascular Endothelial Growth Factor," J Mol Med., 77(7):527 43. (1999).
Ferrara, N. et al., "The Biology of Vascular Endothelial Growth Factor," Endocrine Reviews, 18(1):4-25 (1997).
Ferrell et al., Hereditary lymphedema: evidence for linkage and genetic heterogeneity, Hum. Mol. Gen., 7(13):2073-8 (1998).
Fielder W., et al., "Expression of FLT4 and its ligand VEGF-C in Acute Myeloid Leukemia," Leukemia, 8:1234-7 (Aug. 1997) (Abstract).
Finnerty et al., "Molecular Cloning g of Murine FLT and FLT4," Oncogene, 8(11):2293-2298 (1993).
Flanagan & Leder, "The kit Ligand: A Cell Surface Molecule Altered in Steel Mutant Fibroblasts," Cell, 63:185-194 (Oct. 5, 1990).
Folkman et al., "Long-term culture of capillary endothelial cells," Proc. Nat'l Acad. Sci., USA, 76(10):5217-5221 (Oct. 1979).
Folpe, A.L., et al., "Vascular Endothelial Growth Factor Receptor-3 (VEGFR-3): A Marker of Vascular Tumors with Presumed Lymphatic Differentiation, Including Kaposi's Sarcoma, Kaposiform and Dabska-Type Hemangioendotheliomas, and a Subset of Angiosarcomas," Mod. Pathol, 13(2):180-185 (2000).
Fong et al., Role of the Flt-1 receptor tyrosine kinase in regulating the assembly of vascular endothelium, Nature, 376(6535):66-70 (1995).
Foote, J. et al., "Antibody Framework Residues Affecting the Conformation of the Hypervariable Loops," J. Mol. Biol., 224:487-499 (1992).
Fortkamp et al., "Cloning and Expression in *Escherichia coli* of a Synthetic DNA for Hirudin, the Blood Coagulation Inhibitor in the Leech," DNA, 5(6):511-517 (1986).
Fournier et al., "Interaction with the Phosphotyrosine Binding Domain/Phosphotyrosine Interacting Domain of SHC Is Required for the Transforming Activity of the FLT4/VEGFR3 Receptor Tyrosine Kinase," J. Biological Chemistry, 271(22):12956-12963 (1996).
Fournier et al., "Mutation at Tyrosine Residue 1337 Abrogates Ligand-Dependent Transforming Capacity of the FLT4 Receptor," Oncogene, 11:921-931 (1995).
Gahmberg et al., "Membrane Glycolysation During Cell Differentiation," In L. C. Andersson, et al. (ed.), Gene Expression During Normal and Malignant Differentiation, 107 123, Academic Press, London (1985).
Galland et al., "Chromosomal Localization of FLT4, a Novel Receptor-Type Tyrosine Kinase Gene," Genomics, 13:475-478 (1992).
Galland et al., "The FLT4 Gene Encodes a Transmembrane Tyrosine Kinase Related to the Vascular Endothelial Growth Factor Receptor," Oncogene, 8(11):1233-1240 (1993).
Gasparini, G. et al., "Clinical Importance of the Determination of Tumor Angiogenesis in Breast Carcinoma: Much More Than a New Prognostic Tool," Journal of Clinical Oncology, 13(3):765-782 (Mar. 1995).
GenBank Accession No. AF014827, Rattus norvegicus vascular endothelial growth factor D (VEGF D) mRNA, deposited by Yamada, Y.
GenBank Accession No. AJ000185, Homo Sapiens mRNA for vascular endothelial growth factor-D, deposited by Achen, M.G.
GenBank Accession No. CCY15837, Coturnix coturnix mRNA for vascular endothelial growth factor C, deposited by Eichmann, A.
GenBank Accession No. D89628, Mus musculus mRNA for vascular endothelial growth factor D, deposited by Yamada, Y.
GenBank Accession No. MMU73620, Mus musculus VEGFC mRNA, complete cds., deposited by Kukke, E.
Genbank Accession No. P35916, Galland et al., "Vascular Endothelial Frowth Factor Receptor 3 Precursor," (Oct. 1, 1996).
Genbank Accession X51602 Human flt mRNA for receptor-related tyrosine kinase, deposited by Shibuya, M.
Genbank Accession X60280 plasmid pLTRpoly, deposited by Maekelae et al.
Genbank Accession X68203 H. sapiens mRNA for FLT4, Class III receptor tyrosine kinase, deposited by Aprelikova, O.
Genbank Accession X83287 C. coturnix Quek2 mRNA for vascular endothelial growth factor receptor, deposited by Eichmann, et al.
Gerber et al., Vascular endothelial growth factor induces expression of the antiapoptotic proteins Bcl-2 and A1 in vascular endothelial cells, J. Biol. Chem., 273(21):13313-6 (1998).
Gerber et al., VEGF is required for growth and survival in neonatal mice, Development, 126(6):1149-59 (1999).
Greenberg et al., "Characterization of a New Megakaryocyte Cell Line: The Dami Cell," Blood, 72(6):1968 1977 (Dec. 1988).
Gunningham, S.P., et al., "The Short Form of the Alternatively Spliced flt-4 but not Its Ligand Vascular Endothelial Growth Factor C Is Related to Lymph Node Metastasis in Human Breast Cancers," Clin. Cancer Res., 6(11):4278-86 (Nov. 2000).
Harlow et al., Antibodies: A Laboratory Manual, pp. 7-25, 72-137, 141-157, 287 & 321-358 (1988).

(56) References Cited

OTHER PUBLICATIONS

Hatva et al., "Expression of Endothelial Cell-Specific Receptor Tyrosine Kinases and Growth Factors in Human Brain Tumors," Am. J. Pathol., 146:368-378 (1995).

Hatva, E., et al., "Vascular Growth Factors and Receptors in Capillary Hemangioblastomas and Hemangiopericytomas," Am. J. Pathol, 148(3):763-75 (Mar. 1996).

Heldin et al., "Platelet-Derived Growth Factor: Mechanism of Action and Possible in Vivo Function," Cell Regulation, 1:555 566 (Jul. 1990).

Hemmila et al., "Europium as a Label in Time-Resolved Immunofluorometric Assays," Annal. Biochem, 137:335-343 (1984).

Hewett, P.W. et al., "Coexpression of flt-1, flt-4 and KDR in Freshly Isolated and Cultured Human Endothelial Cells," Biochemical and Biophysical Research Communications, 221:697-702 (1996).

Hirai et al., "A Novel Putative Tyrosine Kinase Receptor Encoded by the eph Gene," Science, 238:1717 1720 (1987).

Hirai, M. et al., "Expression of Vascular Endothelial Growth Factors (VEGF-A/VEGF-1 and VEGF-C/VEGF-2) in Postmenopausal Uterine Endomatrial Carcinoma," Gynecol. Oncol. 80(2):181-8 (Feb. 2001).

Hoogenboom, H.R., "Designing and optimizing library selection strategies for generating high-affinity antibodies," TIBTECH, 15:62-70 (1997).

Hu, Jing-Shan, et al., "A Novel Regulatory Function of Proteolytically Cleaved VEGF-2 for Vascular Endothelial and Smooth Muscle Cells," The FASEB Journal, 11:498-504 (May 1997).

Huang et al., "The Hematopoietic Growth Factor KL is Encoded by the SI Locus and is the Ligand of the c-kit Receptor, the Gene Product of the W Locus," Cell, 63:225 33 (Oct. 5, 1990).

Hunter & Greenwood, "Preparation of Iodine-131 Labelled Human Growth Hormone of High Specific Activity," Nature, 194(4827):495-496 (May 5, 1962).

IMC-1C11, ImClone Systems Incorporated, at www.imclone.com/imc1c11.html (visited Sep. 25, 2001).

Irrthum, A. et al., "Congenital hereditary lymphedema caused by a mutation that inactivates VEGFR3 tyrosine kinase.," Am J Hum Genet. 67(2):295 301 (2000).

Jacquemier, J., et al., "Prognosis of Breast-Carcinoma Lymphagenesis Evaluated by Immunohistochemical Investigation of Vascular-Endothelial-Growth-Factor Receptor 3," Int. J. Cancer (Pred. Oncol.), 89:69-73 (2000).

Jeltsch, "Hyperplasia of Lymphatic Vessels in VEGF-C Transgenic Mice," Science, 276:1423-1425 (May 30, 1997).

Jones, A., et al., "Angiogenesis and lymphangiogenesis in stage 1 germ cell tumours of the testis," BJU International, 86:80-86 (2000).

Jones, P.T. et al., "Replacing the complementarity-determining regions in a human antibody with those from a mouse," Nature, 321:522-525 (May 1986).

Joukov et al., "A Novel Vascular Endothelial Growth Factor, VEGF-C, is a Ligand for the Flt4 (VEGFR-3) and KDR (VEGFR-2) Receptor Tyrosine Kinases," EMBO J., 15(2):290-298 (Jan. 15, 1996).

Joukov, V. et al., "A Recombinant Mutant Vascular Endothelial Growth Factor c That Has Lost Vascular Endothelial Growth Factor Receptor 2 Binding, Activation, and Vascular Permeability Activities," J Biol Chem., 273(12):6599 602 (1998).

Joukov, V. et al., "Proteolytic processing regulates receptor specificity and activity of VEGF-C," EMBO Journal, 16(13):3898-3911 (Jun. 1997).

Jussila, L. et al., "Lymphatic Endothelium and Kaposi's Sarcoma Spindle Cells Detected by Antibodies against the Vascular Endothelial Growth Factor Receptor-3," Cancer Res., 58:15991604 (Apr. 1998).

Kabashima, A. et al., "Overexpression of Vascular Endothelial Growth Factor C is Related to Lymphogenous Metasasis in Early Gastric Carcinoma," Oncology, 60(2): 146-50 (2001).

Kadambi, A. et al., "Vascular Endothelial Growth Factor (VEGF)-C Differentially Affects Tumor Vascular Function and Leukocyte Recruitment: Role of VEGF-Receptor 2 and Host VEGF-A," Cancer Res. 61(6): 2404-8 (Mar. 2001).

Kaipainen et al., "Expression of the FMS-Like Tyrosine Kinase 4 Gene Becomes Restricted to Lymphatic Endothelium During Development," Proc. Nat'l Acad. Sci., USA, 92:3566-3570 (Apr. 1995).

Kaipainen et al., "The Related FLT4, FLT1, and KDR Receptor Tyrosine Kinases Show Distinct Expression Patterns in Human Fetal Endothelial Cells," J. Exp. Med., 178:2077-2088 (Dec. 1993).

Karkkainen, et al., "Lymphatic endothelium: a new frontier of metastasis research," Nat. Cell. Biol. 4:E2-E5 (2002).

Karkkainen, et al., "Missense Mutations Interfere With VEGFR 3 Signalling in Primary Lymphoedema," Nat Genet., 25(2):153 9 (2000).

Karkkainen, M.J., et al., "Vascular Endothelial Growth Factor Receptors in the Regulation of Angiogenesis and Lymphangiogenesis," Oncogene, 19(49):5598-605 (Nov. 20, 2000).

Karpanen, T. et al., "Vascular Endothelial Growth Factor C Promotes Tumor Lymphangiogenesis and Intralymphatic Tumor Growth," Cancer Res. 61(5): 1786-90 (Mar. 2001).

Kendall et al., "Inhibition of Vascular Endothelial Cell Growth Factor Activity by an Endogenously Encoded Soluble Receptor," Proc. Natl. Acad. Sci. USA, 90:10705-10709 (1993).

Kerstens, H. et al., "A Novel In Situ Hybridization Signal Amplification Method Based on the Deposition of Biotinylated Tyramine," Journal Histochemistry and Cytochemistry, 43(4):347-352 (1995).

Kettleborough, C.A. et al., "Humanization of a mouse monoclonal antibody by CDR-grafting: the importance of framework residues on loop conformation," Protein Engineering, 4(7):773-783 (1991).

Kieffer et al., "Uncoupling in the Expression of Platelet GP IIb/IIIa in Human Endothelial Cells and K562 Cells: Absence of Immunologic Crossreactivity Between Platelet GP IIb and the Vitronectin Receptor Alpha Chain," Blood, 72(4):1209 1215 (Oct. 1988).

Kim, K.J. et al., "Inhibition of vascular endothelial growth factor-induced angiogenesis suppresses tumour growth in vivo," Nature, 362(6423):841-844 (Apr. 1993).

Koeffler et al., "Acute Myelogenous Leukemia: A Human Cell Line Responsive to Colony-Stimulating Activity," Science, 200:1153 1154 (1978).

Korhonen et al., "Enhanced Expression of the tie Receptor Tyrosine Kinase in Endothelial Cells During Neovascularization," Blood, 80(10):2548-2555 (Nov. 15, 1992).

Korhonen et al., "The Mouse Tie Receptor Tyrosine Kinase Gene: Expression During Embryonic Angiogenesis," Oncogene (England), 9(2):395-403 (Feb. 1994).

Korhonen, J. et al., "Endothelial Specific Gene Expression Directed by the Tie Gene Promoter in Vivo," Blood (5):1828 35 (1995).

Kozbor et al., "The Production of Monoclonal Antibodies From Human Lymphocytes," Immunology Today, 4(3):72-79 (1983).

Kubo, H., et al., "Involvement of vascular endothelial growth factor receptor-3 in maintenance of integrity of endothelial cell lining during tumor angiogenesis," Blood, 96(2):546-553 (Jul. 15, 2000).

Kukk et al., "VEGF-C Receptor Binding and Pattern of Expression with VEGFR-3 Suggests a Role in Lymphatic Vascular Development," Development, 122:3829-3837 (Dec. 1996).

Kurebayashi, J., et al., "Expression of Vascular Endothelial Growth Factor (VEGF) Family Members in Breast Cancer," Jpn. J. Cancer Res., 90(9):977-81 (Sep. 1999).

Köhler et al., "Continuous Cultures of Fused Cells Secreting Antibody of Predefined Specificity," Nature, 256:495 497 (Aug. 7, 1975).

Laitinen, M. et al., "Adenovirus mediated gene transfer to lower limb artery of patients with chronic critical leg ischemia," Hum Gene Ther, 9(10):1481 6 (1998).

Lauria, R. et al., The prognostic value of lymphatic and blood vessel invasion in operable breast cancer, Cancer, 76(10):1772 8 (1995).

Lee et al., "Vascular Endothelial Growth Factor-Related Protein: A Ligand and Specific Activator of the Tyrosine Kinase Receptor Flt4," Proc. Natl. Acad. Sci., USA, 93:1988-1992 (Mar. 1996).

Leu, A. J. et al., "Absence of Functional Lymphatics within a Murine Sarcoma: A Molecular and Functional Evaluation," Cancer Res, 60: 4324 7, (2000).

(56) References Cited

OTHER PUBLICATIONS

Lhotak et al., "Characterization of Elk, a Brain-Specific Receptor Tyrosine Kinase," Mol. Cell. Biol., 11:2496 2502 (May 1991).
Lindberg et al. "cDNA Cloning and Characterization of eck, an Epithelial Cell Receptor Protein-Tyrosine Kinase in the eph/elk Family of Protein Kinases," Mol. Cell. Biol., 10:6316 6324 (Dec. 1990).
Lovgren et al., "Time-Resolved Fluorometry in Immunoassay," In: Collins W.P. (Ed.) Alternative Immunoassays, John Wiley & Sons Ltd., pp. 203-217 (1985).
Lozzio et al., "Human Chronic Myelogenous Leukemia Cell-Line With Positive Philadelphia Chromosome," Blood, 45(3):321 334 (Mar. 1975).
Lyman et al., "Molecular Cloning of a Ligand for the flt3/flk-2 Tyrosine Kinase Receptor: A Proliferative Factor for Primitive Hematopoietic Cells," Cell, 75:1157-1167 (Dec. 17, 1993).
Lymboussaki, A. et al., "Expression of the Vascular Endothelial Growth Factor C Receptor VEGFR-3 in Lymphatic Endothelium of the Skin and in Vascular Tumors," American Journal of Pathology, 153(2):395-403 (Aug. 1998).
Makela et al., "Plasmid pLTRpoly: a Versatile High-Efficiency Mammalian Expression Vector," Gene, 118:293-294 (1992).
Makinen et al., Inhibition of lymphangiogenesis with resulting lymphedema in transgenic mice expressing soluble VEGF receptor-3, Nat. Med., 7(2):199-205 (2001).
Mandriota, S. J. et al., "Vascular Endothelial Growth Factor-C-Mediated Lymphangiogenesis Promotes Tumour Metastasis," EMBO J., 20(5): 672-82 (Feb. 15, 2001).
Marchio, S., et al., "Vascular Endothelial Growth Factor-C Stimulates the Migration and Proliferation of Kaposi's Sarcoma Cells," J. Biol. Chem., 274(39):27617-22 (Sep. 24, 1999).
Marconcini, L., et al., "c-fos-induced growth factor/vascular endothelial growth factor D induces angiogenesis in vivo and in vitro," Proc. Natl. Acad. Sci. USA, 96:9671-76 (Aug. 1999).
Martin et al., "HEL Cells: A New Human Erythroleukemia Cell Line With Spontaneous Induced Globin Expression," Science, 216:1233 1235 (1982).
Massague, The transforming growth factor-β family, Annu. Rev. Cell Biol., 6:597-641 (1990).
Matthews et al., "A Receptor Tyrosine Kinase cDNA Isolated From a Population of Enriched Primitive Hematopoietic Cells and Exhibiting Close Genetic Linkage to c-kit," Proc. Natl. Acad. Sci. USA, 88(20):9026 9030 (Oct. 1991).
Matthews et al., "A Receptor Tyrosine Kinase Specific to Hematopoietic Stem and Progenitor Cell-Enriched Populations," Cell, 65(7):1143-1152 (Jun. 28, 1991).
Mattila, et al., "VEGF-C induced lymphangiogenesis is associated with lymph node metastasis in orthotopic MCF-7 tumors," Int. J. Cancer. 98:946-951 (2002).
McCutchan et al., "Enhancement of the Infectivity of Simian Virus 40 Deoxyribonucleic Acid with Diethylaminoethyl-Dectran," J. Natl. Cancer Inst., 41:351 357 (1968).
Metzelaar et al., "CD63 Antigen," J. Biol. Chem., 266(5):3239-3245 (Feb. 15, 1991).
Millauer et al., High Affinity VEGF Binding and Developmental Expression Suggest Flk-1 as a Major Regulator of Vasculogenesis and Angiogenesis, Cell, 72:835-846 (Mar. 26, 1993).
Minowada et al., "Brief Communication: Rosette-Forming Human Lymphoid Cell Lines: Establishment and Evidence for Origin of Thymus-Derived Lymphocytes," J. Natl. Cancer Inst., 49:891 895 (1972).
Mollinedo et al., "Early and Selective Induction of Apoptosis in Human Leukemic Cells by the Alkyl-Lysophospholipid ET-18-OCH3," Biochem. & Biophys. Res. Comm., 192(2):603-609 (Apr. 30, 1993).
Moriyama, M., et al., "Immunohistochemical Study of Tumour Angiogenesis in Oral Squamous Cell Carcinoma," Oral Oncol., 33(5):369-74 (Sep. 1997).

Moroni et al., "EGF-R Antisense RNA Blocks Expression of the Epidermal Growth Factor Receptor and Suppresses the Transforming Phenotype of a Human Carcinoma Cell Line," J. Biol. Chem., 267(5):2714-2722 (Feb. 5, 1992).
Morrison, S.L. et al., "Genetically Engineered Antibody Molecules," Advances in Immunology, 44:65-92 (1989).
Mortimer, P. S., "The Pathophysiology of Lymphedema," Cancer, 83(12 Suppl American):2798 802 (1998).
Moshakis,V. et al., "Localization of human breast-carcinoma xenografts using antibodies to carcinoembryonic antigen," Br. J. Cancer, 43:575-581 (1981).
Mukkala et al., "The Synthesis and Use of Activated N-Benzyl Derivatives of Diethylenetriaminetetraacetic Acids: Alternative Reagents for Labeling of Antibodies with Metal Ions," Annal. Biochem, 176:319-325 (1989).
Mustonen et al., "Endothelial Receptor Tyrosine Kinases Involved in Angiogenesis," J. Cell Biology, 129(4):895-898 (1995).
Nathanson, S.D., et al., "Microvessels That Predict Axillary Lymph Node Metastases in Patients With Breast Cancer," Arch Surg, 135(5):586-93 (May 2000).
Neufeld et al., Vascular endothelial growth factor (VEGH) and its receptors, FASEB J., 13(1):9-22 (1999).
Nicosia, R.F., "What Is the Role of Vascular Endothelial Growth Factor-Related Molecules in Tumor Angiogenesis?" Am. J. Pathol, 153(1):11-6 (Jul. 1998).
Niki, T. et al., "Expression of Vascular Endothelial Growth Factor Receptor 3 in Blood and Lymphatic Vessels of Lung Adenocarcinoma," J. Pathol., 193(4): 450-7 (Apr. 2001).
Niki, T., et al., "Expression of Vascular Endothelial Growth Factors A, B, C, and D and Their Relationships to Lymph Node Status in Lung Adenocarcinoma," Clin. Cancer Res., 6(6):2431-9 (Jun. 2000).
Nowell et al., "Chromosome Studies in Preleukemic States: Myeloproliferative versus Cytopenic Disorders," Cancer, 42:2254 2260 (1978).
O'Reilly, M.S. et al., "Angiostatin: A Novel Angiogenesis Inhibitor That Mediates the Suppression of Metastases by a Lewis Lung Carcinoma," Cell, 79(2):315-328 (Oct. 1994).
O'Reilly, M.S. et al., "Endostatin: An Endogenous Inhibitor of Angiogenesis and Tumor Growth," Cell, 88(2):277-285 (Jan. 1997).
Oelrichs et al., "NYK/FLK-1: A Putative Receptor Protein Tyrosine Kinase Isolated From E10 Embryonic Neuroepithelium is Expressed in Endothelial Cells of the Developing Embryo," Oncogene, 8(1):11-18 (Jan. 1993).
Oh et al., "VEGF and VEGF-C: Specific Induction of Angiogenesis and Lymphangiogenesis in the Differentiated Avian Chorioallantoic Membrane," Developmental Biology, 188:96-109 (1997).
Ohta, Y., et al., "Increased Vascular Endothelial Growth Factor and Vascular Endothelial Growth Factor-C and Decreased NM23 Expression Associated with Microdissemination in the Lymph Nodes in Stage 1 Non-Small Cell Lung Cancer," J. Thorac Cardiovasc Surg, 119(4 Pt 1):804-13 (Apr. 2000).
Ohta, Y., et al., "VEGF and VEGF type C play an important role in angiogenesis and lymphangiogenesis in human malignant mesothelioma tumours," Br. J. Cancer, 81(1):54-61 (Sep. 1999).
Orlandini et al., Identification of a c-fos-induced gene that is related to the platelet-derived growth factor/vascular endothelial growth factor family, Proc. Natl. Acad. Sci. USA, 93(21):11675-80 (1996).
Padlan, E.A., "A Possible Procedure for Reducing the Immunogenicity of Antibody Variable Domains While Preserving Their Ligand-Binding Properties," Molecular Immunology, 28(4/5):489-498 (1991).
Pajusola et al., "FLT4 Receptor Tyrosine Kinase Contains Seven Immunoglobulin-Like Loops and is Expressed in Multiple Human Tissues and Cell Lines," Cancer Research, 52(20):5738-5743 (Oct. 15, 1992).
Pajusola et al., "Signalling Properties of FLT4, a Proteolytically Processed Receptor Tyrosine Kinase Related to Two VEGF Receptors," Oncogene, 9:3545-3555 (1994).
Pajusola et al., "Two Human FLT4 Receptor Tyrosine Kinase Isoforms With Distinct Carboxy Terminal Tails are Produced by Alternative Processing of Primary Transcripts," Oncogene, 8:2931-2937 (1993).

(56) References Cited

OTHER PUBLICATIONS

Pajusola, "Cloning and Characterization of a New Endothelial Receptor Tyrosine Kinase FLT4 and Two Novel VEGF-Like Growth Factors VEGF-B and VEGF-C," Molecular/Cancer Biology Laboratory and Department of Pathology, Haartman Institute and Department of Biosciences, Division of Genetics, University of Helsinki, Academic Dissertation, Helsinki 1996.
Parker, S. H., et al., "Identification of the sentinel node in patients with breast cancer, Radiol Clin North Am," 38(4):809 23 (2000).
Partanen et al., "A Novel Endothelial Cell Surface Receptor Tyrosine Kinase with Extracellular Epidermal Growth Factor Homology Domains," Mol. Cell. Biol., 12(4):1698-1707 (Apr. 1992).
Partanen et al., "Putative Tyrosine Kinases Expressed in K-562 Human Leukemia Cells," Proc. Nat'l Acad. Sci., USA, 87(22):8913-8917 (Nov. 1990).
Partanen, T.A., et al., "Lack of Lymphatic Vascular Specificity of Vascular Endothelial Growth Factor Receptor 3 in 185 Vascular Tumors," Cancer, 86(11): 2406-12 (Dec. 1, 1999).
Patent Cooperation Treaty Search Report for PCT/US 99/23525.
Paulsson, G. et al., "The Balbiani ring 3 gene in Chironomus tentans has a diverged repetitive structure split by many introns," J. Mol. Biol., 211:331-49 (1990).
Pepper, M. S., "Lymphangiogenesis and Tumor Metastasis: Myth or Reality?," Clinical Cancer Res., 7: 462-68 (Mar. 2001).
Perumov et al., "Influence of Antisense RNA's of Interleukin-1β and Interleukin-1 Receptor Antagonist on Interleukin-1 β Production," J. Cell. Biochem., Supplement, 16 pt B:285 (Abstract J216) (1992).
Peters et al., "Vascular Endothelial Growth Factor Receptor Expression During Embryogenesis and Tissue Repair Suggests a Role in Endothelial Differentiation and Blood Vessel Growth," Proc. Nat'l Acad. Sci., USA, 90:8915-8919 (Oct. 1993).
Peterson, C. and Legerski, R., "High-frequency Transformation of Human Repair-deficient Cell Lines by an Epstein-Barr Virus-based cDNA Expression Vector," Gene, 107: 279 84, (1991).
Pietersz et al., "Antibody Conjugates for the Treatment of Cancer," Immunological Reviews, 129:57-80 (1992).
Plückthun, A. et al., "New protein engineering approaches to multivalent and bispecific antibody fragments," Immunotechnology, 3:83-105 (1997).
Poncz et al., "Cloning and Characterization of Platelet Factor 4 cDNA Derived From a Human Erythroleukemic Cell Line," Blood, 69(1):219 223 (Jan. 1987).
Rader, C. et al., "Phage display of combinatorial antibody libraries," Curr. Opin. Biotech., 8:503-508 (1997).
Reedijk et al., "Tyr721 Regulates Specific Binding of the CSF-1 Receptor Kinase Insert to P1 3'-Kinase SH2 Domains: a Model for SH2-Mediated Receptor-Target Interactions," EMBO J., 11(4):1365 1372 (1992).
Relf, M. et al., "Expression of the Angiogenic Factors Vascular Endothelial Cell Growth Factor, Acidic and Basic Fibroblast Growth Factor, Tumor Growth Factor β-1, Platelet-derived Endothelial Cell Growth Factor, Placenta Growth Factor, and Pleiotrophin in Human Primary Breast Cancer and Its Relation to Angiogenesis," Cancer Research, 57:963-969 (Mar. 1997).
Renner, C. et al., "Tumor Therapy by Immune Recruitment with Bispecific Antibodies," Immunological Reviews, No. 145, pp. 179-209 (1995).
Riechmann, L. et al., "Reshaping human antibodies for therapy," Nature, 332(6162):323-327 (Mar. 1988).
Roeckl et al., Differential binding characteristics and cellular inhibition by soluble VEGF receptors 1 and 2, Exp. Cell Res., 241(1):161-70 (1998).
Roitt, M., "Essential Immunology," Blackwell Scientific Pub., Oxford, pp. 65-68 & 74 (1991).
Rosnet et al., "Isolation and Chromosomal Localization of a Novel FMS-Like Tyrosine Kinase Gene," Oncogene, 6(9):1641-1650 (1991).
Rosnet et al., "Murine Flt3, a Gene Encoding a Novel Tyrosine Kinase Receptor of the PDFR/CSF1R Family," Genomics, 9:380 385 (1991).

Saaristo, A., et al., "Vascular Endothelial Growth Factor-C and its Receptor VEGFR-3 in the Nasal Mucosa and in Nasopharyngeal Tumors," Am. J. Pathology, 157(1):7-14 (Jul. 2000).
Sabin, F.R., "The Lymphatic System in Human Embryos, with Consideration of the Morphology of the System as a Whole," Am. J. Anat., 9(1):43-91 (1909).
Salven, P. et al., "Vascular Endothelial Growth Factors VEGF-B and VEGF-C Are Expressed in Human Tumors," American J. Pathology, 153(1):103-108 (Jul. 1998).
Sambrook et al., Molecular Cloning: A Laboratory Manual, Cold Spring Harbor Laboratory Press, pp. 2.60-2.70, 4.21-4.32, 7.3-7.36 (1989).
Sato and Seiki, "Regulatory mechanism of 92 kDa type IV collagenase gene expression which is associated with invasiveness of tumor cells," Oncogene, 8:395-405 (1993).
Satoh et al., "Regional Localization of the Human c-ros-1 on 6q22 and flt on 13q12," Jpn. J. Cancer Res., 78:772 775 (1987).
Schlessinger, J., "Cell Signaling by Receptor Tyrosine Kinases," Cell, 103(2): 211-25 (Oct. 13, 2000).
Schneider et al., "A One-step Purification of Membrane Proteins Using a High Efficiency Immunomatrix," J. Biol. Chem., 257(18):10766-10769 (Sep. 25, 1982).
Schreiber et al., "Interaction of endothelial cell growth factor with heparin: Characterization by receptor and antibody recognition," Proc. Nat'l Acad. Sci., 82:6138-6142 (Sep. 1985).
Schwenk et al., "Cell Cycle Dependency of a T-Cell Marker on Lymphoblasts," Blut, 31:299 306 (1975).
Scott, P.A.E. et al., "Laboratory-Clinic Interface: Current approaches to targeting cancer using antiangiogenesis therapies," Cancer Treatment Reviews, 20:393-412 (1994).
Segal, D.M. et al., "Alternative Triggering Molecules and Single Chain Bispecific Antibodies," Journal of Hematotherapy, 4:377-382 (1995).
Segal, D.M. et al., "Targetting of Anti-Tumor Responses with Bispecific Antibodies," Immunobiology, 185(2-4):390-402 (Aug. 1992).
Sherr et al., "The c-fms Proto-Oncogene Product is Related to the Receptor for the Mononuclear Phagocyte Growth Factor, CSF-1," Cell, 41:665 676 (Jul. 1985).
Shi et al., "16-Kilodalton Heparin Binding (Fibroblast) Growth Factor Type One Appears in a Stable 40-Kilodalton Complex After Receptor-Dependent Internalization," J. Biol. Chem., 266(9):5774-5779 (Mar. 25, 1991).
Shibuya et al., "Nucleotide Sequence and Expression of a Novel Human Receptor-Type Tyrosine Kinase Gene (flt) Closely Related to the fms Family," Oncogene, 5:519 524 (1990).
Shibuya et al., Differential roles of vascular endothelial growth factor receptor-1 and receptor-2 in angiogenesis, J. Biochem. Mol. Biol., 39(5):469-78 (2006).
Shibuya, M., "Role of VEGF-FLT Receptor System in Normal and Tumor Angiogenesis," Advances in Cancer Research, 67:281-316 (1995).
Shushanov, S., et al., "VEGFc and VEGFR3 Expression in Human Thyroid Pathologies," Int. J. Cancer, 86:47-52 (2000).
Siemeister, et al., "Two independent mechanisms essential for tumor angiogenesis: inhibition of human melanoma xenograft growth by interfering with either the vascular endothelial growth factor receptor pathway or the Tie-2 pathway," Cancer Res. 59:3185-91 (1999).
Skobe, M. et al., "Induction of Tumor Lymphangiogenesis by VEGF-C Promotes Breast Cancer Metastasis," Nat. Med., 7(2): 192-8 (Feb. 2001).
Skobe, M., et al., "Vascular Endothelial Growth Factor-C (VEGF-C) and its Receptors KDR and flt-4 are Expressed in AIDS-Associated Kaposi's Sarcoma," J. Invest. Dermatology, 113:1047-1053 (1999).
Sowter, H.M., et al., "Expression and Localization of the Vascular Endothelial Growth Factor Family in Ovarian Epithelial Tumors," Lab. Invest., 77(6):607-14 (Dec. 1997).
Stacey et al., "SVpoly: A Versatile Mammalian Expression Vector," Nucl. Acids Res., 18(9):2829 (1990).
Stacker, S. A., "VEGF-D Promotes the Metastatic Spread of Tumor Cells Via the Lymphatics," Nat. Med., 7(2): 186-91 (Feb. 2001).

(56) References Cited

OTHER PUBLICATIONS

Staunton et al., "The Arrangement of the Immunoglobulin-Like Domains of ICAM-1 and the Binding Sites for LFA-1 and Rhinovirus," Cell, 61:243-254 (Apr. 20, 1990).
Stenman et al., "Human PDGFA Receptor Gene Maps to the Same Region on Chromosome 4 as the KIT Oncogene," Genes, Chromosomes, Cancer, 1:155 158 (1989).
Stohrer et al., "Oncotic Pressure in Solid Tumors is Elevated," Cancer Res, 60: 4251 5, (2000).
Sundström et al., "Establishment and Characterization of a Human Histiocytic Lymphoma Cell Line (U-937)," Int. J. Cancer, 17:565 577 (1976).
Swolin et al., "On the 5q-Deletion: Clinical and Cytogenetic Observations in Ten Patients and Review of the Literature," Blood, 58:986 993 (1981).
Taipale, J. et al., "Vascular Endothelial Growth Factor Receptor 3," Curr Top Microbiol Immunol., 237:85 96 (1999).
Tanaka et al., DNA sequence encoding the amino-terminal region of the human c-src protein: implications of sequence divergence among src-type kinase oncogenes, Mol. Cell Biol., 7(5):1978-83 (1987).
Tang, R. F. et al., "Overexpression of Lymphangiogenesis Growth Factor VEGF-C in Human Pancreatic Cancer," Pancreas, 22(3): 285-92 (Apr. 2001).
Tekmal, R.R. et al., "A novel in vitro and in vivo breast cancer model for testing inhibitors of estrogen biosynthesis and its action using mammary tumor cells with an activated int-5/aromatase gene," Cancer Letters, 118(1):21-28 (Sep. 1997).
Tempest, P.R. et al., "Reshaping a Human Monoclonal Antibody to Inhibit Human Respiratory Syncytial Virus Infection in Vivo," BioTechnology, 9(3):266-271 (Mar. 1991).
Terman et al., "Identification of a New Endothelial Cell growth Factor Receptor Tyrosine Kinase," Oncogene, 6(9):1677-1683 (1991).
Terman et al., "Identification of the KDR Tyrosine Kinase as a Receptor for Vascular Endothelial Cell Growth Factor," Biochem & Biophys. Res. Comm., 187(3):1579-1586 (Sep. 30, 1992).
Thompson et al., "Cloned Human Teratoma Cells Differentiate into Neuron-Like Cells and Other Cell Types in Retinoic Acid," J. Cell Sci., 72:37 64 (1984).
Thurston, G. et al., "Leakage resistant blood vessels in mice transgenically overexpressing angiopoietin 1," Science, 286(5449):2511 4 (1999).
Tischer et al., Vascular endothelial growth factor: a new member of the platelet-derived growth factor gene family, Biochem. Biophys. Res. Commun., 165(3):1198-206 (1989).
Tomiyasu et al., "Long Arm Deletion of Chromosome No. 5 in a Case of Philadelphia Chromosome-Positive Chronic Myelocytic Leukemia," Cancer Genet. Cytogenet., 2:309 315 (1980).
Tortora et al., "Differentiation of HL-60 Leukemia by Type I Regulatory Subunit Antisense Oligodeoxynucleotide of a cAMP-Dependent Protein Kinase," Proc. Nat'l Acad. Sci., USA, 88(5):2011-2015 (Mar. 1991).
Traunecker, A. et al., "Myeloma based expression system for production of large mammalian proteins," Trends in BioTechnology, 9(4):109-113 (Apr. 1991).
Tsurusaki, T., et al., "Vascular endothelial growth factor-C expression in human prostatic carcinoma and its relationship to lymph node metastasis," Br. J. Cancer, 801(2):309-313 (1999).
Ullrich et al., "Signal Transduction by Receptors with Tyrosine Kinase Activity," Cell, 61:203-212 (Apr. 20, 1990).
Valtola, R., et al., "VEGFR-3 and Its Ligand VEGF-C Are Associated with Angiogenesis in Breast Cancer," Am. J. Pathol., 154(5):1381-90 (May 1999).
Van Den Berghe et al., "Distinct Haematological Disorder with Deletion of Long Arm of No. 5 Chromosome." Nature, 251:437 439 (1974).
Van Den Berghe et al., "Transformation of Polycythemia Vera to Myelofibrosis and Late Appearance of a 5q-Chromosome Anomaly," Cancer Genet. Cytogenet., 1:157 162 (1979).

van der Putte, S.C.J., "The Development of the Lymphatic System in Man," Adv. Anat. Embryol. Cell Biol., 51:3 (1975).
Van Hinsberg et al., "Effect of Thrombin on the Production of Plasminogen Activators and PA Inhibitor-1 by Human Foreskin Microvascular Endothelial Cells," Thromb. Haemostas., 57(2):148-153 (1987).
Van Hinsberg et al., "Production of Plasminogen Activators and Inhibitors by Serially Propagated Endothelial Cells From Adult Human Blood Vessels," Arteriosclerosis, 7:389-400 (Jul./Aug. 1987).
Veikkola et al., Signaling via vascular endothelial growth factor receptor-3 is sufficient for lymphangiogenesis in transgenic mice, EMBO J., 20(6):1223-31 (2001).
Veikkola, T., et al., "Regulation of Angiogenesis Via Vascular Endothelial Growth Factor Receptors," Cancer Res., 60(2):203 12 (2000).
Verhoeyen, M. et al., "Reshaping Human Antibodies: Grafting an Antilysozyme Activity," Science, 239:1534-1536 (Mar. 1988).
Wang, "Signal Transduction in Human Hematopoietic Cells by Vascular Endothelial Growth Factor Related Protein, a Novel Ligand for the FLT4 Receptor," Blood, 90(9):3507-3515 (Nov. 1997).
Warrington et al., "Radiation of Hybrid Map of 13 Loci on the Long Arm of Chromosome 5," Genomics, 11:701 708 (1991).
Weidner, N. et al., "Tumor Angiogenesis: A New Significant and Independent Prognostic Indicator in Early-Stage Breast Carcinoma," J. Natl. Cancer Inst., 84(24):1875-1887 (Dec. 1992).
Wen, D. et al., "New Differentiation Factor: A Transmembrane Glycoprotein Containing an EGF Domain and an Immunoglobulin Homology Unit," Cell, 69:559-572 (May 1, 1992).
Weninger, W., et al., "Expression of Vascular Endothelial Growth Factor Receptor-3 and Podoplanin Suggests a Lymphatic Endothelial Cell Origin of Kaposi's Sarcoma Tumor Cells," Lab. Invest., 79(2):243-51 (Feb. 1999).
Whang Peng et al., "Cytogenic Studies in Patients With Myelofibrosis and Myeloid Metaplasia," Leuk. Res., 2:41 48 (1978).
Wilkinson et al., "Expression of the Proto-Oncogene int-1 is Restricted to Specific Neural Cells in the Developing Mouse Embryo," Cell, 50:79-88 (1987).
Williams, A.F. and Barclay, A.N., "The Immunoglobin Superfamily-Domains for Cell Surface Recognition," Ann. Rev. Immunol., 6:381 405 (1988).
Williams, J.C. et al., "N-methyl-N-nitrosourea-Induced Rat Mammary Tumors. Hormonal Responsiveness but Lack of Spontaneous Metastasis," J. Nat. Cancer Inst., 66(1):147-155 (Jan. 1981).
Witmer, et al., "VEGFR-3 in adult angiogenesis," J. Path. 195:490-497 (2001).
Witte et al., "Lymphangiogenesis: Mechanisms, Significance and Clinical Implications," in Regulation of Angiogenesis (eds. Goldberg, I.D. & Rosen, E. M.) 65-112 (birkhauser Verlag, Basel, Switzerland) 1997.
Witzenbichler, B., et al., "Vascular Endothelial Growth Factor-C (VEGF-C/VEGF-2) Promotes Angiogenesis in the Setting of Tissue Ischemia," American Journal of Pathology, vol. 153, No. 2:381-394 (Aug. 1998).
Yamaguchi et al., "Flk-1, an Flt-Related Tyrosine Kinase is an Early Marker for Endothelial Cell Precursors," Development., 118:489-498 (1993).
Yarden et al., "Human Proto-Oncogene c-kit: A New Cell Surface Receptor Tyrosine Kinase for an Unidentified Ligand," EMBO J., 6(11):3341 3351 (1987).
Ylänne et al., "Platelet Glycoprotein IIb/IIIa Complex in Cultured Cells: Localization in Focal Adhesion Sites in Spreading HEL Cells," Blood, 72: 1478 1486 (1988).
Yokoyama, Y., et al., "Prognostic Significance of Vascular Endothelial Growth Factor and Its Receptors in Endometrial Carcinoma," Gyn. Oncology 77:413-418 (2000).
Yonemura, Y. et al., "Lymphangiogenesis and the Vascular Endothelial Growth Factor Receptor (VEGFR)-3 in Gastric Cancer," Eur. J. Cancer, 37(7): 918-23 (May 2001).
Yonemura, Y., et al., "Role of Vascular Endothelial Growth Factor C Expression in the Development of Lymph Node Metastasis in Gastric Cancer," Clin. Cancer Res., 5:1823-1829 (Jul. 1999).

(56) References Cited

OTHER PUBLICATIONS

Davis-Smyth et al., The second immunoglobulin-like domain of the VEGF tyrosine kinase receptor Flt-1 determines ligand bind and may initiate a signal transduction cascade, *EMBO J.*, 15(18)4919-27 (1996).

Holash et al., VEGF-Trap: A VEGF blocker with potent antitumor effects, *Prot. Natl. Acad. Sci. USA*, 99(17):11393-8 (2002).

Oefner et la., Crystal structure of human platelet-derived growth factor BB, *EMBO J.*, 11:3921-6 (1992).

Shinkai et al., Mapping of the sites involved in ligand association and dissociation at the extracellular domain of the kinase insert domain-containing receptor for vascular endothelial growth factor, *J. Biol. Chem.*, 273:31283-8 (1998).

Stacker et al., Biosynthesis of vascular endothelial growth factor-d involves proteolytic processing with generates non-covalent homodimers, J. Biol. Chem., 274:32127 (1999).

Weismann et al., Crystal structure at 1.7 A resolution of VEGF in complex with domain 2 of the Flt-1 receptor, *Cell*, 91:695-704 (1997).

Weismann et al., Ligand-binding sites in Ig-like domains of receptor tyrosine kinases, *J. Molec. Med.*, 78:247-60 (2000).

Yu et al., Soluble vascular endothelial growth factor decoy receptor FP3 exerts potent antiangiogenic effects, *Molec. Ther.*, 20:938-47 (2012).

Baldwin et al., J. Biol. Chem., 276: 19166-19171 (2001.

Bork et al., J.Mol.Biol. 242: 309-320 (1994).

Halaby et al., J Mol Evol., 46(4): 389-400 (1998).

Halaby et al., Protein Engineering, 12(7): 563-571 (1999).

Massague et al., Annu. Rev. Cell. Biol., 6:597-641 (1990),Halaby et al., *Protein Engineering*, 12(7): 563-571 (1999).

Pavlakovic et al., (2010), Ann. N Y Acad. Sci., 1207(Suppl 1): E7-E15.

Popkov et al., J.Immunological Methods (2004), 288(1-2): 149-164.

Sotos et al., Statistics Education Research J., 8(2): 33-55 (2009).

Fuh et al., Requirements for binding and signaling of the kinase domain receptor for vascular endothelial growth factor, J. Biol. Chem., 11197-204 (1998).

```
                                                                                    SS
                                                                                    ─

Ig I
                                                                                    ───

Ig II
                                                                                    ────

FLT4    1 MQ..RGAALCLRLWLCLGLLDG LVSGYSMTPPTLNITEESHVIDTGDSLS    48
            :::  |  ::  |:   ||    |   ::.|.:::  |:.|:
FLT1    1 MVSYWDTGVLLCALLSCLLLTG SSSGSKLKDPELSLKGTQHIMQAGQTLH    50

FLT4   49 ISC RGQHPLEWAWPGAQEAPATGDKDSEDTGVVRDCEGTDARPYCKVLLL       98
          :   ..|::   .|:|  ||     :  ::  ||  ||    .|  |||
FLT1   51 LQC RGEAAHKWSLPE......MVSKESERLSITKSACGRNGKQFCSTLTL       94

FLT4   99 HEVHANDTGSYV C YKYIKARIEGTTAASSYVFVRDFEQPFINK....PD      144
          :  |  |:  |  |  ||:.|  |: :|| |:||  |:|| ||     ::
FLT1   95 NTAQANHTGFYS C KYLAVPTSKKKETESAIYIFISDTGRPFVEMYSEIPE     144

FLT4  145 TLLVNRKDAMWVP C LVSIPGLNVTLRS.QSSVLWPDGQEVVWDDRRGMLV      193
           .:   ||  |    |.  |  |||  |||   |    ::.|.|:::
FLT1  145 IIHMTEGRELVIP C RVTSPNITVTLKKFPLDTLIPDGKRIIWDSRKGFII     194

FLT4  194 STPLLHDALYLQ C ETTWGDQDFLSNPFLVHITGNELYDIQLLPRKSLELL     243
          |.:  |  |:   |   |  |     |.  ::|  |:   ..:  ||
FLT1  195 SNATYKEIGLLT C EATVNGHLYKTN.YLTHRQTNTIIDVQISTRPVKLL     243
```

FIG. 2A

```
FLT4  244 VGEKLVLNCTVWAEFNSGVTFDWDYPGKQAERGKWVPERR....SQQTHT 289
              .:|:||||| ::.:|.:|.||                                    
FLT1  244 RGHTLVLNCTATTPLNTRVQMTWSYPD...EKNKRASVRRRIDQSNSHAN 290

FLT4  290 ELSSILTIHNVSQHDLGSYVCKANNGIQRFRESTEVIVHENPFISVEWLK 339
              :.|:||:||::...|||:|| |..||.|:.:.|.:|:|..|.| |            
FLT1  291 IFYSVLTIDKMQNKDKGLYTCRVRSGPSFKSVNTSVHIYDKAFITVKHRK 340

FLT4  340 GPILEATAGDELVKLPVKLAAYPPPEFQWYKDGKALSGRHS......PHAL 384
             ..:||..||.. .:|:.                                    
FLT1  341 QQVLETVAGKRSYRLSMKVKAFPSPEVVWLKDGLPATEKSARYLTRGYSL 390

FLT4  385 VLKEVTEASTGTYTLALWNSAAGLRRNISLELVVNPPQIHEKEASS.... 431
             ::::|||.:|.||:.|::.. .:|:. |||. ||. ||. ||     
FLT1  391 IIKDVTEEDAGNYTILLSIKQSNVFKNLTATLIVNVKPQIYEKAVSSFPD 440
```

Ig III

```
                                                                    Ig V
FLT4  432 PSIYSRHSRQALT[TAYGVPLPLSIQWHWRPWTPCKMFAQRSLRRRQQD 481
          |::|.  ||| ||||||:|  .| .|:|   .:    .:  :|::
FLT1  441 PALYPLGSRQILT[TAYGIPQP.TIKWFWHPCNHNHSEARCDFCSNNEES 489

FLT4  482 LMPQCRDWRAVTTQDAVNPIESLDTWTEFVEGKNKTVSKLVIQNANVSAM 531
          ::    ||  .    ::.|||||  .:.|||: ||.|:||:  .:|:::
FLT1  490 FILD......ADSNMGNRIESITQRMAIIEGKNKMASTLVVADSRISGI 532

FLT4  532 YK[EVSNKVGQDERLIYFYVTTIPDGFTIESKPSEELLEGQPVLLS[CQAD 581
          |: ||:|||| :|| |.| |:|||    ||:|| :|:   ||   :| |:
FLT1  533 YI[CASNKVGTVGRNISFYITDVPNGFHVNLEKMPT..EGEDLKLS[CTVN 580

Ig VI
FLT4  582 SYKYEHLRWYRLNLSTLHDAHGNPLLDCKNVHLFATPLAASLEEVAPGA 631
                                   ::|.|:|:.|
FLT1  581 KFLYRDVTWILL..............RTVNNRTMHYSISKQKMAITK 613

FLT4  632 RHA.TLSLSIPRVAPEHEGHYV[CEVQDRRSHDKHCHKKYLSVQALEAPRL 680
          :|| .| |::||  :.. .| | |   |  | | |||:|:|:|||||||:
FLT1  614 EHSITLNLTIMNVSLQDSGTYA[CRARNVYTGEEILQKKEITIRDQEAPYL 663
```

FIG. 2C

```
FLT4  681  TQNLTDLLVNVSDSLEMQ[LVAGAHAPSIVWYKDERLLEEKSGVDLADSN  730
              .||.|  |:.||||: ..:::  |:  |  |.|:|::.|: :::.:.:  |:|
FLT1  664  LRNLSDHTVAISSSTTLD[HANGVPEPQITWFKNNHKIQQEPGIILGPGS  713
                                                            Ig VII

FLT4  731  QKLSIQRVREEDAGRYL[GVCNAKGCVNSSASVAVEGSEDKGSME[IVILV  780
              . ||| ||||.||:||| |.|||.|||.:|.|.|..||.|||:|| |:|||
FLT1  714  STLFIERVTEEDEGVYH[KATNQKGSVESSAYLTVQGTSDKSNLE[LITLT  763

FLT4  781  GTGVIAVFFWVLLLIFC]NMRRPAHADIKTGYLSIIMDPGEVPLEEQCEY  830
              ||.|||.||:||:||:  |||||| ||| |||:|||||:|||||||||||
FLT1  764  CTCVAATLFWLLLTLLI]RKMKRSS..SEIKTDYLSIIMDPDEVPLDEQCER  812
                                                            TM

FLT4  831  LSYDASQWEFPRERLHLGRVLGYGAFGKVVEASAFGIHKGSSCDTVAVKM  880
              |.|||:|||||||||||||||:|:||||:|:|||||||:|||:|.||.|:
FLT1  813  LPYDASKWEFARERLKLGKSLGRGAFGKVVQASAFGIKKSPTCRTVAVKM  862

FLT4  881  LKEGATASEHRALMSELKILIHIGNHLNVVNLLGACTKPQGPLMVIVEFC  930
              ||||||||||:|||||||:||:|:||:||||||||||||:|||||||||:
FLT1  863  LKEGATASEYKALMTELKILTHIGHHLNVVNLLGACTKQGGPLMVIVEYC  912
                                                            TK 1

FLT4  931  KYGNLSNFLRAKRDAF...SPCAEKSPEQRGRFRAMVELARLDRRRPGSS  977
              ||||||||:|:|||||   ||.|:|.:  |.::|.|:|||||||.:|||
FLT1  913  KYGNLSNYLKSKRDLFFLNKDAALHMEPKKEKMEPGLEQGKKPRLDSVTS  962
                                                            KI
```

FIG. 2D

```
FLT4   978  DRVLFARFSKTEGGARRASPDQEAEDLWLSPLTMEDLVCYSFQVARGMEF 1027
             . :   .:: .|  |  |. ..:: :|::::|||||  |||||||||
FLT1   963  SESFASSGFQEDKSLSDVEEEEDSDGFYKEPITMEDLISYSFQVARGMEF 1012

FLT4  1028  LASRKCIHRDLAARNILLSESDVVKICDFGLARDIYKDPDYVRKGSARLP 1077
            |.:|||||||||||||||||.|||||||||||||||||.|||||| .||
FLT1  1013  LSSRKCIHRDLAARNILLSENNVVKICDFGLARDIYKNPDYVRKGDTRLP 1062

FLT4  1078  LKWMAPESIFDKVYTTQSDVWSFGVLLWEIFSLGASPYPGVQINEEFCQR 1127
            ||||||||||||:|: |||||.||||||||||||.||||||:::|.| :
FLT1  1063  LKWMAPESIFDKIYSTKSDVWSYGVLLWEIFSLGGSPYPGVQMDEDFCSR 1112

FLT4  1128  LRDGTRMRAPELATPAIRRIMLNCWSGDPKARPAFSELVEILGDLLQGRG 1177
            ||:| |||||| ..| | |||.| ||:|| ||||||||||:||||||..
FLT1  1113  LREGMRMRAPEYSTPEIYQIMLDCWHRDPKERPRFAELVEKLGDLLQANV 1162
```

```
FLT4 1178 LQEEEVCMAPRSSQSSEEGSFSQVSTMALHIAQADAEDSPPSLQRHSLA 1227

FLT1 1163 QQDGKDYIPINAILTGNSGFTYSTPAFSEDFFKESISAPKFNSGSSDDVR 1212

FLT4 1228 ARYYNWVSFPGCLARGAETRGSSRMKTFEEFPMTPTTYKGSVDNQTDSGM 1277

FLT1 1213 YVNAFKFMSLERIKTFEELLPNATSMFDDYQGDSSTLLASPMLKRFTWTD 1262

FLT4 1278 VLASEEFEQIESRHRQESGFR 1298

FLT1 1263 SKPKASLKIEV 1273
```

FIG. 2F

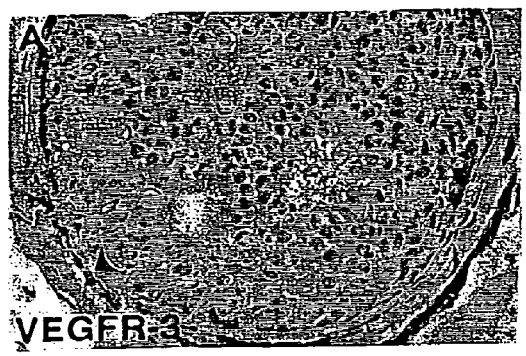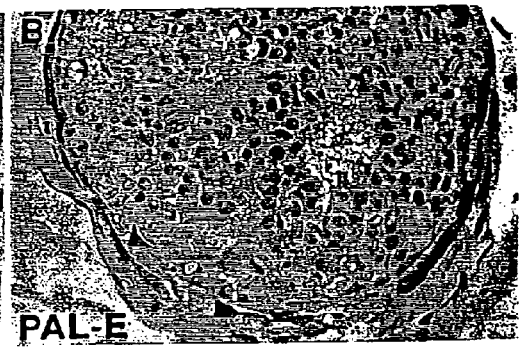
FIG. 5A    FIG. 5B

FIG. 5C    FIG. 5D

FLT4 (VEGFR-3) AS A TARGET FOR TUMOR IMAGING AND ANTI-TUMOR THERAPY

This application is a divisional of U.S. patent application Ser. No. 11/327,075, filed Jan. 6, 2006, now U.S. Pat. No. 8,940,695; which is a continuation of U.S. patent application Ser. No. 09/765,534, filed Jan. 19, 2001, now U.S. Pat. No. 7,034,105. All priority of these applications are incorporated herein by reference, in their entireties.

INCORPORATION BY REFERENCE OF MATERIAL SUBMITTED ELECTRONICALLY

Incorporated by reference in its entirety is a computer-readable amino acid sequence listing submitted concurrently herewith and identified as follows: ASCII (text) file named "34891A3_SubSeqListing.txt," 86,116 bytes, created on Nov. 17, 2014.

FIELD OF THE INVENTION

The present invention relates-generally to genes for receptors, specifically genes for receptor tyrosine kinases, their insertion into recombinant DNA vectors, and the production of the resulting proteins in host strains of microorganisms and host eukaryotic cells. More specifically, the present invention is directed to Flt4, a receptor tyrosine kinase; to nucleotide sequences encoding Flt4; to methods for the generation of DNAs encoding Flt4 and their gene products; to nucleic acid probes which specifically recognize (hybridize to) nucleic acids encoding such receptors; to antibodies that specifically recognize such receptors; and to methods of using such probes and antibodies and other Flt4 binding compounds, e.g., for identifying lymphatic vessels and high endothelial venules (HEV) in animal and human tissues and augmenting or preventing the growth of Flt4-expressing cells in pathological conditions.

BACKGROUND

The cellular behavior responsible for the development, maintenance and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long term readjustment of cellular gene expression. Several receptors associated with various cell surfaces can bind specific growth factors.

Tyrosine phosphorylation is one of the key modes of signal transduction across the plasma membrane. Several tyrosine kinase genes encode transmembrane receptors for polypeptide growth factors and hormones, such as epidermal growth factor (EGF), insulin, insulin-like growth factor-I (IGF-I), platelet derived growth factors (PDGF-A and -B) and fibroblast growth factors (FGFs) [Heldin et al., *Cell Regulation*, 1: 555-566 (1990); Ullrich et al., *Cell,* 61: 243-54 (1990)]. The receptors of several hematopoietic growth factors are tyrosine kinases; these include c-fms, which is the colony stimulating factor 1 receptor [Sherr et al., *Cell,* 41: 665-676 (1985)] and c-kit, a primitive hematopoietic growth factor receptor [Huang et al., *Cell,* 63: 225-33 (1990)].

These receptors differ in their specificity and affinity. In general, receptor tyrosine kinases are glycoproteins, which consist of an extracellular domain capable of binding a specific growth factor(s), a transmembrane domain which is usually an alpha-helical portion of the protein, a juxtamembrane domain (where the receptor may be regulated by, e.g., protein phosphorylation), a tyrosine kinase domain (which is the enzymatic component of the receptor), and a carboxy-terminal tail, which in many receptors is involved in recognition and binding of the substrates for the tyrosine kinase.

In several receptor tyrosine kinases, the processes of alternative splicing and alternative polyadenylation are capable of producing several distinct polypeptides from the same gene. These may or may not contain the various domains listed above. As a consequence, some extracellular domains may be expressed as separate proteins secreted by the cells and some forms of the receptors may lack the tyrosine kinase domain and contain only the extracellular domain inserted into the plasma membrane via the transmembrane domain plus a short carboxy-terminal tail.

The physiology of the vascular system, embryonic vasculogenesis and angiogenesis, blood clotting, wound healing and reproduction, as well as several diseases, involve the vascular endothelium lining the blood vessels. The development of the vascular tree occurs through angiogenesis, and, according to some theories, the formation of the lymphatic system starts shortly after arterial and venous development by sprouting from veins. See Sabin, F. R., *Am. J. Anat.,* 9:43 (1909); and van der Putte, S. C. J, *Adv. Anat. Embryol. Cell Biol.,* 51:3 (1975).

After the fetal period, endothelial cells proliferate very slowly, except during angiogenesis associated with neovascularization. Growth factors stimulating angiogenesis exert their effects via specific endothelial cell surface receptor tyrosine kinases.

Among ligands for receptor tyrosine kinases, the Platelet Derived Growth Factor (PDGF) has been shown to be angiogenic, albeit weakly, in the chick chorioallantoic membrane. Transforming Growth Factor α (TGFα) is an angiogenic factor secreted by several tumor cell types and by macrophages. Hepatocyte Growth Factor (HGF), the ligand of the c-met proto-oncogene-encoded receptor, is also strongly angiogenic, inducing similar responses to those of TGFα in cultured endothelial cells.

Evidence shows that there are endothelial cell specific growth factors and receptors that may be primarily responsible for the stimulation of endothelial cell growth, differentiation, as well as certain of differentiated functions. The most-widely studied growth factor is Vascular Endothelial Growth Factor (VEGF), a member of the PDGF family. Vascular endothelial growth factor is a dimeric glycoprotein of disulfide-linked 23 kDa subunits, discovered because of its mitogenic activity toward endothelial cells and its ability to induce vessel permeability (hence its alternative name vascular permeability factor). Other reported effects of VEGF include the mobilization of intracellular $Ca^{2+}$, the induction of plasminogen activator and plasminogen activator inhibitor-1 synthesis, stimulation of hexose transport in endothelial cells, and promotion of monocyte migration in vitro. Four VEGF isoforms, encoded by distinct mRNA splicing variants, appear to be equally capable of stimulating mitogenesis of endothelial cells. The 121 and 165 amino acid isoforms of VEGF are secreted in a soluble form, whereas the isoforms of 189 and 206 amino acid residues remain associated with the cell surface and have a strong affinity for heparin. Soluble non-heparin-binding and heparin-binding forms have also been described for the related placenta growth factor (PlGF; 131 and 152 amino acids, respectively), which is expressed in placenta, trophoblastic tumors, and cultured human endothelial cells.

The pattern of VEGF expression suggests its involvement in the development and maintenance of the normal vascular system and in tumor angiogenesis. During murine development, the entire 7.5 day post-coital endoderm expresses VEGF and the ventricular neuroectoderm produces VEGF at the capillary ingrowth stage. On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized, VEGFR-1/Flt1 (fms-like tyrosine kinase-1) and VEGFR-2/Kdr/Flk-1 (kinase insert domain containing receptor/fetal liver kinase-1). These receptors are classified in the PDGF-receptor family. However, the VEGF receptors have seven immunoglobulin-like loops in their extracellular domains (as opposed to five in other members of the PDGF family) and a longer kinase insert. The expression of VEGF receptors occurs mainly in vascular endothelial cells, although some may also be present on monocytes and on melanoma cell lines. Only endothelial cells have been reported to proliferate in response to VEGF, and endothelial cells from different sources show different responses. Thus, the signals mediated through VEGFR-1 and VEGFR-2 appear to be cell type specific.

VEGFR-1 and VEGFR-2 bind VEGF165 with high affinity ($K_d$ about 20 pM and 200 pM, respectively). Flk-1 receptor has also been shown to undergo autophosphorylation in response to VEGF, but phosphorylation of Flt1 was barely detectable. VEGFR-2 mediated signals cause striking changes in the morphology, actin reorganization and membrane ruffling of porcine aortic endothelial cells overexpressing this receptor. In these cells, VEGFR-2 also mediated ligand-induced chemotaxis and mitogenicity; whereas VEGFR-1 transfected cells lacked mitogenic responses to VEGF. In contrast, VEGF had a strong growth stimulatory effect on rat sinusoidal endothelial cells expressing VEGFR-1. Phosphoproteins co-precipitating with VEGFR-1 and VEGFR-2 are distinct, suggesting that different signalling molecules interact with receptor specific intracellular sequences.

In in situ hybridization studies, mouse VEGFR-2 mRNA expression was found in yolk sac and intraembryonic mesoderm (estimated 7.5 day post-coitum (p.c.) embryos, from which the endothelium is derived, and later in presumptive angioblasts, endocardium and large and small vessel endothelium (12.5 days p.c.). Abundant VEGFR-2 mRNA in proliferating endothelial cells of vascular sprouts and branching vessels of embryonic and early postnatal brain and decreased expression in adult brain suggested that VEGFR-2 is a major regulator of vasculogenesis and angiogenesis. VEGFR-1 expression was similarly associated with early vascular development in mouse embryos and with neovascularization in healing skin wounds. However, high levels of VEGFR-1 expression were detected in adult organs, suggesting that VEGFR-1 has a function in quiescent endothelium of mature vessels not related to cell growth. The avian homologue of VEGFR-2 was observed in the mesoderm from the onset of gastrulation, whereas the VEGFR-1 homologue was first found in cells co-expressing endothelial markers. In in vitro quail epiblast cultures, FGF-2, which is required for vasculogenic differentiation of these cells, upregulated VEGFR-2 expression. The expression of both VEGF receptors was found to become more restricted later in development. In human fetal tissues VEGFR-1 and VEGFR-2 showed overlapping, but slightly different, expression patterns. These data suggest that VEGF and its receptors act in a paracrine manner to regulate the differentiation of endothelial cells and neovascularization of tissues.

VEGF recently has been shown to be a hypoxia-induced stimulator of endothelial cell growth and angiogenesis, and inhibition of VEGF activity using specific monoclonal antibodies has been shown to reduce the growth of experimental tumors and their blood vessel density. [Ferrara et al. *Endocrine Reviews,* 18: 4-25 (1997); Shibuya et al., *Adv. Cancer Res.,* 67: 281-316 (1995); Kim et al. *Nature.* 362: 841-844 (1993).].

Growth of solid tumors beyond a few cubic millimeters in size is dependent on vascular supply, making angiogenesis an attractive target for anti-cancer therapy. Encouraging results have been reported with endogenous angiogenic inhibitors or "statins" which include angiostatin, a fragment of plasminogen, and endostatin, a fragment of collagen 18. [O'Reilly et al., *Cell,* 79: 315-328 (1994); O'Reilly et al., *Cell,* 88: 277-85 (1997).]. Both factors are normally produced by primary tumors and keep metastasis dormant. Systemic administration of either statin has been shown to also induce and sustain dormancy of primary tumors in animal models. The receptors and signalling by statins, as well as the proteases which activate them, remain to be identified. A need exists for additional therapeutic molecules for controlling angiogenesis in the treatment of cancer and other pathological disease states.

Primary breast cancers have been shown to express several angiogenic polypeptides, of which VEGF was the most abundant. [See, e.g., Relf et al., *Cancer Res.,* 57: 963-969 (1997).] Tumor cells contained high levels of VEGF mRNA in both invasive and non-invasive, ductal (in situ) breast carcinomas. [Brown et al., *Hum. Pathol.,* 26: 86-91 (1995).] The endothelial cells adjacent to the in situ carcinomas expressed VEGFR-1 and VEGFR-2 mRNA. VEGF and its receptors may contribute to the angiogenic progression of malignant breast tumors, because in several independent studies, correlations have been found between tumor vascular density and the prognosis of the disease. [Weidner et al., *J. Natl. Cancer Inst.,* 84: 1875-1887 (1992).] A need exists for additional markers for breast cancer and breast cancer-related angiogenesis, to improve diagnosis and screening and to serve as a target for therapeutic intervention.

A major function of the lymphatic system is to provide fluid return from tissues and to transport many extravascular substances back to the blood. In addition, during the process of maturation, lymphocytes leave the blood, migrate through lymphoid organs and other tissues, and enter the lymphatic vessels, and return to the blood through the thoracic duct. Specialized venules, high endothelial venules (HEVs), bind lymphocytes again and cause their extravasation into tissues. The lymphatic vessels, and especially the lymph nodes, thus play an important role in immunology and in the development of metastasis of different tumors.

Since the beginning of the 20th century, three different theories concerning the embryonic origin of the lymphatic system have been presented. However, lymphatic vessels have been difficult to identify, due to the absence of known specific markers available for them.

Lymphatic vessels are most commonly studied with the aid of lymphography. In lymphography, X-ray contrast medium is injected directly into a lymphatic vessel. That contrast medium is distributed along the efferent drainage vessels of the lymphatic system. The contrast medium is collected in lymph nodes, where it stays for up to half a year, during which time X-ray analyses allow the follow-up of lymph node size and architecture. This diagnostic is especially important in cancer patients with metastases in the lymph nodes and in lymphatic malignancies, such as lymphoma. However, improved materials and methods for imaging lymphatic tissues are needed in the art.

SUMMARY OF THE INVENTION

The present invention addresses a gene for a novel receptor tyrosine kinase located on chromosome 5, identified as an unknown tyrosine kinase-homologous PCR-cDNA fragment from human leukemia cells [Aprelikova et al., *Cancer Res.*, 52: 746-748 (1992)]. This gene and its encoded protein are called Flt4. This abbreviation comes from the words fms-like tyrosine kinase 4.

Flt4 is a receptor tyrosine kinase closely related in structure to the products of the VEGFR-1 and VEGFR-2 genes. By virtue of this similarity and subsequently-discovered similarities between ligands for these three receptors, the Flt4 receptor has additionally been named VEGFR-3. The names Flt4 and VEGFR-3 are used interchangeably herein. Despite the similarity between these three receptors, the mature form of Flt4 differs from the VEGFRs in that it is proteolytically cleaved in the extracellular domain into two disulfide-linked polypeptides of 125/120 kD and 75 kD. The Flt4 gene encodes 4.5 and 5.8 kb mRNAs which exhibit alternative 3' exons and encode polypeptides of 190 kD and 195 kD, respectively.

Further evidence of a distinction is that VEGF does not show specific binding to Flt4 and doesn't induce its autophosphorylation.

A comparison of Flt4, Flt1, and KDR/Flk-1 receptor mRNA signals showed overlapping, but distinct expression patterns in the tissues studied. Kaipainen, et al., *Exp. Med.*, 178:2077 (1993). Flt4 gene expression appears to be more restricted than the expression of VEGFR-1 or VEGFR-2. The expression of Flt4 first becomes detectable by in situ hybridization in the angioblasts of head mesenchyme, the cardinal vein and extraembryonically in the allantois of 8.5 day post-coital mouse embryos. In 12.5 day post-coital embryos the Flt4 signal is observed on developing venous and presumptive lymphatic endothelia, but arterial endothelia appear to be negative. During later stages of development, Flt4 mRNA becomes restricted to developing lymphatic vessels. Only the lymphatic endothelia and some high endothelial venules express Flt4 mRNA in adult human tissues and increased expression occurs in lymphatic sinuses in metastatic lymph nodes and in lymphangioma. The results support the theory of the venous origin of lymphatic vessels.

The protein product of the Flt4 receptor tyrosine kinase cDNA, cloned from a human erythroleukemia cell line, is N-glycosylated and contains seven immunoglobulin-like loops in its extracellular domain. The cytoplasmic tyrosine kinase domain of Flt4 is about 80% identical at the amino acid level with the corresponding domains of Flt1 and KDR and about 60% identical with the receptors for platelet-derived growth factor, colony stimulating factor-1, stem cell factor, and the Flt3 receptor. See Pajusola et al., *Cancer Res.*, 52:5738 (1992).

The present invention provides isolated polynucleotides (e.g., DNA or RNA segments of defined structure) encoding an Flt4 receptor tyrosine kinase useful in the production of Flt4 protein and peptide fragments thereof and in recovery of related genes from other sources.

The present invention provides a recombinant DNA vector containing a heterologous segment encoding the Flt4 receptor tyrosine kinase or a related protein that is capable of being inserted into a microorganism or eukaryotic cell and that is capable of expressing the encoded protein.

The present invention provides eukaryotic cells capable of producing useful quantities of the Flt4 receptor tyrosine kinase and proteins of similar function from many species.

The present invention provides peptides that may be produced synthetically in a laboratory or by microorganisms, which peptides mimic the activity of the natural Flt4 receptor tyrosine kinase protein. In another embodiment, the invention is directed to peptides which inhibit the activity of Flt4 receptor tyrosine kinase protein.

Particularly preferred are peptides selected from the group consisting of: (a) a Flt4-short form, the nucleotide and deduced amino acid sequence of which appear in SEQ. ID NOs. 1 and 2; and (b) a second form with different nucleotide and corresponding amino acid residues at its carboxyl terminal, i.e.; an Flt4-long form, the nucleotide and deduced amino acid sequence of which appear in SEQ. ID NOs. 3 and 4. The Flt4 long form has a length of 1363 amino acid residues.

DNA and RNA molecules, recombinant DNA vectors, and modified microorganisms or eukaryotic cells comprising a nucleotide sequence that encodes any of the proteins or peptides indicated above are also part of the present invention. In particular, sequences comprising all or part of the following two DNA sequences, a complementary DNA or RNA sequence, or a corresponding RNA sequence are especially preferred: (a) a DNA sequence such as SEQ ID NO: 1, encoding Flt4-short form [SEQ ID NO: 2], and (b) a DNA sequence such as SEQ ID NO: 3, encoding a Flt4 wherein nucleotides 3913-4416 of SEQ ID NO: 1 are changed, encoding Flt4-long form [SEQ ID NO: 4].

DNA and RNA molecules containing segments of the larger sequence are also provided for use in carrying out preferred aspects of the invention relating to the production of such peptides by the techniques of genetic engineering and the production of oligonucleotide probes.

Because the DNA sequence encoding the Flt4 protein is identified herein, DNA encoding the Flt4 protein may be produced by, e.g., polymerase chain reaction or by synthetic chemistry using commercially available equipment, after which the gene may be inserted into any of the many available DNA vectors using known techniques of recombinant DNA technology. Furthermore, automated equipment is also available that makes direct synthesis of any of the peptides disclosed herein readily available.

The present invention also is directed to Flt4 peptides and other constructs and to the use of Flt4 as a specific marker for lymphatic endothelial cells.

In a specific embodiment, the invention is directed to nucleic acid probes and antibodies recognizing Flt4, especially to monoclonal antibodies, and compositions containing such antibodies.

Also in a specific embodiment, the invention is directed to a method for monitoring lymphatic vessels in tissue samples and in organisms. Further, is it an object of the present invention to provide clinical detection methods describing the state of lymphatic tissue, and especially lymphatic vessels (inflammation, infection, traumas, growth, etc.), and to provide methods for detecting lymphatic vessels, and thus lymphatic vascularization, in an organism.

It is a further object of the present invention to provide monoclonal antibodies which specifically recognize the Flt4 receptor protein or various epitopes thereof. It is an object of the invention to use these monoclonal antibodies for diagnostic purposes for detecting and measuring the amount of Flt4 receptors in tissues, especially in lymphatic tissues. In the context of anti-Flt4 antibodies, the terms "specifically recognize Flt4," "specifically bind to Flt4," "specific for Flt4," and the like mean that an antibody will bind to (immunoreact with) Flt4 preferentially over other endothelial cell surface receptors, including VEGFR-2/Kdr/Flk-1 and VEGFR-1/Flt1. Thus, anti-Flt4 antibodies or other Flt4 binding compounds that are "specific for" Flt4 are useful for identification and/or labelling of Flt4 in tissues or biological samples in accordance with the methods of the invention as described herein (e.g., medical imaging, detection, screening, or targeted therapy), because they fail to bind epitopes of other antigens at all, or bind other antigens only with an affinity that is sufficiently lower than their Flt4 binding affinity to be insignificant in these practical contexts.

Another aspect of the present invention relates to a method of determining the presence of Flt4-receptors in a cell sample, comprising the steps of: (a) exposing a cell sample to an antibody, especially a monoclonal antibody, of the present invention; and (b) detecting the binding of said monoclonal antibody to Flt4 receptors. As will be apparent from the detailed description which follows, information concerning the presence, quantity, density, and location of Flt4 receptor in tissue samples has diagnostic and prognostic relevance with respect to the type and severity of a disease state; and has therapeutic relevance where it is desirable to specifically tailor anti-Flt4-based treatment regimens to only those patients having diseases characterized by Flt4 expression in tumors or in blood or lymphatic vessels and tissues surrounding, serving, or supplying a tumor. The screening for the presence of Flt4 receptors thus can constitute a first step in a therapeutic regimen, and/or a monitoring step during the course of therapy.

The invention is further directed to a method of modulating (e.g., antagonizing or augmenting) the function of Flt4 in lymphatic vascularization and in inflammatory, infectious and immunological conditions. For example, in one embodiment, such a method comprises inhibiting the Flt4-mediated lymphatic vascularization by providing amounts of a Flt4-binding compound sufficient to block the Flt4 endothelial cell sites participating in such reaction, especially where Flt4 function is associated with a disease such as metastatic cancers, lymphomas, inflammation (chronic or acute), infections and immunological diseases. Since many tumors metastasize through the lymphatic vessels, therapy directed to blocking the interaction between Flt4 ligands and Flt4 is expected to have broad application for inhibition of tumor metastasis as part of an anti-cancer treatment regimen.

The invention is further directed to a specific Flt4-stimulating ligand and monoclonal antibodies and their use for stimulating lymphatic endothelia and fragments and peptides as well as antibodies derived from research on the ligand to inhibit Flt4 function when desirable, such as in various disease states involving Flt4 function.

The invention provides a cell line source for the ligand of the Flt4 receptor tyrosine kinase. Using the conditioned medium from these cells, the Flt4 ligand may be purified and cloned by using methods standard in the art. Using this conditioned medium or the purified ligand, an assay system for Flt4 ligand and dimerization inhibitors as well as inhibitors of Flt4 signal transduction are obtained, which allow for identification and preparation of such inhibitors.

In a preferred embodiment of the invention, conditioned medium from the PC-3 cell line comprises a protein or a fragment thereof, which is capable of stimulating the Flt4 receptor and regulating the growth and differentiation as well as the differentiated functions of certain endothelial cells. The Flt4 ligand or its peptides or derivatives are useful in the regulation of endothelial cell growth, differentiation and their differentiated functions and in the generation of agonists and antagonists for the ligand. Particularly, the Flt4 ligand is useful in regulating lymphatic endothelia. However, the Flt4 ligand, when purified, or produced from a recombinant source, may also stimulate the related KDR/Flk-1 receptor.

The identification of Flt4-stimulating ligand makes it directly possible to assay for inhibitors of this ligand or inhibitors of Flt4 function. Such inhibitors are simply added to the conditioned media containing the Flt4 ligand and if they inhibit autophosphorylation, they act as Flt4 signalling inhibitors. For example, recombinant or synthetic peptides (including but not limited to fragments of the Flt4 extracellular domain) may be assayed for inhibition of Flt4-ligand interaction or Flt4 dimerization. Such putative inhibitors of Flt4 and, in addition, antibodies against the Flt4 ligand, peptides or other compounds blocking Flt4 receptor-ligand interaction, as well as antisense oligonucleotides complementary to the sequence of mRNA encoding the Flt4 ligand are useful in the regulation of endothelial cells and in the treatment of diseases associated with endothelial cell function.

A detailed characterization of the Flt4 ligand, designated VEGF-C, is provided in PCT Patent Application No. PCT/US98/01973, filed 2 Feb. 1998, and published as International Publication No. WO 98/33917; in PCT Patent Application PCT/FI96/00427, filed Aug. 1, 1996, and published as International Publication WO 97/05250; and in the U.S. patent application priority documents relied upon therein for priority, all of which are incorporated herein by reference. The deduced amino acid sequence for prepro-VEGF-C is set forth herein in SEQ ID NO: 21.

A detailed description of a second Flt4 ligand, designated VEGF-D, is provided in Achen, et al., *Proc. Nat'l Acad. Sci. U.S.A.*, 95(2): 548-553 (1998), and in Genbank Accession No. AJ000185, both of which are incorporated herein by reference. The deduced amino acid sequence for prepro-VEGF-D is set forth herein in SEQ ID NO: 22.

The invention also is directed to a method of treating a mammalian organism suffering from a disease characterized by expression of Flt4 tyrosine kinase (Flt4) in cells, comprising the step of administering to the mammalian organism a composition, the composition comprising a compound effective to inhibit the binding of an Flt4 ligand protein to Flt4 expressed in cells of the organism, thereby inhibiting Flt4 function. The disease may be diseases already mentioned above, such as diseases characterized by undesirable lymphatic vascularization. Additionally, it has been discovered that Flt4 expression also occurs in blood vessel vasculature associated with at least some breast cancers, and possibly other cancers (i.e., at a level greatly exceeding the barely detectable or undetectable levels of expression in blood vessel vasculature of corresponding normal (healthy) tissue). Thus, in a preferred embodiment, the cells comprise endothelial cells (lymphatic or vascular). In another embodiment, the cells comprise neoplastic cells such as certain lymphomas that express Flt4. Treatment of humans is specifically contemplated.

By "compound effective to inhibit the binding of an Flt4 ligand protein to Flt4 expressed in cells of the organism" is meant any compound that inhibits the binding of the Flt4 ligand described herein as vascular endothelial growth factor C, as isolatable from PC-3 conditioned medium. It is contemplated that such compounds also will be effective for inhibiting the binding of vascular endothelial growth factor D to Flt4. Exemplary compounds include the following polypeptides: (a) a polypeptide comprising an antigen-binding fragment of an anti-Flt4 antibody; (b) a polypeptide comprising a soluble Flt4 fragment (e.g., an extracellular domain fragment), wherein the fragment and the polypeptide are capable of binding to an Flt4 ligand; (c) a polypeptide comprising a fragment or analog of a vertebrate vascular endothelial growth factor C (VEGF-C) polypeptide, wherein the polypeptide and the fragment or analog bind, but fail to activate, the Flt4 expressed on native host cells (i.e., cells of the organism that express the native Flt4 protein on their surface); and (d) a polypeptide comprising a fragment or analog of a vertebrate vascular endothelial growth factor-D (VEGF-D) polypeptide, wherein the polypeptide and the fragment or analog bind, but fail to activate, the Flt4 expressed on native host cells. Small molecule inhibitors identifiable by standard in vitro screening assays, e.g., using VEGF-C and recombinantly-expressed Flt4 also are contemplated. Polypeptides comprising an antigen-binding fragment of an anti-Flt4 antibody are highly preferred. Such polypeptides include, e.g., polyclonal and monoclonal antibodies that specifically, bind Flt4; fragments of such antibodies; chimaeric and humanized antibodies; bispecific antibodies that specifically bind to Flt4 and also specifically bind to another antigen, and the like. Use of compounds that bind to circulating Flt4 ligand and thereby inhibit the binding of the ligand to Flt4 also is contemplated. Such compounds include anti-VEGF-C or anti-VEGF-D antibodies or polypeptides that comprise antigen-binding fragments thereof. In a related variation, the invention contemplates methods of treatment that disrupt downstream intracellular Flt4 signalling, thereby inhibiting Flt4 function.

In a preferred variation, the compound further comprises a detectable label as described elsewhere herein, or a cytotoxic agent. Exemplary cytotoxic agents include plant toxins (e.g., ricin, saporin), bacterial or fungal toxins, radioisotopes (e.g., 211-Astatine, 212-Bismuth, 90-Yttrium, 131-Iodine, 99m-Technitium, and others described herein), anti-metabolite drugs (e.g., methotrexate, 5-fluorodeoxyuridine), alkylating agents (e.g., chlorambucil), anti-mitotic agents (e.g., vinca alkaloids), and DNA intercalating agents (e.g., adriamycin). Other exemplary agents include compounds or treatments that induce DNA damage when applied to a cell. Such agents and factors include radiation and waves that induce DNA damage such as, gamma-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D; mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. Still other agents are adriamycin (also known as doxorubicin), VP-16 (also known as etoposide), and the like, daunorubicin (intercalates into DNA, blocks DNA-directed RNA polymerase and inhibits DNA synthesis); mitomycin (also known as mutamycin and/or mitomycin-C); Actinomycin D; vincristine and cyclophosphamide; Bleomycin; VP16 (etoposide); Tumor Necrosis Factor [TNF;] Taxol; Melphalan; Cyclophosphamide, Chlorambucil. Administration of the peptides of the present invention may precede or follow the other agent treatment by intervals ranging from minutes to weeks. In embodiments where the other agent and expression construct are administered separately, one would generally ensure that a significant period of time did not expire between the time of each delivery, such that the agent and the peptide-based therapeutic would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated.

Likewise, to improve administration, the composition preferably further comprises a pharmaceutically acceptable diluent, adjuvant, or carrier medium.

As explained in detail herein, Flt4 expression, while largely restricted to the lymphatic endothelia of healthy adults, has been identified in the blood vasculature surrounding at least certain tumors. Thus, the invention further includes a method of treating a mammalian organism suffering from a neoplastic disease characterized by expression of Flt4 tyrosine kinase (Flt4) in vascular endothelial cells, comprising the steps of administering to a mammalian organism in need of such treatment a composition, the composition comprising a compound effective to inhibit the binding of an Flt4 ligand protein to Flt4 expressed in vascular endothelial cells of the organism, thereby inhibiting Flt4-mediated proliferation of the vascular endothelial cells. Treatment of neoplastic diseases selected from carcinomas (e.g., breast carcinomas), squamous cell carcinomas, lymphomas, melanomas, and sarcomas, are specifically contemplated. However, it will be readily apparent that the screening techniques described herein in detail will identify other tumors characterized by Flt4 expression in vascular endothelial cells, which tumors are candidates susceptible to the anti-Flt4 treatment regimens described herein. Treatment of breast carcinomas characterized by expression of Flt4 in vascular endothelial cells is specifically contemplated. By neoplastic disease characterized by expression of Flt4 tyrosine kinase in vascular endothelial cells is meant a disease wherein Flt4 is identifiable in blood vasculature at a much higher level than the undetectable or barely detectable levels normally observed in the blood vascular of healthy tissue, as exemplified herein.

Therapeutically effective amounts of compounds are empirically determined using art-recognized dose-escalation and dose-response assays. By therapeutically effective for treatment of tumors is meant an amount effective to reduce tumor growth, or an amount effective to stop tumor growth, or an amount effective to shrink or eliminate tumors altogether, without unacceptable levels of side effects for patients undergoing cancer therapy. Where the compound comprises an antibody or other polypeptide, doses on the order of 0.1 to 100 mg antibody per kilogram body weight, and more preferably 1 to 10 mg/kg, are specifically contemplated. For humanized antibodies, which typically exhibit a long circulating half-life, dosing at intervals ranging from daily to every other month, and more preferably every week, or every other week, or every third week, are specifically contemplated. Monitoring the progression of the therapy, patient side effects, and circulating antibody levels will provide additional guidance for an optimal dosing regimen. Data from published and ongoing clinical trials for other antibody-based cancer therapeutics (e.g., anti-HER2, anti-EGF receptor) also provide useful dosing regimen guidance.

For therapeutic methods described herein, preferred compounds include polypeptides comprising an antigen-binding fragment of an anti-Flt4 antibody, and polypeptides comprising a soluble Flt4 extracellular domain fragment. Human and humanized anti-Flt4 antibodies are highly preferred. Highly preferred Flt4 extracellular domain fragments comprise ligand binding portions of the Flt4 extracellular domain. For example, a soluble fragment comprising the first three immunoglobulin-like domains of the Flt4 extracellular domain is highly preferred. Smaller fragments that bind Flt4 ligands alone, or when fused to other peptides (such as immunoglobulin-like domains of VEGFR-1 or VEGFR-2), also are contemplated. Similarly, modifications which improve solubility and/or stability, serum half-life, or other properties to improve therapeutic efficacy are contemplated. For example, polypeptides comprising fusions between Flt4 extracellular domain and an immunoglobulin Fc peptide (especially an IgG1 Fc isotype) to improve solubility and serum-half life, are contemplated. [Compare Achen et al., Proc. Natl. Acad. Sci. USA, 95: 548-553 (1998).]

An expected advantage of the therapeutic methods of the invention lies in the fact that Flt4 is normally not expressed at any significant level in the blood vasculature of healthy tissues. In a highly preferred embodiment, the therapeutic compound comprises a bispecific antibody, or fragment thereof, wherein the antibody or fragment specifically binds Flt4 and specifically binds a blood vascular endothelial marker antigen. By "blood vascular endothelial marker antigen" is meant any cell surface antigen that is expressed on proliferating vascular endothelial cells, and, preferably, that is not expressed on lymphatic endothelial cells. Exemplary blood vascular endothelial markers include PAL-E [deWaal, et al. *Am. J. Pathol.,* 150:1951-1957 (1994)], VEGFR-1 and VEGFR-2 [Ferrara et al., *Endocrine Reviews,* 18:4-25 (1997], Tie [Partanen et al., *Mol. Cell. Biol.,* 12: 1698-1707 (1992)], endoglin [U.S. Pat. No. 5,776,427, incorporated herein by reference in its entirety], and von Willebrandt Factor. Such bispecific antibodies are expected to preferentially locate to the tumor-associated vasculature that expresses both Flt4 and the blood vascular endothelial marker. In a highly preferred embodiment, the compound further comprises an anti-neoplastic or cytotoxic agent conjugated to the bispecific antibody, for the purposes of killing the tumor cells and/or killing the vasculature supply to the tumor cells. Exemplary agents include those described above, and also therapeutic proteins, such as statins, cytokines, chemokines, and the like, to stimulate an immune response to the tumor in the host.

In an alternative embodiment, the compound comprises an antibody (or bispecific antibody) that recognizes an epitope (or epitopes) comprised of an Flt4/Flt4 ligand complex (e.g., a complex comprised of Flt4 bound to VEGF-C or VEGF-D).

It is further contemplated that the therapeutic compound will be conjugated or co-administered with broad spectrum agents that have potential to inhibit angiogenic factors. Such agents include, e.g., heparin binding drugs (such as pentosan and suramin analogs) that may inhibit angiogenic factors that bind heparin; and chemical agents that block endothelial cell growth and migration, such as fumagillin analogs. Other agents currently under investigation include Marimastat (British Biotech, Annapolis Md.; indicated for non-small cell lung, small cell lung and breast cancers); AG3340 (Agouron, LaJolla, Calif.; for glioblastoma multiforme); COL-3 (Collagenex, Newtown Pa.; for brain tumors); Neovastat (Aeterna, Quebec, Canada; for kidney and non-small cell lung cancer) BMS-275291 (Bristol-Myers Squibb, Wallingford Conn.; for metastatic non-small cell lung cancer); Thalidomide (Celgen; for melanoma, head and neck cancer, ovarian, metastatic prostate, and Kaposi's sarcoma; recurrent or metastatic colorectal cancer (with adjuvants); gynecologic sarcomas, liver cancer; multiple myeloma; CLL, recurrent or progressive brain cancer, multiple myeloma, non-small cell lung, nonmetastatic prostate, refractory multiple myeloma, and renal cancer); Squalamine (Magainin Pharmaceuticals Plymouth Meeting, Pa.; non-small cell cancer and ovarian cancer); Endostatin (EntreMEd, Rockville, Md.; for solid tumors); SU5416 (Sugen, San Francisco, Calif.; recurrent head and neck, advanced solid tumors, stage IIIB or IV breast cancer; recurrent or progressive brain (pediatric); Ovarian, AML; glioma, advanced malignancies, advanced colorectal, von-Hippel Lindau disease, advanced soft tissue; prostate cancer, colorectal cancer, metastatic melanoma, multiple myeloma, malignant mesothelioma: metastatic renal, advanced or recurrent head and neck, metastatic colorectal cancer); SU6668 (Sugen San Francisco, Calif.; advanced tumors); interferon-α; Anti-VEGF antibody (NAtional Cancer Institute, Bethesda Md.; Genentech San Francisco, Calif.; refractory solid tumors; metastatic renal cell cancer, in untreated advanced colorectal); EMD121974 (Merck KCgaA, Darmstadt, Germany; HIV related Kaposi's Sarcoma, progressive or recurrent Anaplastic Glioma); Interleukin 12 (Genetics Institute, Cambridge, Mass.; Kaposi's sarcoma) and IM862 (Cytran, Kirkland, Wash.; ovarian cancer, untreated metastatic cancers of colon and rectal origin and Kaposi's sarcoma).

Conjugation of the anti-Flt4 compound to a prodrug that would be targeted to tumor vessels by the anti-Flt4 compound and then activated (e.g., by irradiation) locally at sites of tumor growth also is contemplated. Use of such prodrug strategy has the expected advantage of minimizing side effects of the drug upon healthy lymphatic vessels that express Flt4.

Similarly, the invention includes a method of treating a mammalian organism suffering from a neoplastic disease characterized by expression of Flt4 tyrosine kinase (Flt4) in vascular endothelial cells, comprising the steps of: identifying a mammalian organism suffering from a neoplastic disease state characterized by expression of Flt4 in vascular endothelial cells, and administering to the mammalian organism in need of such treatment a composition, the composition comprising a compound effective to inhibit the binding of an Flt4 ligand protein to Flt4 expressed in vascular endothelial cells of the organism, thereby inhibiting Flt4-mediated proliferation of the vascular endothelial cells.

The invention also provides a method for screening a biological sample for the presence of Flt4 receptor tyrosine kinase protein (Flt4), comprising the steps of (a) contacting a biological sample suspected of containing Flt4 with a composition comprising an Flt4 binding compound, under conditions wherein the compound will bind to Flt4 in the biological sample; (b) washing the biological sample under conditions that will remove Flt4 binding compound that is not bound to Flt4 in the sample; and (c) screening the sample for the presence of Flt4 by detecting Flt4 binding compound bound to Flt4 receptor tyrosine kinase in the sample after the washing step. Preferably, the compound comprises a polypeptide selected from the group consisting of: (a) a polypeptide comprising an antigen-binding fragment of an anti-Flt4 antibody; and (b) a polypeptide comprising an Flt4 ligand or Flt4 binding fragment or analog thereof. Antibodies that specifically bind Flt4, and that further comprise a detectable label, are highly preferred.

The invention also is directed to a method for imaging vertebrate tissue suspected of containing cells that express Flt4 receptor tyrosine kinase protein (Flt4), comprising the steps of: (a) contacting vertebrate tissue with a composition comprising an Flt4 binding compound; and (b) imaging the tissue by detecting the Flt4 binding compound bound to the tissue. Preferably, the tissue is human tissue, and the method further comprises the step of washing the tissue, after the contacting step and before the imaging step, under conditions that remove from the tissue Flt4 compound that is not bound to Flt4 in the tissue.

In a related variation, the invention provides a method for imaging tumors in tissue from a vertebrate organism, comprising the steps of: (a) contacting vertebrate tissue suspected of containing a tumor with a composition comprising an Flt4 binding compound; (b) detecting the Flt4 binding compound bound to cells in said tissue; and (c) imaging solid tumors by identifying blood vessel endothelial cells bound by the Flt4 binding compound, wherein blood vessels expressing Flt4 are correlated with the presence and location of a tumor in the tissue. In one preferred embodiment, the method further comprises steps of contacting the tissue with a second compound (such as an antibody) that specifically binds to a blood vessel endothelial marker (e.g., PAL-E, VEGFR-1, VEGFR-2) that is substantially absent in lymphatic endothelia; and detecting the second compound bound to cells in the tissue; wherein the imaging step comprises identifying blood vessels labeled with both the Flt4 binding compound and the second compound, and wherein blood vessels labeled with both the Flt4 binding compound and the second compound correlate with the presence and location of a tumor in the tissue. It will be appreciated that the use of the second compound helps the practitioner to more rapidly distinguish between blood vessels that are expressing Flt4 and normal lymphatic vessels which express Flt4 on their surface.

The invention is further directed to a method of screening for a neoplastic disease state, comprising the steps of: (a) contacting tissue from a mammalian organism suspected of having a neoplastic disease state with a composition comprising an antibody or antibody fragment that specifically binds Flt4 receptor tyrosine kinase; (b) detecting the antibody or antibody fragment bound to cells in the mammalian organism; and (c) screening for a neoplastic disease from the quantity or distribution of the antibody bound to cells in the mammalian organism. As described herein, Flt4 (which usually is undetectable or barely detectable in the blood vasculature) is strongly stained in the blood vasculature of at least some tumors. Thus, in one embodiment, in the screening step, the detection of the antibody or antibody fragment bound to blood vessel endothelial cells is correlated with the presence of a neoplastic disease. In this method, it will be understood that "detection" means detection at a level significantly higher than the barely detectable or undetectable levels that would occur in corresponding normal (healthy) tissue, as described herein. Such differential expression can be confirmed by comparison to a control performed with tissue from a healthy organism. Screening mammary tissue for neoplasms is specifically contemplated. As described above, the practice of such methods may be further facilitated by the administering to said mammal of a second compound that specifically binds to a blood vessel endothelial marker, wherein the detecting step comprises detection of said first and said second compound bound to neovascular endothelial cells.

From the foregoing it will further be appreciated that the various compounds described for use in methods of the invention also are intended as aspects of the invention. Such compounds include the anti-Flt4 antibodies and bi-specific antibodies described above, for example. Likewise, the use of any compounds described herein (alone or in combination) for the manufacture of a medicament for therapeutic or diagnostic or imaging purposes described herein also is intended as an aspect of the invention. The medicament may further comprise pharmaceutically acceptable diluents, adjuvants, carriers, or the like.

Similarly, the invention includes kits which comprise compounds or compositions of the invention packaged in a manner which facilitates there use to practice methods of the invention. In a simplest embodiment, such a kit includes a compound or composition of the invention packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes a Flt4 binding compound packaged together with a second compound that binds to a marker (antigen) that is expressed on the surface of blood vessel endothelial cells but is substantially absent from lymphatic endothelia.

Additionally, many aspects of the invention have been described in the context of using peptides or polypeptides for imaging or therapy, and/or for using Flt4 protein expression on cell surfaces as a target for detection, screening, imaging, or the like, using antibodies. The therapeutic delivery of protein therapeutics, such as polypeptides comprising ligand-binding soluble Flt4 fragments, can also be accomplished with gene therapy materials and methods. For example, a naked DNA constrict or gene therapy expression vector construct comprising a polynucleotide encoding the therapeutic peptide of interest is delivered to a mammalian subject in need of therapy. Preferably, the construct comprises a promoter or other expression control sequence operatively linked to the sequence encoding the therapeutic peptide, to promote expression of the therapeutic peptide in vivo. In one variation, the nucleic acid is encapsulated in a liposome. In another variation, the nucleic acid is a viral vector such as a retrovirus, adenovirus, adeno-associated virus, vaccinia virus, herpesvirus, or other vector developed for gene therapy protocols in mammals. Exemplary treatment methods include steps of administering a pharmaceutical composition comprising the gene therapy construct to a patient, or a step of transforming or transfecting cells ex vivo and introducing the transformed cells into the patient. Similarly, the detection of Flt4 expression by cells or tissues can be performed using polynucleotide probes that will specifically hybridize to Flt4 mRNA sequences in Northern hybridization or in situ hybridization assays; or by performing quantitative PCR or other techniques to measure Flt4 mRNA in samples.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIGS. 2A-F present a schematic depiction of structural features of Flt4 and a comparison with the Flt1 tyrosine kinase sequence;

FIGS. 5A-5H depict immunohistochemical characterization of VEGFR-3-expressing vessels in intraductal carcinoma. In adjacent sections (FIGS. 5A, B), VEGFR-3 and PAL-E decorate a similar pattern of "necklace" vessels (arrowheads) around the duct filled with carcinoma cells. Another set of adjacent sections was compared with staining for VEGFR-3 (FIG. 5C), laminin (FIG. 5D), collagen XVIII (FIG. 5E) and SMA (FIG. 5F). Double staining for PAL-E and VEGFR-3 (FIG. 5G) and comparison with adjacent section stained for VEGFR-3 only (FIG. 5H). The vessels adjacent to the affected ducts are double-positive (arrowheads), whereas a VEGFR-3 positive vessel is present a short distance away from the affected duct in the interductal stroma (arrows). Note that basal lamina is positive for PAL-E in the double staining procedure. Magnifications: FIGS. 5A,B 400×. FIGS. 5C, D, E, F 320×. FIGS. 5E,F 480×.

DETAILED DESCRIPTION

Figure 1A:
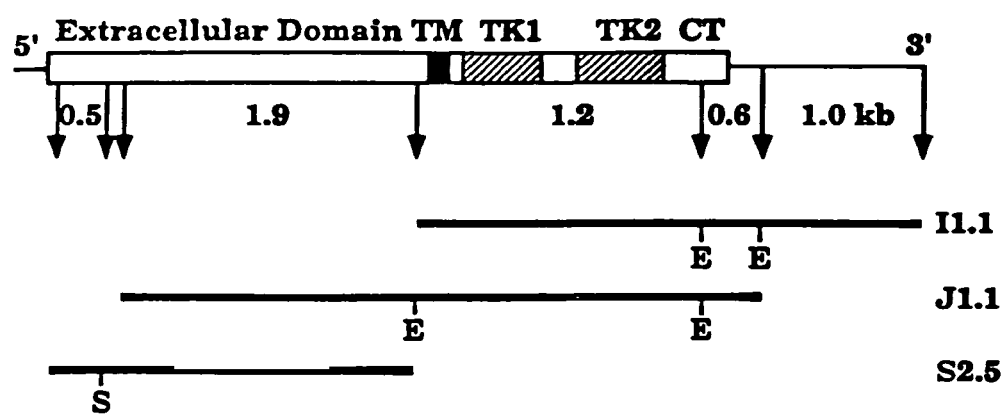
FIG. 1A is a schematic depiction of the structure of Flt4 cDNA clones.

The cloning, sequencing and expression of a novel receptor tyrosine kinase, termed Flt4, is described below. The Flt4 gene maps to chromosomal region 5q35 where many growth factors and growth factor receptors are located. The extracellular domain of Flt4 consists of seven immunoglobulin-like loops including twelve potential glycosylation sites. On the basis of structural similarities, Flt4 and the previously known Flt1 and KDR/FLK1 receptors may constitute a subfamily of class III tyrosine kinases. The Flt4 gene is expressed as 5.8 kb and 4.5 kb mRNAs which were found to differ in their 3' sequences and to be differentially expressed in HEL and DAMI leukemia cells.

A Wilm's tumor cell line, a retinoblastoma cell line, and a nondifferentiated teratocarcinoma cell line expressed Flt4; whereas differentiated teratocarcinoma cells were negative. Most fetal tissues also expressed the Flt4 mRNA, with spleen, brain intermediate zone and lung showing the highest levels. In human adult tissues the highest expression level was found in placenta, lung, kidney, heart and liver in decreasing order of expression. In in situ hybridization, the Flt4 autoradiographic grains decorated endothelial cells of fetal lung. Immunohistochemical staining of Flt4 in fetal tissues confirmed staining of the endothelial cells. The expression pattern of Flt4 in comparison to Flt1 and KDR differs greatly in tissues of 18-week-old human fetuses. See Kaipainen et al., *J. Exp. Med.*, 178:2077 (1993).

Expression vectors containing the Flt4 cDNA have been produced and expressed in COS and NIH3T3 cells as described in Examples 4 and 11.

The Flt4 DNAs and polypeptides of the invention may be useful in the purification of the Flt4 ligand, and in the regulation of growth and differentiation of endothelial cells in various organs. They may also prove valuable in the diagnosis/treatment of certain diseases.

In the description that follows, a number of terms used in recombinant DNA (rDNA) technology are extensively utilized. In order to provide a clear and consistent understanding of the specification and claims, including the scope to be given to such terms, the following definitions are provided.

Gene. A DNA sequence containing a template for a RNA polymerase. The RNA transcribed from a gene may or may not code for a protein. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA lacking intervening sequences (introns).

Cloning vehicle. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression vector. A vehicle or vector similar to a cloning vehicle and which is capable of expressing a gene which has been cloned into it, after transformation into a host. The cloned gene is usually placed under the control of (i.e., operably linked to) certain control sequences such as promoter sequences. Expression control sequences vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

The present invention pertains to both expression of recombinant Flt4 proteins (short and long forms), and to the functional derivatives of these proteins.

Functional Derivative. A "functional derivative" of Flt4 proteins is a protein which possesses a biological activity (either functional or structural) that is substantially similar to a biological activity of non-recombinant Flt4 proteins. A functional derivative of the Flt4 protein may or may not contain post-translational modifications such as covalently linked carbohydrate, depending on the necessity of such modifications for the performance of a specific function. The term "functional derivative" is intended to include the "fragments," "variants," "analogues," and "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art.

Fragment. A "fragment" of a molecule such as Flt4 protein is meant to refer to any portion of the molecule, such as the peptide core, or a variant of the peptide core.

Variant. A "variant" of a molecule such as Flt4 protein is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

Analogue. An "analogue" of Flt4 protein or genetic sequence is meant to refer to a protein or genetic sequence substantially similar in function to the Flt4 protein or genetic sequence herein.

DESCRIPTION OF PREFERRED EMBODIMENTS

The present invention is directed to what applicants have termed "Flt4," a receptor for tyrosine kinase, Flt4-encoding nucleic acid molecules (e.g. cDNAs, genomic DNAs, RNAs, anti-sense RNAs, etc.), production of Flt4 peptides or Flt4 protein from a Flt4 gene sequence and its product, recombinant Flt4 expression vectors, Flt4 analogues and derivatives, and diagnostic and/or therapeutic uses of Flt4 and related proteins, Flt4 ligands, Flt4 antagonists and anti-Flt4 antibodies.

Production of Recombinant Flt4

Biologically active Flt4 may be produced by the cloning and expression of the Flt4-encoding sequence or its functional equivalent in a suitable host cell.

Production of Flt4 using recombinant DNA technology may be divided into a step-wise process for the purpose of description: (1) isolating or generating the coding sequence (gene) for the desired Flt4; (2) constructing an expression vector capable of directing the synthesis of the desired Flt4; (3) transfecting or transforming appropriate host cells capable of replicating and expressing the Flt4 gene and/or processing the gene product to produce the desired Flt4; and (4) identifying and purifying the desired Flt4 product.

Isolation or Generation of the Flt4 Gene

The nucleotide coding sequence of Flt4 or functional equivalents thereof, may be used to construct recombinant expression vectors which will direct the expression of the desired Flt4 product. In the practice of the method of the invention, the nucleotide sequence depicted therein, or fragments or functional equivalents thereof, may be used to generate the recombinant molecules which will direct the expression of the recombinant Flt4 product in appropriate host cells. Flt4-encoding nucleotide sequences may be obtained from a variety of cell sources which produce Flt4-like activities and/or which express Flt4-encoding mRNA. Applicants have identified a number of suitable human cell sources for Flt4, including human placenta, leukemia cells and some tumor cell lines.

The Flt4 coding sequence may be obtained by cDNA cloning from RNA isolated and purified from such cell sources or by genomic cloning. The Flt4 sequence may be for example amplified by polymerase chain reaction from cDNA or genomic DNA material using techniques well known in the art. Either cDNA or genomic libraries of clones may be prepared using techniques well known in the art and may be screened for particular Flt4 DNAs with nucleotide probes which are substantially complementary to any portion of the Flt4 gene. Full length clones, i.e., those containing the entire coding region of the desired Flt4, may be selected for constructing expression vectors. Alternatively, Flt4 encoding DNAs may be synthesized in whole or in part by chemical synthesis using techniques standard in the art. Due to the inherent degeneracy of nucleotide coding sequences, other DNA sequences which encode substantially the same or a functionally equivalent amino acid sequence may be used in the practice of the method of the invention. Such alterations of Flt4 nucleotide sequences include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

Construction of Flt4 Expression Vectors

Using this information, a variety of recombinant DNA vectors capable of providing the Flt4 receptor tyrosine kinase in reasonable quantities are provided. Additional recombinant DNA vectors of related structure that code for synthetic proteins having the key structural features identified herein as well as for proteins of the same family from other sources can be produced from the Flt4 receptor tyrosine kinase cDNA using standard techniques of recombinant DNA technology. A transformant expressing the Flt4 receptor tyrosine kinase has been produced as an example of this technology (see EXAMPLES 3 and 4). The newly discovered sequence and structure information can be used, through transfection of eukaryotic cells, to prepare the Flt4 receptor tyrosine kinase and its various domains for biological purposes.

Identification of Transfectants or Transformants Expressing Flt4 Gene Products The host cells which contain the recombinant coding sequence and which express the biologically active, mature product may be identified by at least four general approaches: (a) DNA-DNA, DNA-RNA or RNA-antisense RNA hybridization; (b) the presence or absence of "marker" gene functions; (c) assessing the level of transcription as measured by the expression of Flt4 mRNA transcripts in the host cell; and (d) detection of the mature gene product as measured by immunoassay and, ultimately, by its biological activities.

In the first approach, the presence of Flt4 coding sequences inserted into expression vectors may be detected by DNA-DNA hybridization using probes comprising nucleotide sequences that are homologous to the Flt4 coding sequence.

In the second approach, the recombinant expression vector/host system may be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Flt4 coding sequence is inserted within a marker gene sequence of the vector, recombinants containing that coding sequence can be identified by the absence of the marker gene function. Alternatively, a marker gene can be placed in tandem with the Flt4 sequence under the control of the same or different promoter used to control the expression of the Flt4 coding sequence. Expression of the marker in response to induction or selection indicates expression of the Flt4 coding sequence.

In the third approach, transcriptional activity for the Flt4 coding region may be assessed by hybridization assays. For example, polyadenylated RNA can be isolated and analyzed by Northern blotting using a probe homologous to the Flt4 coding sequence or particular portions thereof. Alternatively, total nucleic acids of the host cell may be extracted and assayed for hybridization to such probes.

In the fourth approach, the expression of Flt4 can be assessed immunologically, for example by Western blots, immunoassays such as radioimmunoprecipitation, enzyme-linked immunoassays and the like. The ultimate test of the success of the expression system, however, involves the detection of the biologically active Flt4 gene product. Where the host cell secretes the gene product, the cell free media obtained from the cultured transfectant host cell may be assayed for Flt4 activity. Where the gene product is not secreted, cell lysates may be assayed for such activity. In either case, assays which measure ligand binding to Flt4 or other bioactivities of Flt4 may be used.

Flt4 Derivatives, Analogues and Peptides

The production and use of derivatives, analogues, and peptides related to Flt4 are also envisioned and are within the scope of the invention. Such derivatives, analogues, or peptides may have enhanced or diminished biological activities in comparison to native Flt4, depending on the particular application. Flt4 related derivatives, analogues, and peptides of the invention may be produced by a variety of means known in the art. Procedures and manipulations at the genetic and protein levels are within the scope of the invention. Peptide synthesis, which is standard in the art, may be used to obtain Flt4 peptides. At the protein level, numerous chemical modifications may used to produce Flt4-like derivatives, analogues, or peptides by techniques known in the art, including but not limited to specific chemical cleavage by endopeptidases (e.g. cyanogen bromides, trypsin, chymotrypsin, V8 protease, and the like) or exopeptidases, acetylation, formylation, oxidation, etc.

Preferred derivatives, analogs, and peptides are those which retain Flt4 ligand binding activity. Those derivatives, analogs, and peptides which bind Flt4 ligand but do not transduce a signal in response thereto are useful as Flt4 inhibitors. Those derivatives, analogs, and peptides which bind Flt4 ligand and transduce a signal in response thereto, e.g., through a process involving intracellular Flt4 autophosphorylation, are useful in the same manner as native Flt4. A preferred Flt4 ligand for use in such binding and/or autophosphorylation assays is a ligand comprising an approximately 23 kd polypeptide that is isolatable from a PC-3 conditioned medium as described herein. This ligand, designated Vascular Endothelial Growth Factor-C (VEGF-C), has been characterized in detail in PCT Patent Application PCT/FI96/00427, filed Aug. 1, 1996, and published as International Publication WO 97/05250, and in the U.S. patent application priority documents relied upon therein for priority, all of which are incorporated herein by reference in their entirety.

Anti-Flt4 Antibodies

Also within the scope of the invention is the production of polyclonal and monoclonal antibodies which recognize Flt4 or related proteins.

Various procedures known in the art may be used for the production of polyclonal antibodies to epitopes of Flt4. For the production of antibodies, various host animals (including but not limited to rabbits, mice, rats, etc.) can be immunized by injection with Flt4, or a synthetic Flt4 peptide. Various adjuvants may be used to increase the immunological response, depending on the host species, including but not limited to Freund's (complete and incomplete) adjuvant, mineral gels such as aluminium hydroxide, surface active substances such as lysolecithin, pluronic polyols, polyanions, oil emulsions, keyhole limpet hemocyanins, dinitrophenol, and potentially useful human adjuvants such as BCG (*Bacillus Calmette-Guerin*) and *Corynebacterium parvum*.

A monoclonal antibody to an epitope of Flt4 may be prepared by using any technique which provides for the production of antibody molecules by continuous cell lines in culture. These include but are not limited to the hybridoma technique originally described by Köhler et al., *Nature*, 256: 495-497 (1975), and the more recent human B-cell hybridoma technique [Kosbor et al., *Immunology Today*, 4: 72 (1983)] and the EBV-hybridoma technique [Cole et al., *Monoclonal Antibodies and Cancer Therapy*, Alan R Liss, Inc., pp. 77-96 (1985)]. Antibodies against Flt4 also may be produced in bacteria from cloned immunoglobulin cDNAs. With the use of the recombinant phage antibody system it may be possible to quickly produce and select antibodies in bacterial cultures and to genetically manipulate their structure.

Antibody fragments which contain the idiotype of the molecule may be generated by known techniques. For example, such fragments include but are not limited to: the $F(ab')_2$ fragment which may be produced by pepsin digestion of the antibody molecule; the Fab' fragments which may be generated by reducing the disulfide bridges of the $F(ab')_2$ fragment, and the two Fab fragments which may be generated by treating the antibody molecule with papain and a reducing agent.

Antibodies to Flt4 may be used in the qualitative and quantitative detection of mature Flt4 and Flt4 precursor and subcomponent forms, in the affinity purification of Flt4 polypeptides, and in the elucidation of Flt4 biosynthesis, metabolism and function. Detection of Flt4 tyrosine kinase activity may be used as an enzymatic means of generating and amplifying a Flt4 specific signal in such assays. Antibodies to Flt4 may also be useful as diagnostic and therapeutic agents.

Uses of Flt4, Flt4-Encoding Nucleic Acid Molecules, and Anti-Flt4 Antibodies

Applicants envision a wide variety of uses for the compositions of the present invention, including diagnostic and/or therapeutic uses of Flt4, Flt4 analogues and derivatives, Flt4-encoding nucleic acid molecules, antisense nucleic acid molecules and anti-Flt4 antibodies.

Flt4-encoding nucleic acid molecules or fragments thereof may be used as probes to detect and quantify mRNAs encoding Flt4. Assays which utilize nucleic acid probes to detect sequences comprising all or part of a known gene sequence are well known in the art. Flt4 mRNA levels may indicate emerging and/or existing neoplasias as well as the onset and/or progression of other human diseases. Therefore, assays which can detect and quantify Flt4 mRNA may provide a valuable diagnostic tool.

Anti-sense Flt4 RNA molecules are useful therapeutically to inhibit the translation of Flt4-encoding mRNAs where the therapeutic objective involves a desire to eliminate the presence of Flt4 or to downregulate its levels. Flt4 anti-sense RNA, for example, could be useful as a Flt4 antagonizing agent in the treatment of diseases in which Flt4 is involved as a causative agent, for example due to its overexpression.

Additionally, Flt4 anti-sense RNAs are useful in elucidating Flt4 functional mechanisms. Flt4-encoding nucleic acid molecules may be used for the production of recombinant Flt4 proteins and related molecules as separately discussed in this application.

Anti-Flt4 antibodies may be used to diagnose and quantify Flt4 in various contexts. For example, antibodies against various domains of Flt4 may be used as a basis for Flt4 immunoassays or immunohistochemical assessment of Flt4. Tyrosine kinase activity of Flt4 may be useful in these assays as an enzymatic amplification reaction for the generation of a Flt4 signal. Anti-Flt4 antibodies may also be useful in studying the amount of Flt4 on cell surfaces.

Antibodies may be produced which function as Flt4 ligand agonists or antagonists whereby the regulation of Flt4 activity becomes possible. Also, random peptides may be produced by synthetic means or by recombinant means from random oligonucleotides and the ones showing specific binding to the Flt4 receptor may be selected with the aid of the Flt4 extracellular domain. Such peptide segments also may be selected from a phage display library using the extracellular domain of Flt4, using methods standard in the art. Such peptides may have agonistic or antagonistic activity. Flt4 antibodies may also provide valuable diagnostic tools after conjugation to various compounds for in vivo imaging of Flt4 expressing cells and tissues or tumors.

Monoclonal antibodies against Flt4 may be coupled either covalently or noncovalently to a suitable supramagnetic, paramagnetic, electron-dense, echogenic or radioactive agent to produce a targeted imaging agent. Antibody fragments generated by proteolysis or chemical treatments or molecules produced by using the epitope binding domains of the monoclonal antibodies could be substituted for the intact antibody. This imaging agent would then serve as a contrast reagent for X-ray, magnetic resonance, sonographic or scintigraphic imaging of the human body for diagnostic purposes.

Molecular Biology of Flt4

The complete sequences of the Flt4 cDNA clones set forth in SEQ ID NOs: 1 and 3 extend for 4195 or 4795 nucleotides and contain open reading frames of 1298 or 1363 amino acids, depending on alternative splicing. The nucleotide and deduced Flt4 amino acid sequence (short form) is shown in SEQ ID NOs: 1 and 2. FIG. 2 depicts a comparison of the Flt4 amino acid sequence with that of the Flt4 tyrosine kinase amino acid sequence. See Shibuya et al., *Oncogene.* 5: 519-524 (1990).

A putative signal peptide sequence of mostly hydrophobic amino acids follows the initiator methionine. The sequence surrounding the corresponding ATG is in agreement with the consensus translation initiation sequence [Kozak, *Nucl. Acids Res.*, 15: 8125-8135 (1987)]. The predicted extracellular portion of both Flt4 polypeptides is 775 amino acids long and contains twelve potential sites for asparagine-linked glycosylation (NXS/T). It also contains several amino acid residues exhibiting a pattern of spacing described for members of the immunoglobulin superfamily of proteins [Williams et al., *Annu. Rev. Immunol.*, 6: 381-405 (1988)]. It has 12 cysteine residues and it can be organized in seven immunoglobulin-like domains. As shown in FIG. 2, the seven immunoglobulin-like domains are defined approximately as follows: Ig-I (SEQ ID NO: 1, positions 158-364; SEQ ID NO: 2, amino acids 47-115); Ig-II (SEQ ID NO: 1, positions 479-649; SEQ ID NO: 2, amino acids 154-210); Ig-III (SEQ ID NO: 1, positions 761-961; SEQ ID NO: 2, amino acids 248-314); Ig-IV (SEQ ID NO: 1, positions 1070-1228; SEQ ID NO: 2, amino acids 351-403); Ig-V (SEQ ID NO: 1, positions 1340-1633; SEQ ID NO: 2, amino acids 441-538); Ig-VI (SEQ ID NO: 1, positions 1739-1990; SEQ ID NO: 2, amino acids 574-657); and (SEQ ID NO: 1, positions 2102-2275; SEQ ID NO: 2, amino acids 695-752). The predicted Ig-like domain IV lacks cysteine residues. FIG. 2 also shows the extracellular domain of Flt1 (SEQ. ID No. 5), which is the closest human homologue of Flt4. From this figure one can see the alignment of the cysteine residues and the very similar composition of the Ig-like regions.

The cytoplasmic domain of Flt4 is separated from the extracellular part by a putative transmembrane region of 23 hydrophobic amino acid residues. This sequence is flanked on the cytoplasmic side by a basic region suggesting the junction between the transmembrane and cytoplasmic domains. The tyrosine kinase homologous domain begins at residue 843 and includes an ATP-binding pocket and a putative autophosphorylation site homologous to Y416 of c-src at Y1068 (FIG. 2). The tyrosine kinase catalytic domain of Flt4 is divided into two subdomains by a 65 amino acid sequence (aa 944-1008) which is mostly hydrophilic and does not show homology to Flt1. Unlike Flt1, Flt4 does not contain tyrosine residues in its kinase insert.

A second species of Flt4 mRNA has an alternative 3' end which encodes a longer form of the Flt4 protein.

Figure 3A:
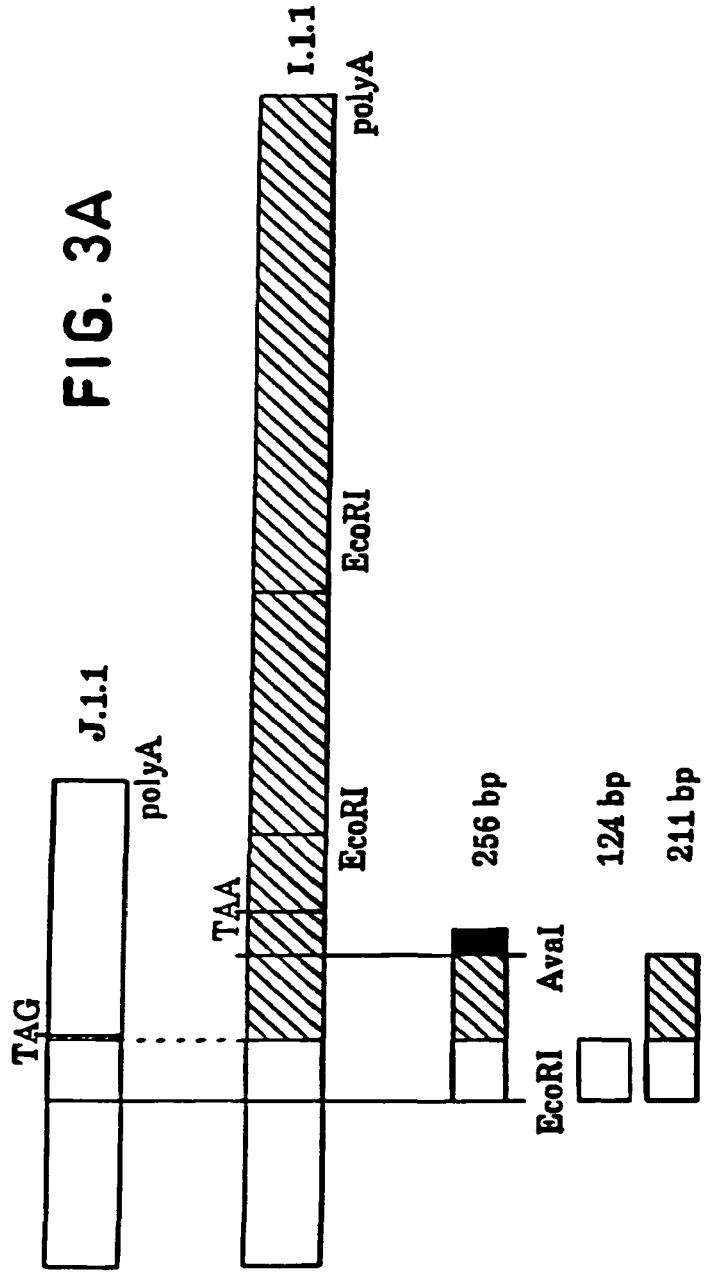
FIG. 3A is a schematic depiction of the 3' ends of the cDNA inserts of clones J.1.1 and I.1.1.
Figure 3B:
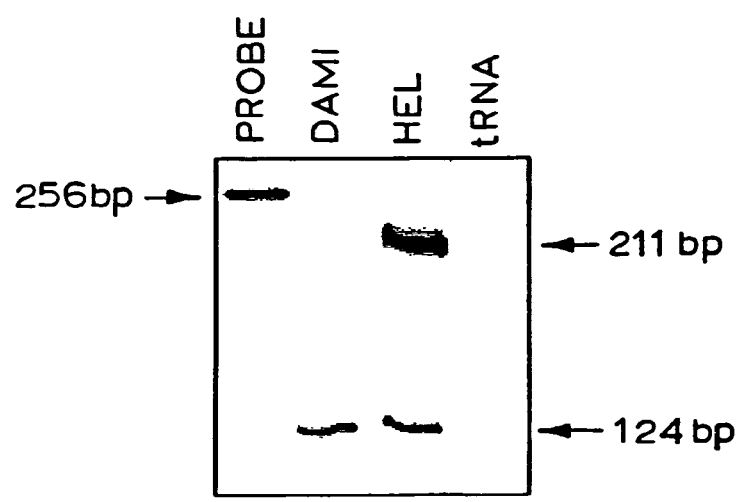
FIG. 3B is a photographic reproduction of autoradiograms of hybridizations with anti-sense RNA probe and the long and short forms of Flt4 RNA.
Figure 3C:
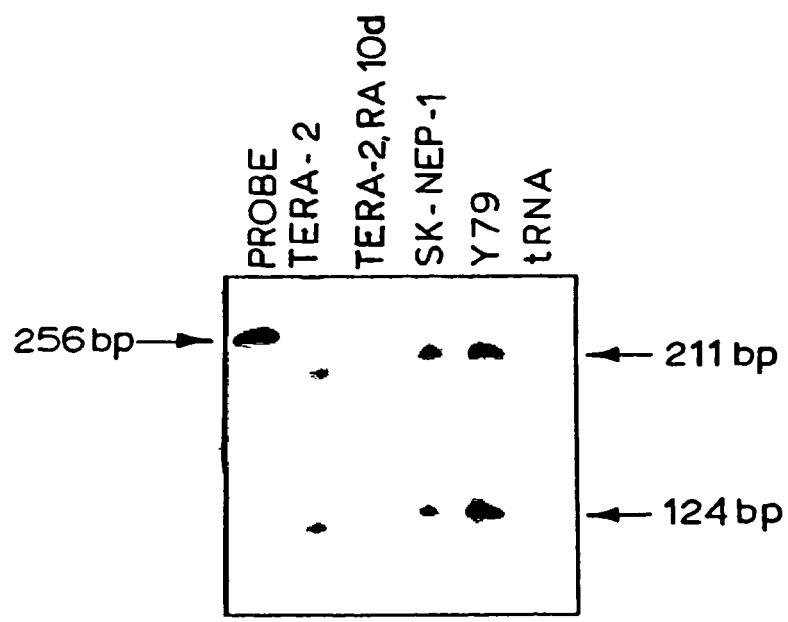
FIG. 3C is a photographic reproduction of autoradiograms of hybridizations with anti-sense RNA probe and the long and short forms of Flt4 RNA.

In FIGS. 3A-C, production of short and long forms of the Flt4 mRNA by alternative splicing is illustrated. FIG. 3A shows the schematic structure of the 3' ends of the cDNA inserts of clones J.1.1 and I.1.1. The TAG stop codon of clone J.1.1 as well as the polyadenylation site (polyA) are indicated. Clone I.1.1 differs from clone J.1.1 in the shaded segment (the long and short forms of Flt4 mRNA, respectively). TAA and polyA indicate the stop codon and polyadenylation site of clone I.1.1. In addition, the restriction endonuclease cleavage sites for EcoRI and AvaI have been indicated. Shown below is the 256 bp EcoRI-AvaI insert of clone I.1.1. used for cRNA protection analysis. The most heavily-shaded segment indicates sequences from the polylinker in the linearized sense RNA template for transcription of the antisense strand in vitro. Also shown are the schematic structures of the protected fragments after RNAse protection analysis. FIGS. 3B and 3C, show autoradiograms of the 256 bp $^{35}$S-labeled antisense RNA probe and the 211 and 124 bp digested fragments representing the long and short forms of Flt4 RNA when protected by polyadenylated RNA from the indicated cell lines (Tera-2 is a teratocarcinoma cell line, which has been analyzed here with or without retinoic acid (RA) treatment for 10 days.) The (negative) control lane shows results of protection with transfer RNA. Note the downregulation of Flt4 mRNAs during the differentiation of the Tera-2 cells. Tera-2 cells of clone 13 were provided by Dr. C. F. Graham (Department of Zoology, University of Oxford, UK). Cells between passages 18-40 were used in this study. The cells were maintained in Eagle's minimum essential medium (MEM) supplemented with 10% fetal calf serum and antibiotics. To induce differentiation, the cells were plated on gelatin-coated tissue-culture grade dishes at a density of $1.5 \times 10^3$ cells/cm$^2$. On the following day, $2 \times 10^{-6}$ M RA was added to the medium. The cells were cultured in the presence of RA for up to 10 days.

Results shown in FIGS. 3A-C illustrate the generation of carboxy termini of these two Flt4 (short and long) forms generated by alternative splicing.

According to its deduced amino acid sequence, Flt4 belongs to class III RTKs. More specifically, Flt4 belongs to a subfamily of RTKs, which contain seven Ig-loops in their extracellular part and thus it differs from other members of class III RTKs which contain five Ig-loops. Flt4 is most closely homologous with the prototype receptor of the FLT family, Flt1, which was cloned as a v-ros-related DNA from a human genomic DNA library [Shibuya et al., Oncogene, 5: 519-524 (1990)] and with the mouse FLK1 receptor, which was cloned from hematopoietic stem cell-enriched fractions of mouse liver [Matthews et al., Cell, 65: 1143-1152 (1991); Matthews et al., Proc. Natl. Acad. Sci. USA, 88: 9026-9030 (1991)]. The extracellular domain of Flt4 shows 33% and 37% amino acid sequence identity with human Flt4 and mouse FLK1, respectively. Flt1 and FLK1, like Flt4, are widely expressed in various normal tissues, such as lung, heart, and kidney. In addition, a recently identified human endothelial cell receptor tyrosine kinase KDR [Terman et al., Oncogene, 6: 1677-1683 (1991)] shows considerable homology with Flt4 and Flt1 family members. From the available sequence data one may calculate that KDR is 81% identical with Flt4 in the tyrosine kinase (TK) domain. In addition, the extracellular domain of KDR also has a seven Ig-loop structure and its TK1 and TK2 domains are 95% and 97% identical with the corresponding domains of mouse FLK1 receptor. This suggests that KDR is the human homologue of mouse FLK1.

While the Flt4 TK domain is about 80% identical with the TK domains of Flt1 and FLK1/KDR, it is only about 60% identical with the TK domains of other receptors of the RTK class III. As these other receptors also have only five Ig-like domains in the extracellular region, one can classify Flt4, Flt1 and FLK1/KDR in a separate FLT subfamily within class III RTKs.

The tyrosine residue located in the sequence D/E-D/E-Y-M/V-P/D/E-M [Cantley, et al., Cell, 64: 281-302 (1991)] (SEQ. ID NO. 6) in kinase inserts of PDGFRs, c-fms and c-kit is an autophosphorylation site, which, when phosphorylated, binds the SH2 domain of phosphatidylinositol 3'-kinase (PI-3K) [Reedijk et al., EMBO J., 11: 1365-1372 (1992)]. Interestingly, unlike these class III RTKs, members of the FLT subfamily or the Flt3/FLK2 receptor do not contain such consensus motifs.

The eight human class III RTK genes are clustered in three different chromosomes. Chromosome 4 contains the c-kit, PDGFR-α and KDR genes [Yarden et al., EMBO J., 6: 3341-3351 (1987); Stenman et al., Genes, Chromosomes, Cancer, 1: 155-158 (1989); Terman et al., Oncogene, 6: 1677-1683 (1991)]. The Flt1 and Flt3 genes are located in chromosome 13q12 [Satoh et al., Jpn. J. Cancer Res., 78: 772-775 (1987); Rosnet et al., Genomics, 9: 380-385 (1991)], while Flt4 is localized in chromosome 5 band q35 [Aprelikova et al., Cancer Res., 52: 746-748 (1992)]; close to the fms and PDGFR-β genes [Warrington et al., Genomics, 11: 701-708 (1991). The long arm of chromosome 5 is involved in translocations found in leukemia cells. Deletions of part of the long arm of chromosome 5 were found in the bone marrow cells of patients with refractory anemia and macrocytosis [Van Den Berghe et al., Nature, 251: 437-439 (1974)]. An abnormal 5q chromosome is found in a few other myeloproliferative diseases, such as refractory anemia with excess blasts [Swolin et al., Blood, 58: 986-993 (1981)], agnogenic myeloid metaplasia [Whang-Peng et al., Leuk. Res., 2: 41-48 (1978)], chronic myelogenous leukemia [Tomiyasu et al., Cancer Genet. Cytogenet., 2: 309-315 (1980)], polycythemia vera [Van Den Berghe et al., Cancer Genet. Cytogenet., 1: 157-162 (1979)] and essential thrombocythemia [Nowell et al., Cancer, 42: 2254-2260 (1978)].

The findings on Flt4 mRNA expression suggest that its protein product is characteristic for certain leukemia cells. Several differentiation antigens shared between megakaryoblastic and endothelial cells have been shown to exist, one example being the platelet glycoprotein IIIa [Ylänne et al., Blood, 72: 1478-1486 (1988); Kieffer et al., Blood, 72: 1209-1215 (1988); Berridge et al., Blood, 66: 76-85 (1985)]. In addition, Flt4 is expressed by certain endothelial cells of, e.g., the lung and kidney during the fetal period.

To further understand the role of Flt4 during development, partial cDNAs for mouse Flt4 were cloned. Using these probes in in situ hybridization, Flt4 mRNA expression during mouse development was analyzed. It was determined that Flt4 is expressed during vasculogenesis and angiogenesis of the lymphatic system. The relevance of these findings was also confirmed in normal and pathological human adult tissues, as Flt4 was found in lymphatic endothelial cells of human adult tissues both in normal and pathological conditions, as well as in some high endothelial venules (HEVs).

The cloning of mouse Flt4 cDNA fragments showed that their deduced amino acid sequence is almost identical with the corresponding human sequence (amino acid identity about 96% in both segments studied). Further evidence for the identity of the mouse Flt4 cDNA was obtained from Northern hybridization studies, wherein probes from both species yielded the typical 5.8 kb mRNA signal from mouse tissues. Analysis of RNA isolated from various tissues of adult mice showed Flt4 expression in the liver, lung, heart, spleen and kidney, with no or very little hybridization in the brain and testes. This pattern is similar to the pattern reported earlier by Galland et al., Oncogene, 8: 1233 (1993). The results of RNase protection suggested that the Flt4 gene is needed during mouse development, starting from 8.5 day p.c. embryos, and the relative expression levels appeared quite stable.

For the in situ hybridization, two fragments of mouse Flt4 cDNA were selected which encode sequences of the extracellular domain. This allowed a clear distinction of the hybridization pattern from the related FLK-1 and Flt1 receptor patterns, which show only a very low degree of sequence identity with Flt1 in the extracellular region. See Millauer et al., Cell, 72: 835 (1993); Yamaguchi et al., Development, 118:489 (1993); Peters et al., Proc. Natl. Acad. Sci. USA, 90: 8915 (1993); Finnerty et al., Oncogene, 8: 2293 (1993).

Flt4, similar to the FLK-1, Flt1, Tie and Tek endothelial receptor tyrosine kinase genes, was not expressed in 7.5 day post-coitum (p.c.) embryos. In a 8.5-day p.c. embryo, the strongest Flt4 signals were localised in the allantois, the angioblasts of head mesenchyme, the dorsal aortae, and the cardinal vein. Weak signals were seen in the endocardium. In contrast, angioblasts of the yolk sac were negative, unlike for FLK-1 and Flt1, Tie and Tek. See Korhonen et al., Oncogene.

8: 395 (1993); and Peters et al., *Proc. Natl. Acad. Sci. USA*, 90: 8915 (1993). The restriction of Flt4 expression to the venous system was even more clear in samples from 11.5 day mouse embryos, where the Tie mRNA was expressed only in arteries. In 12.5-day p.c. embryos the Flt4 signal decorated developing venous and presumptive lymphatic endothelia, but unlike for the endothelial Tie receptor tyrosine kinase, arterial endothelia were negative. During later stages of development, Flt4 mRNA became restricted to vascular plexuses devoid of blood cells, representing developing lymphatic vessels. Only the lymphatic-endothelium and some high endothelial venules expressed Flt4 mRNA in adult human tissues. Increased expression occurred in lymphatic sinuses and high endothelial venules, in metastatic lymph nodes, and in lymphangioma.

Due to difficulties in the interpretation of data from mouse embryos, human endothelia were studied, because the lymphatic system is much better defined in humans. Also, cells established from various endothelia could be studied in cell culture to see if the specificity of Flt4 expression persists in in vitro conditions. Endothelial cells lines are known to lose differentiated features upon in vitro culture. Therefore, it was not unexpected that they were negative for Flt4 mRNA. Cultured aortic endothelial cells were also devoid of Flt4 mRNA. However, signals were obtained from human endothelial cells grown from the microvasculature and from femoral and umbilical veins. Thus, at least some of the specificity of Flt4 expression was retained in cell culture.

In situ hybridization analysis of adult human tissues confirmed the restriction of Flt4 to the lymphatic system seen in the developing mouse embryos. Flt4 expression was seen in the lymphatic endothelia and in the sinuses of human lymph nodes. Interestingly, also some of the HEVs, which have a cuboidal endothelium, shown to function in the trafficking of leukocytes to the lymph nodes, were Flt4-positive. Furthermore, a parallel hybridization analysis showed that Flt4 mRNA levels were enhanced in these structures in metastatic as compared to normal lymph nodes. Flt4 was also very prominent in lymphangiomas, which are benign tumours composed of connective tissue stroma and growing, endothelial-lined lymphatic channels. Flt4 mRNA was restricted to the lymphatic endothelium of these tumors and absent, from their arteries, veins and capillaries. In the human lung, lymphatic structures were the only Flt4-positive vessels identified.

The foregoing results indicate that Flt4 is a novel marker for lymphatic vessels and some high endothelial venules in human adult tissues. The results also support the theory on the venous origin of lymphatic vessels. Flt4, as a growth factor receptor, may be involved in the differentiation and functions of these vessels. A detailed characterization of biological effects mediated through Flt4 via the Flt4 ligand, VEGF-C, is provided in PCT Patent Application PCT/FI96/00427, filed Aug. 1, 1996, and published as International Publication WO 97/05250.

These results, combined with the Flt4-binding compounds according to the present invention, allows a selective labeling of lymphatic endothelium, especially by using antibodies of the present invention coupled to radioactive, electron-dense or other reporter substances, which can be visualized. It may be possible to inject into the lymphatic system substances, containing Flt4 receptor internalization-inducing monoclonal antibodies or ligands, and thereby transport predefined molecules into the lymphatic endothelium. Also, it may be possible to use Flt4-binding compounds according to the invention for the detection of high endothelial venules, especially activated HEVs, which express enhanced levels of the Flt4 receptor. To our knowledge, no such specific markers are currently available for lymphatic endothelium.

Gene Based Therapies

The present invention also contemplates gene therapy methods. Specifically, the vasculature of the cancer cell or the cancer cell itself may be contacted with an expression construct capable of providing a therapeutic peptide, such as for example, the soluble VEGFR-3 fragments of the present invention, to the vasculature of the cell in a manner to effect a therapeutic outcome. Such a therapeutic outcome may be, for example, inhibition of VEGFR-3 in the vasculature of the tumor, an inhibition of angiogensis, an inhibition of lymphangiogenesis, an ablation, regression or other inhibition of tumor growth, an induction of apoptosis of the blood or lymphatic vasculature of the tumor or indeed the tumor cells themselves.

For these embodiments, an exemplary expression construct comprises a virus or engineered construct derived from a viral genome. The expression construct generally comprises a nucleic acid encoding the gene to be expressed and also additional regulatory regions that will effect the expression of the gene in the cell to which it is administered. Such regulatory regions include for example promoters, enhancers, polyadenylation signals and the like:

It is now widely recognized that DNA may be introduced into a cell using a variety of viral vectors. In such embodiments, expression constructs comprising viral vectors containing the genes of interest may be adenoviral (see for example, U.S. Pat. Nos. 5,824,544; 5,707,618; 5,693,509; 5,670,488; 5,585,362; each incorporated herein by reference), retroviral (see for example, U.S. Pat. Nos. 5,888,502 ; 5,830,725; 5,770,414; 5,686,278; 4,861,719 each incorporated herein by reference), adeno-associated viral (see for example, U.S. Pat. Nos. 5,474,935; 5,139,941; 5,622,856; 5,658,776; 5,773,289; 5,789,390; 5,834,441; 5,863,541; 5,851,521; 5,252,479 each incorporated herein by reference), an adenoviral-adenoassociated viral hybrid (see for example, U.S. Pat. No. 5,856,152 incorporated herein by reference) or a vaccinia viral or a herpesviral (see for example, U.S. Pat. Nos. 5,879,934; 5,849,571; 5,830,727; 5,661,033; 5,328,688 each incorporated herein by reference) vector.

In other embodiments, non-viral delivery is contemplated. These include calcium phosphate precipitation (Graham and Van Der Eb, *Virology*, 52:456-467, 1973; Chen and Okayama, *Mol. Cell. Biol.*, 7:2745-2752, 1987; Rippe et al., *Mol. Cell. Biol.*, 10:689-695, 1990) DEAE-dextran (Gopal, *Mol. Cell. Biol.*, 5:1188-1190, 1985), electroporation (Tur-Kaspa et al., *Mol. Cell. Biol.*, 6:716-718, 1986; Potter et al., *Proc. Nat. Acad. Sci. USA,* 81:7161-7165, 1984), direct microinjection (Harland and Weintraub, J. Cell Biol., 101:1094-1099, 1985.), DNA-loaded liposomes (Nicolau and Sene, *Biochim. Biophys. Acta*, 721:185-190, 1982; Fraley et al., *Proc. Natl. Acad. Sci. USA*, 76:3348-3352, 1979; Feigner, *Sci Am.* 276 (6):102-6, 1997; Feigner, *Hum Gene Ther.* 7(15):1791-3, 1996), cell sonication (Fechheimer et al., *Proc. Natl. Acad. Sci. USA*, 84:8463-8467, 1987), gene bombardment using high velocity microprojectiles (Yang et al., *Proc. Natl. Acad. Sci. USA*, 87:9568-9572, 1990), and receptor-mediated transfection (Wu and Wu, *J. Biol. Chem.*, 262:4429-4432, 1987; Wu and Wu, *Biochemistry*, 27:887-892, 1988; Wu and Wu, *Adv. Drug Delivery Rev.*, 12:159-167, 1993).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, *In: Liver diseases, targeted diagnosis and therapy using specific receptors and ligands*, Wu G, Wu C ed., New York: Marcel Dekker, pp. 87-104, 1991). The addition of DNA to cationic liposomes causes a topological transition from liposomes to optically birefringent liquid-crystalline condensed globules (Radler et al., *Science*, 275(5301):810-4, 1997). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagelutinating virus (HVJ). This has been shown to facilitate fusion with the cell membrane and promote cell entry of liposome-encapsulated DNA (Kaneda et al., *Science*, 243:375-378, 1989). In other embodiments, the liposome may be complexed or employed in conjunction with nuclear nonhistone chromosomal proteins (HMG-1) (Kato et al., *J. Biol. Chem.*, 266:3361-3364, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987, supra) and transferrin (Wagner et al., *Proc. Nat'l. Acad. Sci. USA*, 87(9):3410-3414, 1990). Recently, a synthetic neoglycoprotein, which recognizes the same receptor as ASOR, has been used as a gene delivery vehicle (Ferkol et al., *FASEB J.*, 7:1081-1091, 1993; Perales et al., *Proc. Natl. Acad. Sci., USA* 91:4086-4090, 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (*Methods Enzymol.*, 149:157-176, 1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky et al. (*Proc. Nat. Acad. Sci. USA*, 81:7529-7533, 1984) successfully injected polyomavirus DNA in the form of $CaPO_4$ precipitates into liver and spleen of adult and newborn mice demonstrating active viral replication and acute infection. Benvenisty and Neshif (*Proc. Nat. Acad. Sci. USA*, 83:9551-9555, 1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., *Nature*, 327:70-73, 1987). Several devices for accelerating small particles have been developed. One such device relies on a high voltage discharge to generate an electrical current, which in turn provides the motive force (Yang et al., *Proc. Natl. Acad. Sci. USA*, 87:9568-9572, 1990). The microprojectiles used have consisted of biologically inert substances such as tungsten or gold beads.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector or protein. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient; preferably, any tumor cells in the sample have been killed.

The following examples are given merely to illustrate the present invention and not in any way to limit its scope.

Example 1

Isolation and Characterization of cDNA Clones Encoding Flt4

Materials and Methods

An oligo-dT primed human HEL cell cDNA library in bacteriophage lambda gt11 [A kind gift from Dr. Mortimer Poncz, Childrens Hospital of Philadelphia, Pa.; Poncz et al., *Blood*, 69: 219-223 (1987)] was screened with a cDNA fragment PCR-amplified from the same library [Aprelikova et al., Cancer Res. 52: 746-748 (1992)]. Positive plaques were identified and purified as described [Sambrook et al., *Molecular Cloning—A Laboratory Manual*, Cold Spring Harbor Laboratory Press, (1989)]. cDNA inserts of bacteriophage lambda were isolated as EcoRI fragments and subcloned into a GEM3Zf(+) plasmid (Promega). The entire Flt4 protein coding region was isolated. Three overlapping clones isolated from the HEL-library (as illustrated in FIG. 1) were sequenced using the dideoxy chain termination method with oligonucleotide primers designed according to the sequences obtained. All portions of the cDNAs were sequenced on both strands. Sequence analyses were performed using the GCG package programs [Devereux et al., *Nucleic Acids Res.*, 12: 387-395 (1984) and the Prosite program for Apple Macintosh].

Figure 1B:
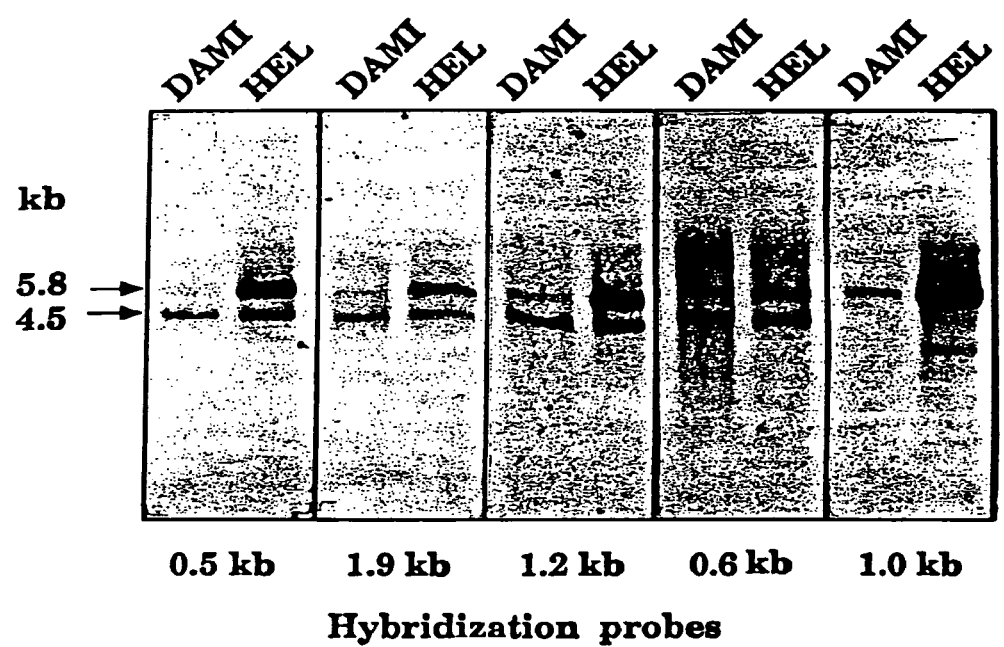
FIG. 1B is a photographic reproduction of a Northern hybridization gel.

FIG. 1A illustrates a schematic structure of the Flt4 cDNA clones analyzed. Arrows delineate subcloned restriction fragments (whose sizes are shown in kb) used for probing Northern blots depicted in FIG. 1B. E=EcoRI site, S=SphI site. FIG. 1B illustrates Northern hybridization analysis of DAMI and HEL leukemia cell RNAs with the probes shown in FIG. 1A.

Results

A 210 bp long Flt4 cDNA fragment isolated by a PCR cloning method from a HEL cell cDNA library was used as a molecular probe to screen an oligo-dT-primed human erythroleukemia cell cDNA library.

Nucleotide sequence analysis of clones revealed an open reading frame of 1298 amino acid (aa) residues (SEQ ID NO: 2, FIG. 2). The translational initiator methionine marked in the figure is surrounded by a typical consensus sequence [Kozak, *Nucleic Acids Res.*, 12: 857-872 (1984)] and followed by a hydrophobic amino acid sequence characteristic of signal sequences for translocation into the endoplasmic reticulum.

The extracellular domain of Flt4 can be aligned into seven immunoglobulin-like loops (FIG. 2). The figure also shows the comparison of Flt4 with Flt1, which contains very similar structures. The amino acid sequence of Flt1 is set forth as SEQ. ID NO: 5.

Amino acid residues 775-798 form a hydrophobic stretch of sequence, which is likely to function as the transmembrane domain of the receptor, followed by several basic residues on the putative cytoplasmic side of the polypeptide. The juxtamembrane domain is 44 residues long before the beginning of a tyrosine kinase sequence homology at aa 842. With the interruption of homology in the kinase insert sequence of 65 aa, this homology is first lost at 1175 aa at carboxyl terminal tail of the receptor. A search for related tyrosine kinase domains in the amino acid sequence database (Swissprot and NBRF) identifies the Flt1 and PDGFRB tyrosine kinases with homology of about 80 and 60% in the catalytic tyrosine kinase regions respectively.

Example 2

Preparation of an Anti-Flt4 Antisera

A 657 base pair EcoRI fragment encoding the predicted C-terminus of Flt4 short form was cloned in-frame with the glutathione-S-transferase coding region in the pGEX-1λT bacterial expression vector (Pharmacia) to produce a GST-Flt4 fusion protein in *E. coli*. The resulting fusion protein was produced in bacteria and partially purified by glutathione affinity chromatography according to the manufacturer's instructions. This protein was used in immunization of rabbits in order to produce polyclonal antibodies against Flt4. Antisera were used after the third booster immunization.

Example 3

Expression of Flt4 in COS Cells

Materials and Methods

The full-length Flt4 protein coding sequence (combined from three clones, FIG. 1) was inserted into the HindIII-BamHI site of SV poly mammalian expression vector [Stacey et al., *Nucleic Acids Res.*, 18: 2829 (1990)] construct SV14-2. The expression vectors (SV-FLT4 short and SV-FLT4 long, containing the respective forms of Flt4 cDNA) were introduced into COS cells by DEAE-dextran transfection method [McCutchan et al., *J. Natl. Cancer Inst.*, 41: 351-357 (1968)]. Two days after transfection, the cells were washed with phosphate-buffered saline (PBS) and scraped into immunoprecipitation buffer (10 mM Tris pH 7.5, 50 mM NaCl, 0.5% sodium deoxycholate, 0.5% Nonidet P40, 0.1% SDS, 0.1 TIU/ml Aprotinin). The lysates were sonicated, centrifuged for 15' at 10,000×g and incubated overnight on ice with 3 ml of the antisera. Protein A sepharose (Pharmacia) was added and the incubation was continued for 30' with rotation. The precipitates were washed four times with the immunoprecipitation buffer, once with PBS and once with aqua before analysis in SDS-PAGE.

Results

The structural predictions of the Flt4 cDNA sequence were tested by cloning the full-length Flt4 short and long protein-coding regions into the HindIII-BamHI sites of the pSV poly expression vector and transfecting these expression vectors into COS cells. The proteins produced by these two constructs differ in their C-terminus: the longer form contains an additional 65 amino acids. Two days after transfection, the cells were lysed and immunoprecipitated using antibodies generated against the GST-Flt4 fusion protein containing 40 carboxyl terminal amino acid residues of the short form of the predicted Flt4 protein (i.e., a portion common to both the short and long forms of Flt4). Immunoprecipitated polypeptides were analyzed by SDS-polyacrylamide gel electrophoresis. The preimmune serum did not reveal any specific bands, whereas the Flt4-specific antibodies recognize two bands of about 170 and 190 KD. These two bands may represent differentially glycosylated forms of Flt4 protein.

Example 4

Expression of Flt4 in NIH3T3 Cells

Materials and Methods

The full-length Flt4 cDNA (short form) was subcloned into the LTRpoly vector (see Makela, e al., *Gene*, 118:293-294 (1992), disclosing plasmid vector pLTRpoly, having ATCC accession number 77109 and GeneBank accession number X60280) containing the Moloney murine leukemia virus long terminal repeat promoter. This LTR-FLT4 expression vector was used with pSV2neo marker plasmid to co-transfect NIH3T3 cells, and G418 resistant clones were analyzed for Flt4 expression.

For Western immunoblotting analyses, cells on one confluent large plate were lysed in 2.5% SDS, 125 mM Tris, pH 6.5. Cell lysates were electrophoresed on SDS-page and electroblotted onto a nitrocellulose membrane. The membrane was incubated with the antiserum raised against the Flt4 carboxy-terminus peptide, and bound antibodies were visualized using horseradish peroxidase conjugated swine anti-rabbit antiserum (Dako) and ECL reagents (Amersham). For metabolic labeling, the cultures were labeled with 100 µCi/ml $^{35}$S-methionine for one hour. After labelling, cells were washed twice and incubated in their growth medium for 1 or 2 hours, lysed, immunoprecipitated with anti-Flt4 antibodies, and analyzed by SDS-PAGE and autofluorography.

Results

The 170 and 190 KD polypeptides could be detected in the Flt4 short form-transfected into NIH3T3 cells, but not in cells transfected with pSV2neo only. In addition to these two bands, a major band of about 120 Kd was observed in the clones producing Flt4. Metabolic labeling and pulse-chase experiments showed that this protein is generated as a result of post-translational processing of the short form Flt4 polypeptides.

Example 5

Chromosomal Mapping of the Flt4 Locus

Because some clustering of class III receptor genes has been observed, it is of great interest to determine the chromosomal localization of Flt4. Thus, rodent-human cell hybrids were analyzed, indicating linkage of Flt4 to human chromosome 5.

Localization of the Flt4 gene in the region 5q33->5qter was determined using hybrids carrying partial chromosome 5s. These hybrids were tested for presence of the Flt4 locus by filter hybridization. The region of chromosome 5 common to Flt4-positive hybrids and absent from the Flt4-negative hybrids was 5q33.1-qter. The presence of human chromosome 5q33-qter in the hybrids is thus correlated with the presence of Flt4 sequences. The regional mapping results indicated that the Flt4 locus is telomeric to the CSF1R/platelet-derived growth factor receptor-β (PDGFRB) locus as well as to the β-adrenergic receptor (ADRBR) locus since these loci are all present in the hybrid GB 13, which was negative for Flt4.

Example 6

Expression of the Flt4 mRNA in Tumor Cell Lines and Endothelial Cells

The leukemia cell lines (K562) used in this study have been reported in several previous publications; [Lozzio et al., *Blood*, 45: 321-334 (1975)], HL-60 [Collins et al., *Nature*, 270: 347-349 (1977)], HEL [Martin et al., Science, 216: 1233-1235 (1982)], DAMI [Greenberg et al., *Blood*, 72: 1968-1977 (1988)], MOLT-4 [Minowada et al., *J. Natl. Cancer Inst.*, 49: 891-895 (1972)], Jurkat [Schwenk et al., *Blut*, 31: 299-306 (1975)], U937 [Sundström et al., *Int. J. Cancer*, 17: 565-577 (1976)], KG-1 [Koeffler et al., *Science*, 200: 1153-1154 (1978)], JOK-1 [Andersson et al., 1982, in R. F. Revoltella (ed.), *Expression of Differentiated Functions in Cancer Cells*, 239-245, Raven Press, New York] and ML-2 [Gahmberg et al., 1985, in L. C. Andersson, et al. (ed.), *Gene Expression During Normal and Malignant Differentiation*, 107-123, Academic Press, London]. The following tumor cell lines, obtained from the American Type Culture Collection also were analyzed: JEG-3, a choriocarcinoma; A204, a rhabdomyosarcoma; SK-NEP-1, a nephroblastoma; BT-474, a breast carcinoma; Y79, a retinoblastoma. The leukemia cells were grown in RPMI containing 10% fetal calf serum (FCS) and antibiotics. Dami cells were cultivated in Iscove's modified DMEM with 10% horse serum. A permanent endothelial hybrid cell line (EAhy926) obtained by fusing first-passage human umbilical vein endothelial cells with the A549 lung carcinoma cells [Edgell et al., *Proc. Natl. Acad. Sci. USA*, 50: 3734-3737 (1983)] was cultured in DMEM-HAT medium containing 10% FCS and antibiotics.

Poly(A)$^+$ RNA was extracted from the cell lines as described [Sambrook et al., see above]. 5 µg of the Poly(A)$^+$ RNA samples were electrophoresed in agarose gels containing formaldehyde and blotted using standard conditions [Sambrook et al., see above]. The inserts of the Flt4 cDNA clones were labelled by the random priming method and hybridized to the blots. Hybridization was carried out in 50% formamide, 5×Denhardt's solution (100×Denhardt's solution is 2% each of Ficoll, polyvinylpyrrolidone and bovine serum albumin), 5×SSPE (3M NaCl, 200 mM NaH$_2$PO$_4$.H$_2$O, 20 mM EDTA, pH 7.0), 0.1% SDS (sodium dodecyl sulphate), and 0.1 mg/ml of sonicated salmon sperm DNA at 42° C. for 18-24 h. The filters were washed at 65° C. in 1×SSC (150 mM NaCl, 15 mM sodium citrate, pH 7.0), 0.1% SDS and exposed to Kodak XAR-5 film.

Northern analyses were performed with the extracted poly (A)$^+$ RNA from eight leukemia cell lines (HEL, K562, DAMI, U937, MOLT4, HL60, Jurkat, and KG-1) and the endothelial hybrid cell line (EAhy926). Hybridization with the GAPDH probe was used as an internal control for the loading of even amounts of RNA to the analysis. Only the HEL erythroleukemia cells, and DAMI megakaryoblastic leukemia cells expressed 5.8 kb and 4.5 kb Flt4 mRNA. The K562 erythroleukemia, Jurkat and MOLT-4 T-cell leukemias, as well as HL-60 promyelocytic leukemia, U937 monocytic leukemia, and KG-I myeloid leukemia cells were negative for the Flt4 mRNA.

Northern analyses were performed with the extracted poly (A)$^+$ RNA from five tumor cell lines (JEG-3, A-204, SK-NEP-1, BT-474, and Y79) and two of the aforementioned leukemia cell lines (JOK-1, MOLT4). The labeled S2.5 cDNA clone (see FIG. 1) was used as the hybridization probe. Hybridization with a β-actin probe was used as an internal control for the loading of even amounts of RNA to the analysis. Only the SK-NEP-1 nefroblastoma and Y79 retinoblastoma cells were observed to contain Flt4 transcripts.

Tera-2 teratocarcinoma cells were analyzed after a 10 day treatment with vehicle (−) or retinoic acid (+) to induce neuronal differentiation [Thompson et al., *J. Cell Sci.*, 72: 37-64 (1984). In Northern blotting analysis of poly(A)$^+$ RNA isolated from the cells it was found that the undifferentiated cells expressed 5.8 kb and 4.7 kb mRNAs for Flt4, but after the 10 day differentiation, no Flt4 mRNA could be detected in Northern blotting and hybridization. These results indicate that Flt4 was downregulated during the differentiation of these cells.

Flt4 mRNA expression also was analyzed in undifferentiated and TPA-differentiated HEL cells. Both the HEL and DAMI cell lines possess a dual erythroid/megakaryoblastic phenotype and can be induced to further expression of megakaryoblastic markers by treatment with the tumor promotor 12-O-tetradecanoylphorbol-13-acetate (TPA). We analyzed whether Flt4 expression is stimulated in these cells during their differentiation. HEL cells were analyzed 2 days after treatment with TPA or with DMSO used to dissolve it. After stripping off the Flt4 signal, the filter was probed with Rb-1 and β-actin cDNAs to confirm an even loading of the lanes. On the basis of densitometric scanning analysis of the autoradiograph and normalization against the constitutive expression of the GAPDH gene, it was determined that the Flt4 mRNA level was increased about 3.4 fold in TPA-induced HEL cells, when the cells undergo megakaryoblastic differentiation.

Example 7

Expression of Flt4 in Fetal Lung

In situ hybridization: Lung tissue from a 15 week-old human fetus was obtained with the permission of joint ethical committee of the University Central Hospital and the University of Turku, Finland. The sample was fixed in 10% formalin for 18 hours at 4° C., dehydrated, embedded in wax, and cut into 6 μm sections. The RNA probes of 206 and 157 bases (antisense and sense) were generated from linearized plasmid DNA using SP6 and T7 polymerases and [$^{35}$S]-UTP. In situ hybridization of sections was performed according to Wilkinson et al., *Development*, 99:493-500 (1987); Wilkinson, *Cell*, 50:79-88 (1987), with the following modifications: 1) instead of toluene, xylene was used before embedding in paraffin wax; 2) 6 μm sections were cut, placed on a layer of diethyl pyrocarbonate-treated water on the surface of glass slides pretreated with 2% 3-aminopropyl-triethoxysilane (Sigma); 3) alkaline hydrolysis of the probes was omitted; 4) the hybridization mixture contained 60% deionized formamide; 5) the high stringency wash was for 80 minutes at 65° C. in a solution containing 50 mM DTT and 1×SSC; 6) the sections were covered with NTB-2 emulsion (Kodak) and stored at 4° C. After an exposure time of 14 days, the slides were developed for 2.5 minutes in a Kodak D-19 developer and fixed for 5 minutes with Unifix (Kodak). The sections were stained with hematoxylin in water.

In the hybridization studies using the anti-sense probe, Flt4 mRNA was observed mainly in certain endothelial cells of the lungs of a 15 week old fetus. Control hybridizations with the sense strand probe and with RNAse A-treated sections did not give a signal above background.

For immunoperoxidase staining, a 1:100 dilution of the anti-Flt4 antibody, peroxidase-conjugated swine anti-rabbit antibodies and methods standard in the art were used. Control stainings with preimmune serum or immunogen-blocked serum did not give a signal. Lung tissue from seventeen-week old human fetuses were analyzed, and the results were consistent with those of the mRNA in situ hybridization experiments: the endothelium of certain large vessels of the lung were stained positive with the rabbit anti-Flt4 antiserum.

Example 8

Identification of Flt4 Genes in Non-Human Mammalian Species

Figure 4:
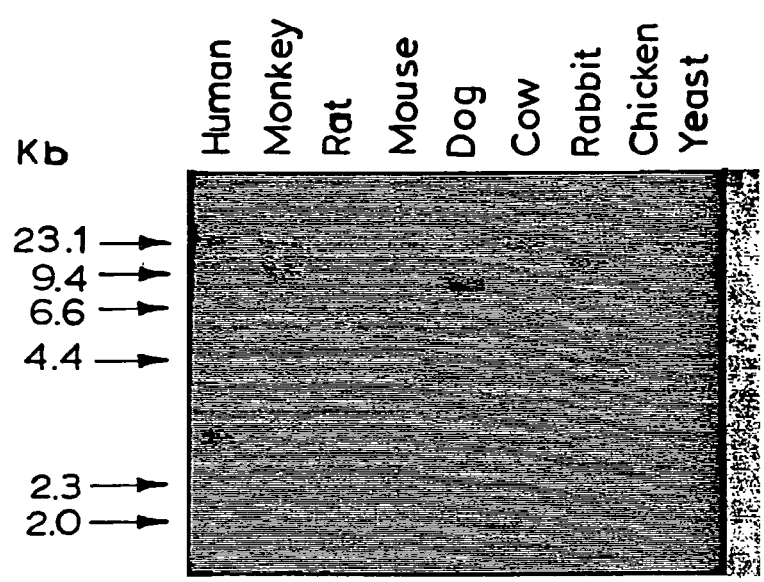
FIG. 4 is a photographic reproduction of a gel illustrating a hybridization analysis of Flt4 sequences in DNA samples from different species.

In FIG. 4 the results of an experiment examining the presence of Flt4 sequences in DNA from different species is shown. In order to reveal how well the Flt4 gene has been conserved in evolution, the 2.5 kb cDNA fragment (see FIG. 1) was hybridized to genomic DNAs purified from different animals and from yeast and digested with EcoRI. The hybridization solution comprised 50% formamide, 5×Denhardt's solution, (100×Denhardt's solution is 2% each of Ficoll, polyvinylpyrrolidone and bovine serum albumin), 5× saline-sodium phosphate-EDTA (3M NaCl, 200 mM NaH$_2$PO$_4$—H$_2$O, 20 mM EDTA, pH 7.0), 0.1% sodium dodecyl sulfate, and 0.1 mg/ml sonicated salmon sperm DNA. Hybridization was performed at 42° C. for 24 hours. The filter was washed at 65° C. in 1× standard saline citrate (150 mM NaCl, 15 mM sodium citrate, pH 7.0) and 0.1% sodium dodecyl sulfate and exposed to Kodak XAR-5 film. Specific bands were found in monkey, rat, mouse, dog, cow, rabbit, and chick DNAs, but the yeast DNA did not give a signal. The Flt4 cDNA has been isolated from quails. See Eichmann et al., *Gene*, 174(1): 3-8 (Sep. 26, 1996) and Genbank accession number X83287.

Example 9

Flt4 Gene Expression in Adult Human Tissues

Flt4 mRNA expression in adult human tissues was analyzed using 2 μg of poly(A)$^+$ RNA from heart, brain, placenta, lung, liver, skeletal muscle, kidney, and pancreas tissues (Multiple Tissue Northern Blot, Clontech Inc.) by hybridization with the Flt4 cDNA probe. Control hybridizations with probes for constitutively expressed genes showed an even loading of the lanes.

Hybridization of poly(A)$^-$ RNA from various human tissues with the Flt4 cDNA fragment showed mRNA bands of 5.8 and 4.5 kb mobility and a weakly labeled band of 6.2 kb in placenta, lung, heart and kidney. Faint mRNA bands were seen in the liver and skeletal muscle, whereas the pancreas and brain appeared to contain very little if any Flt4 RNA.

Example 10

Flt4 Expression in Human Fetal Tissues

To examine Flt4 mRNA expression in human fetal tissues, a Northern blot containing total RNA from the below-listed tissues of 16-19 week human fetuses was hybridized with the 1.9 kb Flt4 cDNA fragment (see FIG. 1) and the resulting autoradiograph was scanned with a densitometer. The results were normalized for the amount of RNA estimated from a UV picture of the corresponding ethidium bromide (EtBr) stained gel. The following symbols denote mRNA levels in an increasing order: −,+,++,+++.

TABLE 1

| Fetal tissue | mRNA |
|---|---|
| Brain | |
| Meninges | + |
| Cortical plate | ++ |
| Intermediate zone | +++ |
| Ependymal zone | + |
| Cerebellum | ++ |
| Choroid plexus | + |
| Liver | + |
| Pancreas | + |
| Small intestine | − |
| Heart | + |
| Lung | +++ |
| Kidney | ++ |
| Adrenal | ++ |
| Skin | ++ |
| Spleen | +++ |
| Thymus | − |

Analysis of human fetal tissues showed that all except the thymus and small intestine contain Flt4 transcripts. The highest expression levels were found in lung and spleen.

Example 11

Flt4 Expression Vector

Full-length Flt4 cDNA (short form) was produced by a) ligation of a SphI-cleaved Flt4 PCR fragment [amplified from the S2.5 kb clone (see FIG. 1) using the primer oligonucleotides 5'-ACATGCATGC CACCATGCAG CGGGGCGCCG CGCTGTGCCT GCGACTGTGG CTCTGCCTGG GACTCCTGGA-3' (SEQ. ID NO. 7) (forward) and 5'-ACATGCATGC CCCGCCGGT CATCC-3' (reverse)] (SEQ. ID NO. 8) to the 5' end of the S2.5 kb fragment, subcloned into the pSP73 vector (Promega), using two SphI sites; b) ligation of a PCR fragment containing the last 138 bps amplified from the 0.6 kb EcoRI fragment (see FIG. 1) with the oligonucleotide primers 5'-CGGAATTCCC CATGACCCCA AC-3'(SEQ. ID NO. 9) (forward) and 5'-CCATCGATGG ATCCTACCTG AAGCCGCTTT CTT-3' (SEQ. ID NO. 10) (reverse) to the 3' end of construct a) using the EcoRI and BamHI sites; c) ligation of a 1.2 kb EcoRI fragment in the EcoRI site of construct b); d) ligation of the resulting full length HindIII-BamHI fragment into the HindIII-BamHI cleaved SV-poly expression vector [Stacey et al., *Nucl. Acids Res.*, 18: 2829 (1990)].

Example 12

Identification of an Flt4 Ligand

Conditioned media from the PC-3 prostatic adenocarcinoma cell line (ATCC CRL 1435) cultured for 7 days in F12 medium in the absence of fetal bovine serum (FBS) was cleared by centrifugation at 16 000×g for 20 minutes and screened for the ability to induce tyrosine phosphorylation of Flt4.

NIH3T3-cells recombinantly expressing Flt4 (see Example 13) were reseeded on 5 cm diameter cell culture dishes and grown to confluency in Dulbecco's modified minimal essential medium (DMEM) containing 10% fetal bovine serum and antibiotics. The confluent cells were washed twice in phosphate-buffered saline (PBS) and starved in DMEM/ 0.2% bovine serum albumin overnight. For stimulation, the starvation medium was replaced by 1 ml of the conditioned medium and the cells were incubated at 37° C. for 5 minutes.

After stimulation with the PC-3 conditioned medium, the culture plates containing the cells were put on ice and washed twice with Tris-HCl, pH 7.4, 150 mM NaCl containing 100 mM $NaVO_4$. The washing solution was removed from the dishes and the cells were lysed in RIPA buffer [10 mM Tris-HCl pH 7.5, 50 mM NaCl, 0.5% sodium deoxycholate, 0.5% Nonidet P40, 0.1% sodium dodecyl sulphate (SDS)] containing aprotinin, 1 mM PMSF and 1 mM $NaVO_4$, and the lysates were sonicated for 10 seconds twice. The lysates were then centrifuged at 16,000×g for 30 minutes and the supernatants were transferred to new tubes and used for immunoprecipitation.

The polyclonal antibodies against the Flt4 C-terminus (described above) were used for immunoprecipitation. Supernatants from the cell lysates were incubated for 2 hours on ice with 2 to 4 µl of rabbit polyclonal anti-Flt4 antiserum. About 30 µl of a 50% (vol/vol) solution of protein A-Sepharose (Pharmacia) in PBS was added, and incubation was continued for 45 minutes with rotation at +4° C. The immunoprecipitates were washed three times with the RIPA buffer and once with PBS. The immunoprecipitates were then subjected to SDS-polyacrylamide gel electrophoresis (SDS-PAGE) in a 7.5% gel and blotted on nitrocellulose. These Western blots were incubated with monoclonal anti-phosphotyrosine (anti-P-Tyr) antibodies (1:2000 dilution of PT-66 Sigma, cat. P-3300) followed by detection with peroxidase-conjugated rabbit anti-mouse antibodies (1:1000 dilution, Dako, cat. P 161) using the chemiluminesce detection system (Amersham). In some cases, the blots were stripped to clear previous signals for 30 minutes at 50° C. in 100 mM 2-mercaptoethanol, 2% SDS, 62.5 mM Tris-HCl pH 6.7 with occasional agitation and re-stained with anti-Flt4 antibodies (1:1000 dilution) followed by staining with peroxidase-conjugated swine anti-rabbit antibodies (1:1000 dilution, Dako, P217). As a positive control for the tyrosine phosphorylation of Flt4, anti-Flt4 immunoprecipitates from the Flt4-expressing NIH3T3 cells treated with 100 mM of the tyrosyl phosphatase inhibitor sodium pervanadate (PerVO4) for 20 minutes were used. Treatment of cells with Sodium pervanadate was done by addition of 100 mM (final concentration) of sodium orthovanadate and 2 mM (final concentration) of hydrogen peroxide to the cell medium and incubation of the cells for 20 minutes at 37° C. 5% $CO_2$. That procedure resulted in the generation of the peroxidized form of vanadate (vanadyl hydroperoxide), which is a very potent inhibitor of the protein tyrosine phosphatases in living cells.

The PC-3 cell conditioned medium stimulated tyrosine phosphorylation of a 120 kD polypeptide which co-migrated with tyrosine phosphorylated, processed mature form of Flt4. Co-migration was confirmed after restaining of the blot with anti-Flt4 antibodies.

To prove that 120 kD polypeptide is not a non-specific component of the conditioned medium, 15 nil of conditioned medium were separated by SDS-PAGE, blotted on nitrocellulose, and the blot was stained with anti-P-Tyr antibodies. Several polypeptides were detected, but none of them comigrated with Flt4, indicating that the 120 kD band is indeed tyrosine-phosphorylated protein immunoprecipitated from the stimulated cells. Analysis of stimulation by PC-3 conditioned medium pretreated with heparin Sepharose CL-6B (Pharmacia) for 2 hours at room temperature (lane 3) shows that the Flt4 ligand does not bind to heparin.

Unconditioned medium did not induce Flt4 autophosphorylation. Also, neither non-transfected NIH3T3 cells nor NIH3T3 cells transfected with the FGFR-4 showed tyrosine phosphorylation of the 120 kD polypeptide upon stimulation with the conditioned medium from PC-3 cells. Stimulating activity was considerably increased when the PC-3 conditioned medium was concentrated fourfold using a Centricon-10 concentrator (Amicon). Also, the flow through obtained after the concentration, containing proteins of less than 10,000 molecular weight (<10,000), did not stimulate phosphorylation of Flt4. Pretreatment of the concentrated conditioned medium of PC-3 cells with 50 ml of the Flt4 extracellular domain (Flt4EC-6×His, see below) coupled to CNBr-activated Sepharose (1 mg/ml) according to the manufacturer's instructions completely abolished the tyrosine phosphorylation of Flt4. Analogous pretreatment of the conditioned medium with Sepharose CL-4B did not affect its stimulatory activity.

These data prove that PC-3 cells produce soluble ligand for Flt4. The above experiments prove that the ligand binds to the recombinant Flt4 EC domain. Thus, that ligand can be purified using the recombinant Flt4 EC domain in affinity chromatography. The purified protein can be electrophoresed in SDS-PAGE, blotted onto polyvinylidene difluoride (PVDF) membranes and its amino terminal sequence can be determined by methods standard in the art. Alternatively, the purified ligand can be digested to peptides for their amino terminal sequence determination. Peptide sequences obtained from the purified protein are used for the synthesis of a mixture of oligonucleotides encoding such sequences. Such oligonucleotides and their complementary DNA strand counterparts can be radioactively labelled by and used for the screening of cDNA libraries made from the PC-3 cells to obtain a cDNA encoding the ligand, all by methods standard in the art (Wen et al., *Cell* 69: 559-572 (1992)). Alternatively, such oligonucleotides and their counterparts can be used as primers in polymerase chain reaction (PCR) to amplify sequences encoding the ligand using cDNA made from PC-3 cell RNA as a template. Such method of cDNA synthesis and PCR (RT-PCR) is standard in the art (Innis et al., 1990, PCR protocols, Academic Press; McPherson, M. J. et al., 1991, PCR, a practical approach, IRL Press; Partanen et al., *Proc. Natl. Acad. Sci., USA*, 87: 8913-8917 (1990)). Yet another alternative is to clone the Flt4 ligand from the PC-3 cells by using cDNAs cloned into eukaryotic expression vector (e.g. using the Invitrogen Librarian cloning kit and vectors provided, such as pcDNA I or pcDNA III) and screening of such libraries transfected into, e.g., COS cells with Flt4-alkaline phosphatase (Cheng and Flanagan, *Cell,* 79: 157-168, (1994)), Flt4-immunoglobulin (Flt4-Ig) (Lyman et al., *Cell,* 75, 1157-1167 (1993)), or similar affinity reagents, by methods standard in the art.

Example 13

Cell Lines and Transfections

NIH3T3 cells and 293-EBNA cells (Invitrogen) were cultured in DMEM containing 10% FCS. For stable expression, NIH3T3 cells were transfected with the LTR-FLT41 vector together with the pSV-neo vector (see Example 4, above) where the Flt4 cDNA is expressed under the control of the Moloney murine leukemia virus LTR promoter, by the lipofection method using the DOTAP transfection reagent (Boehringer-Mannheim). COS-1 cells were transfected by the DEAE dextran method (McClutchan and Pagano, *J. Natl. Cancer Inst.,* 41: 351-35 (1968)). Transfected cells were selected in 500 mg/ml neomycin.

Example 14

Construction and Expression of Flt4 Fusion Proteins

The pVTBac-FLT4EC-6×His Fusion Construct.
The ends of cDNA encoding Flt4 were modified as follows: The 3' end of Flt4 cDNA sequence encoding the extracellular domain (EC) was amplified using oligonucleotides (SEQ ID NO: 13
5'-CTGGAGTCGACTTGGCGGACT-3', SalI site underlined containing sequence corresponding to nucleotides 2184-2204 of SEQ ID NO: 1) and (SEQ ID NO: 14
5'CGCGGATCCCTAGTGATGGTGATGGTGATGTCTACCTTCGATCAT
GCTGCCCTTATCCTC-3', BamHI site underlined, containing sequence complementary to nucleotides 2341-2324 of SEQ ID NO: 1) encoding 6 histidine residues for binding to a Ni-NTA column (Qiagen, Hilden, Germany) followed by a stop codon. The amplified fragment was digested with SalI and BamHI and ligated as a SalI-BamHI fragment into the LTR-FLT41 vector (see Example 4), replacing a unique SalI-BamHI fragment containing sequences encoding the Flt4 transmembrane and cytoplasmic domains.

The 5' end of the Flt4 cDNA without the Flt4 signal sequence encoding region was amplified by PCR using oligonucleotides (SEQ ID NO: 11
5'-CCCAAGCTTGGATCCAAGTGGCTACTCCATGACC-3', HindIII and BamHI sites underlined, containing sequence corresponding to nucleotides 86-103 of SEQ ID NO: 1) and 5'-GTTGCCTGTGATGTGCACCA-3' (SEQ ID NO: 12, containing sequence complementary to nucleotides 700-681 of SEQ ID NO: 1). This amplified fragment (which included nucleotides 86-700 of SEQ ID NO: 1) was digested with HindIII and SphI (the SphI site, corresponding to nucleotides 588-593 of SEQ ID NO: 1, being within the amplified region of the Flt4 cDNA).

The resultant HindIII-SphI fragment was used to replace a HindIII-SphI fragment in the modified LTR-FLT41 vector described immediately above (the HindIII site is in the 5' junction of the Flt4 insert with the pLTRpoly portion of the vector, the SphI site is in the Flt4 cDNA and corresponds to nucleotides 588-593 of SEQ ID NO: 1). The resultant Flt4EC-6×His insert was then ligated as a BamHI fragment into the BamHI site in the pVTBac plasmid (Tessier et al., *Gene* 98: 177-183'(1991)). The construct was transfected together with baculovirus genomic DNA into SF-9 cells by lipofection. Recombinant virus was generated and used for infection of High-Five cells (Invitrogen).

The Flt4-AP Fusion Construct.
The 3' end of the sequence encoding the Flt4 EC domain was amplified using oligonucleotides 5'-CTGGAGTC-GACTTGGCGGACT-3' (SEQ ID NO: 15) and 5'-CGG-GATCCCTCCATGCTGCCCTTATCCT-3' (SEQ ID NO: 16) and ligated as SalI-BamHI fragment into the LTR-FLT41 vector, replacing sequences encoding the transmembrane and cytoplasmic domains. The resulting insert was then ligated as a HindIII-BamHI fragment into the HindIII-BglII sites of plasmid APtag-1 in frame with the alkaline phosphatase coding region (Flanagan and Leder, 1990, Cell 63, 185-194). NIH3T3 cells were co-transfected with this Flt4-AP construct and pSV2neo (Southern and Berg, *J. Mol. Appl. Genet.* 1: 327-341 (1982)) by lipofection using the DOTAP transfection reagent (Boehringer) and the transfected cells were selected in the presence of 500 mg/ml neomycin. The recombinant protein produced into the medium was detected by a colorimetric reaction for staining for alkaline phosphatase activity (Cheng and Flanagan, *Cell* 79: 157-168 (1994)).

The Flt4-Ig Construct.
A recombinant DNA encoding an Flt4-immunoglobulin chimera was constructed as follows. The 5' end of the cDNA encoding Flt4, including Flt4 nucleotides encoding the signal sequence, was amplified by PCR using primers 5'-GGCAAGCTTGAATTCGCCACCATG-CAGCGGGGCGCC-3' (SEQ ID NO: 17) and 5'-GTTGCCT-GTGATGTGCACCA-3' (SEQ ID NO: 18) and ligated as HindIII-SphI fragment into the LTR-FLT41 vector. The 3' end of Flt4 EC-encoding sequence was amplified using oligonucleotides 5'-CTGGAGTCGACTTGGCGGACT-3' (SEQ ID NO: 19) and 5'-CGCGGATCCAAGCTTACTTACCTTC-CATGCTGCCCTTATCCTCG-3' (SEQ ID NO: 20) and ligated as SalI-BamHI fragment into the LTR-FLT41 vector replacing the sequences encoding the transmembrane and cytoplasmic domains. This Flt4EC insert containing a splice donor site was ligated first into pHγCE2 containing exons encoding the human immunoglobulin heavy chain hinge and constant region exons (Karjalainen, K., *TIBTECH,* 9: 109-113 (1991)). The EcoRI-BamHI insert containing the Flt4-Ig chimera was then blunted by methods standard in the art (Klenow) and ligated to the blunted site in pREP7 (Invitrogen). The construct was transfected into 293-EBNA cells by the calcium-phosphate precipitation method and the conditioned medium was used for the isolation of the Flt4-Ig protein by protein A-Sepharose affinity chromatography.

Examples 15-17

Purification and Sequencing the Flt4 Ligand

Cell culture supernatants produced by PC-3 cells under serum-depleted conditions are concentrated 30-50 fold using Centriprep filter cartridges and loaded onto a column of immobilized Flt4 extracellular domain. Two affinity matrices are prepared using the alternative constructs and methods. In the first case the Flt4EC-6×His fusion protein is crosslinked to CNBr-activated Sepharose 4B (Pharmacia) and in the second case the Flt4-Ig fusion protein is coupled to protein A Sepharose using dimethylpimelidate (Schneider et al., 1982, *J. Biol. Chem.* 257: 10766-10769). The material eluted from the affinity column is subjected to further purification using ion exchange and reverse-phase high pressure chromatography and SDS-polyacrylamide gel electrophoresis. Chromatography fractions are tested for the ability to stimulate tyrosine phosphorylation of Flt4. The purified biologically active ligand protein is microsequenced and the degenerate oligonucleotides are made based on the amino acid sequence obtained, for the purpose of isolating and cloning a ligand-encoding cDNA; e.g., from a cDNA library generated from poly(A)+ RNA isolated from PC-3 cells.

A detailed characterization of an Flt4 ligand, designated Vascular Endothelial Growth Factor C (VEGF-C), as well as native human, non-human mammalian, and avian polynucleotide sequences encoding VEGF-C, and VEGF-C variants and analogs, is provided in International Patent Application Number PCT/US98/01973, filed 2 Feb. 1998 (published 6 Aug. 1998 as International Publication Number WO 98/33917); in Joukov et al., *J. Biol. Chem.,* 273(12): 6599-6602 (1998); in Joukov et al., *EMBO J.,* 16(13): 3898-3911 (1997); and in International Patent Application No. PCT/FI96/00427, filed Aug. 1, 1996 (published as International Publication No. WO 97/05250), all of which are incorporated herein by reference in the entirety. As explained therein in detail, human VEGF-C is initially produced in human cells as a prepro-VEGF-C polypeptide of 419 amino acids. An amino acid sequence for human prepro-VEGF-C is set forth in SEQ ID NO: 21, and a cDNA encoding human VEGF-C has been deposited with the American Type Culture Collection (ATCC), 10801 University Blvd., Manassas, Va. 20110-2209 (USA), pursuant to the provisions of the Budapest Treaty (Deposit date of 24 Jul. 1995 and ATCC Accession Number 97231). VEGF-C sequences from other species also have been reported. See Genbank Accession Nos. MMU73620 (*Mus musculus*); and CCY15837 (*Coturnix coturnix*) for example, incorporated herein by reference.

The prepro-VEGF-C polypeptide is processed in multiple stages to produce a mature and most active VEGF-C polypeptide of about 21-23 kD (as assessed by SDS-PAGE under reducing conditions). Such processing includes cleavage of a signal peptide (SEQ ID NO: 21, residues 1-31); cleavage of a carboxyl-terminal peptide (corresponding approximately to amino acids 228-419 of SEQ ID NO: 21 and having a pattern of spaced cysteine residues reminiscent of a Balbiani ring 3 protein (BR3P) sequence [Dignam et al., *Gene,* 88:133-40 (1990); Paulsson et al., *J. Mol. Biol.,* 211:331-49 (1990)]) to produce a partially-processed form of about 29 kD; and cleavage (apparently extracellularly) of an amino-terminal peptide (corresponding approximately to amino acids 32-103 of SEQ ID NO: 21) to produced a fully-processed mature form of about 21-23 10. Experimental evidence demonstrates that partially-processed forms of VEGF-C (e.g., the 29 kD form) are able to bind the Flt4 (VEGFR-3) receptor, whereas high affinity binding to VEGFR-2 occurs only with the fully processed forms of VEGF-C. It appears that VEGF-C polypeptides naturally associate as non-disulfide linked dimers.

Moreover, it has been demonstrated that amino acids 103-227 of SEQ ID NO: 2 are not all critical for maintaining VEGF-C functions. A polypeptide consisting of amino acids 113-213 (and lacking residues 103-112 and 214-227) of SEQ ID NO: 2 retains the ability to bind and stimulate VEGF-C receptors, and it is expected that a polypeptide spanning from about residue 131 to about residue 211 will retain VEGF-C biological activity. The cysteine residue at position 156 has been shown to be important for VEGFR-2 binding ability. However, VEGF-C $\Delta C_{156}$ polypeptides (i.e., analogs that lack this cysteine due to deletion or substitution) remain potent activators of VEGFR-3. The cysteine at position 165 of SEQ ID NO: 2 is essential for binding either receptor, whereas analogs lacking the cysteines at positions 83 or 137 compete with native VEGF-C for binding with both receptors and stimulate both receptors.

An alignment of human VEGF-C with VEGF-C from other species (performed using any generally accepted alignment algorithm) suggests additional residues wherein modifications can be introduced (e.g., insertions, substitutions, and/or deletions) without destroying VEGF-C biological activity. Any position at which aligned VEGF-C polypeptides of two or more species have different amino acids, especially different amino acids with side chains of different chemical character, is a likely position susceptible to modification without concomitant elimination of function. An exemplary alignment of human, murine, and quail VEGF-C is set forth in FIG. 5 of PCT/US98/01973.

Apart from the foregoing considerations, it will be understood that innumerable conservative amino acid substitutions can be performed to a wildtype VEGF-C sequence which are likely to result in a polypeptide that retains VEGF-C biological activities, especially if the number of such substitutions is small. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). Addition or deletion of one or a few internal amino acids without destroying VEGF-C biological activities also is contemplated.

From the foregoing, it will be appreciated that many VEGF-C polypeptides and variants will bind Flt4 (VEGFR-3) with high affinity and therefore are useful as Flt4 binding compounds in aspects of the invention that involve imaging or screening of tissue samples using a Flt4 binding compound. Of particular interest are forms of VEGF-C harboring alterations which diminish or eliminate VEGFR-2 binding affinity, such that the resultant polypeptide possesses increased binding specificity for VEGFR-3. As described above, such alterations include the deletion or replacement of $Cys_{156}$, which substantially eliminates VEGFR-3 binding affinity, or amino acid sequence alterations that destroy natural prepro-VEGF-C proteolytic processing sites (since VEGFR-2 affinity is highest with fully processed VEGF-C). In addition, VEGF-C molecules that have been modified to retain Flt4 binding affinity but that fail to activate Flt4 autophosphorylation are useful Flt4 antagonists in methods of treatment described herein. It will further be apparent from the foregoing teachings that the Flt4 ligand described herein may be used in assays as an additional indicia to confirm the identity of human Flt4 allelic variants, and to confirm that non-human gene sequences having homology to the Flt4 sequences taught herein (See, e.g., Example 8 and FIG. 4) are in fact the non-human counterparts to Flt4. The deduced amino acid sequence for prepro-VEGF-C is set forth herein in SEQ ID NO: 21.

A detailed description of a second Flt4 ligand, designated Vascular Endothelial Growth Factor D (VEGF-D), as well as human polynucleotide sequences encoding VEGF-D, and VEGF-D variants and analogs, is provided in International Patent Application Number PCT/US97/14696, filed 21 Aug. 1997 and published on 26 Feb. 1998 as International Publication Number WO 98/07832; and Achen, et al., *Proc. Nat'l Acad. Sci. U.S.A.,* 95(2): 548-553 (1998), also incorporated herein by reference. As explained therein in detail, human VEGF-D is initially produced in human cells as a prepro-VEGF-D polypeptide of 354 amino acids. The cDNA and deduced amino acid sequences for prepro-VEGF-D are set forth herein in SEQ ID NO: 22. VEGF-D sequences from other species also have been reported. See Genbank Accession Nos. D89628 (*Mus musculus*); and AF014827 (*Rattus norvegicus*), for example, incorporated herein by reference.

The prepro-VEGF-D polypeptide has a putative signal peptide of 21 amino acids and is apparently proteolytically processed in a manner analogous to the processing of prepro-VEGF-C. A "recombinantly matured" VEGF-D lacking residues 1-92 and 202-354 of SEQ ID NO: 22 retains the ability to activate receptors VEGFR-2 and VEGFR-3, and appears to associate as non-covalently linked dimers. The utilities for VEGF-D polypeptides as Flt4 binding compounds in the invention are analogous to those described above for VEGF-C. Likewise, it is expected that analogous alterations to VEGF-D (to eliminate the second of eight conserved cysteines in the VEGF homology domain, $Cys_{136}$, or to eliminate proteolytic processing sites) will result in polypeptides having reduced or eliminated VEGFR-2 binding affinity and, thus, increased Flt4 specificity. VEGF-D molecules that have been modified to retain Flt4 binding affinity but that fail to activate Flt4 autophosphorylation are useful Flt4 antagonists in methods of treatment described herein.

Example 18

Cloning of Mouse Flt4 cDNA Probes

Approximately $10^6$ plaques from a λFIX®II genomic library from 129SV mice (Stratagene) was screened with the S2.5 human Flt4 receptor cDNA fragment described above, covering the extracellular domain. See also Pajusola et al., *Cancer Res.,* 52:5738 (1992). A 2.5 kb BamHI fragment was subcloned from a positive plaque and sequenced from both ends. From this subclone, polymerase chain reaction was used to amplify and clone into the pBluescript KSII+/− vector (Stratagene) an exon fragment covering nucleotides 1745-2049 of the mouse Flt4 cDNA sequence. See Finnerty et al., *Oncogene,* 8:2293 (1993).

A second fragment covering nucleotides 1-192 was similarly cloned.

Example 19

Analysis of Flt4 mRNA in Mouse Tissues

Total RNA was isolated from developing embryos (8-18 days p.c. and one day old mice) according to Chomczynski et al., *Anal. Biochem.,* 162:156 (1987). The sample from 8 day p.c. embryos also included the placenta.

For RNase protection analysis, RNA probe was generated from the linearized murine Flt4 plasmid obtained according to Example 18 using [$^{32}$P]-UTP and T7 polymerase for the antisense orientation. The β-actin probe used corresponds to nucleotides 1188-1279 of the published mouse β-actin sequence. See Tokunaga, et al., *Nucleic. Acid. Res.,* 14:2829 (1986). After purification in a 6% polyacrylamide/7M urea gel, the labelled transcripts were hybridized to 30 μg of total RNA overnight at 52° C. Unhybridized RNA was digested with RNase A (10 U/ml) and T1 (1 mg/ml) at 37° C., pH 7.5 for 1 hour. The RNases were inactivated by proteinase K digestion at 37° C. for 15 minutes and the samples were analysed in a 6% polyacrylamide/7M urea gel.

The pattern of expression of Flt4 analysed in this experiment showed that very weak mRNA signals were obtained from lung, liver, heart, kidney, skeletal muscle and spleen, whereas testis and brain were apparently without specific signal. Analysis of a series of RNAs collected during different phases of mouse development by RNase protection assay showed that the Flt4 mRNA was expressed throughout embryogenesis from day 8 p.c. to newborn mice without great variations in signal intensity.

Example 20

In Situ Hybridization for Flt4 in Mouse Embryos

To better assign Flt4 transcripts to cells and tissues, sections of 7.5 and 8.5 day p.c. mouse embryos were hybridized with labelled Flt4 RNAs. Mouse embryos were derived from matings of CBA and NMRI mice. Pregnant mice were killed by cervical dislocation and the embryos were either immediately frozen or transferred via phosphate buffered saline into 4% paraformaldehyde. The embryos and isolated mouse organs were fixed for 18 hours at 4° C., dehydrated, embedded in paraffin, and cut into 6 μm sections.

RNA probes (antisense and sense) of 192 and 305 nucleotides (see Example 18) were generated from linearized plasmids using [$^{35}$S]-UTP. In situ hybridization of sections was performed according to Wilkinson et al., *Development,* 99:493 (1987); and Wilkinson et al., *Cell,* 50:79 (1987), incorporated by reference herein, with the following modifications: 1) instead of toluene, xylene was used before embedding in paraffin wax; 2) 6 μm sections were cut, placed on a layer of diethyl pyrocarbonate-treated water on the surface of glass slides pretreated with 2% 3-triethoxysilylpropylamine; 3) alkaline hydrolysis of the probes was omitted; and 4) the high stringency wash was for 80 minutes at 65° C. in a solution containing 30 mM DTT and 1×SSC. The sections were covered with NTB-2 emulsion (Kodak) and stored at 4° C. The slides were exposed for 14 days, developed, and stained with hematoxylin. Control hybridizations with sense strand and RNase A-treated sections did not give a specific signal above background.

Flt4 mRNA expression was not detected in 7.5 day p.c. mouse embryos, but bright signals were detected in the developing aortae on day 8.5 of development. In contrast, the developing yolk sac was Flt4-negative. In the extraembryonic tissues, Flt4 was prominently expressed in the allantois, whereas developing blood islands of the yolk sac were negative. On the other hand, angioblasts of the head mesenchyme were strongly Flt4-positive. In the developing placenta, Flt4 signal was first seen in peripheral sinusoidal veins. In 9.5 day p.c. placenta, the endothelium of venous lacunae and the giant cells partially fused to the Reichert's membrane expressed Flt4 mRNA.

Thus, although Flt4 expression was very prominent in the earliest endothelial cell precursors, the angioblasts, it appeared to be restricted only to certain vessels of 8.5 day p.c. embryos. The Tie receptor is known to be expressed in all endothelial cells of developing mouse embryos and thus provides a marker for these cells. See Korhonen, et al. *Oncogene,* 8:395 (1993); and Korhonen et al., *Blood,* 80: 2548-2555 (1992). Notably, in contrast to the Tie probe, the Flt4 probe hybridized very weakly if at all with arterial endothelia of 11.5 day p.c. embryos, e.g. with the endothelium of the developing dorsal aorta or the carotid arteries. Instead, Flt4 signal was much more prominent in the developing veins. For example, Flt4 signal was detected in veins surrounding the developing metanephros, while the Tie probe predominantly recognized capillaries within the metanephros.

Flt4 mRNA was observed to be distributed in several regions of a 12.5 day p.c. mouse embryo, being particularly prominent in the dilated vessel of the axillar region. A similar Flt4-positive vessel structure was seen in the mid-sagittal section in the jugular area (data not shown). A plexus-like pattern of Flt4-expressing vessels appeared in the periorbital region and surrounding the developing vertebrae. Also, just beneath the developing skin, a Flt4-positive vascular network was evident. Weaker capillary signals were obtained from several regions, including the developing brain. Flt4 mRNA could also be detected in small vessels of the neck region, of the developing snout and at the base of the developing tongue as well as in the tail region. Additionally, the liver was strongly positive for Flt4 mRNA in a spotlike pattern.

During further development, Flt4 mRNA appeared to become more restricted to certain vessels of the embryo. A 14.5 day p.c. embryo shows nicely this restricted pattern of expression. In the midsagittal section from such an embryo, the most prominent Flt4 signal was observed along the developing vertebral column in its anterior part. This signal was considered to originate from endothelial cells of the thoracic duct, which is the largest lymphatic vessel formed at this time of development. In contrast, the dorsal aorta and inferior vena cava were negative. Dilated vessels in the mesenteric region were also strongly positive for Flt4. Furthermore, as in the 12.5 day p.c. embryos, vessel networks along anatomical boundaries in the periorbital, lower jaw, as well as in the neck regions contained Flt4-positive endothelia. Similar structures were present in the pericardial space and throughout the subcutaneous tissue. Notably, in contrast to Flt4-negative vessels, all Flt4-positive vessels were devoid of blood cells in their lumen. These expression patterns suggest that Flt4 becomes confined to the endothelia of lymphatic vessels at this time of development. An additional site where we observed Flt4 expression was in the sinusoids of the developing bone marrow.

A transverse section of the upper thorax of a 16.5 day p.c. embryo hybridized with the Flt4 probe also was analyzed. Hematoxylin-eosin staining was performed to visualize the different types of vessels in this area. These include the carotid and brachiochepalic arteries, the vena cava, and the thoracic duct, which is smaller in size and lacks surrounding muscular and connective tissue. Under higher magnification endothelial cells of the thoracic duct as well as a small vessel in the vicinity were observed to hybridize with the Flt4 probe.

Example 21

Analysis of Flt4 mRNA in Cultured Endothelial Cells

The in situ hybridization results described in Example 20 showed that Flt4 is expressed in venous endothelial cells and later in lymphatic vessels and some venous endothelial cells, but not in arterial endothelia. In order to determine if such regulation was maintained in vitro, we studied cultured endothelial cells using Northern blotting and hybridization analysis.

Endothelial cells from human aorta, femoral vein, umbilical vein, and from foreskin microvessels were isolated, cultured, and characterized as previously described in the art. See Van Hinsberg et al., *Arteriosclerosis.* 7:389 (1987); and Van Hinsberg, et al., *Thromb. Haemostas,* 57:148 (1987). They were used at confluent density after five to eight passages (split ratio 1:3) for the isolation of polyadenylated RNA.

The endothelial cell lines EA hy926 (Edgell et al., *Proc. Natl. Acad. Sci.,* 80: 3734-3737 (1983)), BCE (Folkman et al., *Proc. Natl. Acad. Sci.,* 76: 5217-5221 (1979)) and LEII (Schreiber et al., *Proc. Natl. Acad. Sci.,* 82: 6138 (1985)) did not express Flt4. However, cultured human microvascular, venous and umbilical vein endothelial cells were positive for the RN-specific 5.8 and 4.5 kb mRNAs, whereas the aortic endothelial cells were negative. In contrast, another endothelial receptor tyrosine kinase gene, tie, was expressed as a 4.4 kb mRNA in all endothelial cell types studied.

Example 22

Flt4 mRNA in Adult Human Tissues

The results obtained in Example 20 indicated that the Flt4 mRNA becomes largely confined to the endothelium of lymphatic vessels during development. Because of the potential significance of this finding in humans, we also studied Flt4 expression in adult human tissues using a human Flt4 probe. The human Flt4 probe used was an EcoRI-SphI fragment covering base pairs 1-595 of the cDNA (SEQ ID NO:1). See also Pajusola et al., *Cancer Res.,* 52:5738 (1992). The von Willebrand factor probe was an EcoRI-HindIII fragment covering base pairs 1-2334. Bonthron, et al., *Nucleic Acids Res.,* 141:7125 (1986).

We used routinely fixed material sent for histopathological diagnosis. Normal lung tissue was obtained from a resection of the left inferior lung lobe affected by epidermoid cancer. Mesenterium and mesenterial lymph nodes were obtained from a patient having a colonic adenocarcinoma. A normal lymph node adjacent to the salivary gland was enucleated because of its abnormal size. The tonsils from two patients and the two appendixes had no diagnostic changes. Two lymphangiomyomas and three cystic lymphangiomas were studied with similar results.

For human tissues, which were routine samples fixed with 10% formalin for histopathological diagnosis, the normal in situ protocol gave just background, whereas microwave treatment instead of proteinaase K enabled specific hybridization. Shi, et al., *J. Biol. Chem.*, 266:5774 (1991); Catoretti, et al., *J. of Pathol.*, 168:357 (1992).

In the mesenterium, lung and appendix lymphatic endothelia gave Flt4 signals, while veins, arteries, and capillaries were negative. To study whether Flt4 is expressed in the HEVs, the tonsils were studied. Indeed, in the tonsils, Flt4-specific autoradiographic grains were detected in some HEVs.

Example 23

Analysis of Flt4 mRNA in Normal and Metastatic Lymph Node and in Lymphangioma

A portion of a human mesenterial lymph node (see Example 22) was analysed for Flt4 expression. Flt4 expression was observed in the lymphatic sinuses and afferent and efferent lymphatic vessels. The same pattern was observed in a lymph node containing adenocarcinoma metastases. Some HEVs in both normal and metastatic lymph node were also positive. Flt4 expression in a cystic lymphangioma was specific to lymphatic endothelia, as evident from a comparison with the in situ signals for von Willebrandt factor in all blood vessels.

Consistent with these results, immunostaining for Flt4 was strongly positive in the endothelium of cutaneous lymphangiomatosis, a rare disorder characterized by proliferation of presumed lymphatic endothelium. See Lymboussaki et al., *Am. J. Pathol.*, 153(2): 395-403 (August, 1998), incorporated herein by reference in its entirety.

Additionally, immunostaining for Flt4 identified spindle cells within Kaposi's sarcoma cutaneous nodular lesion tissue samples. See Jussila et al., *Cancer Res.*, 58:1599-1604 (April, 1998). In view of the apparent lymphatic specificity of Flt4, These results may be considered consistent with suggestions that certain cells in Kaposi's sarcoma are of lymphatic endothelial origin. See, e.g., Beckstead et al. *Am J. Pathol.*, 119: 294-300 (1985); and Dictor et al., *Am J. Pathol.*, 130: 411-417 (1988).

Example 24

Localization of Flt4 in Fetal Endothelial Cells

As described in Example 2, An Flt4 cDNA fragment encoding the 40 carboxy terminal amino acids of the short form was cloned as a 657 bp EcoRI-fragment into the pGEX-1λT bacterial expression vector (Pharmacia) in frame with the glutatione-S-transferase coding region. The resultant GST-Flt4 fusion protein was produced in *E. coli* and purified by affinity chromatography using a glutathione-Sepharose 4B column. The purified protein was lyophilized, dissolved in PBS, mixed with Freund's adjuvant, and used for immunization of rabbits. Antisera were used after the third booster immunization.

Tissues from 17 and 20-week-old human fetuses were obtained from legal abortions induced with prostaglandins. The study was approved by the Ethical Committee of the Helsinki University Central Hospital. The gestational age was estimated from the fetal foot length. The fetal tissues were embedded in Tissue-Tek (Miles), frozen immediately, and stored at −70° C.

Anti-Flt4 antiserum was cross-absorbed to a GST-Sepharose column to remove anti-GST-antibodies and then purified by GST-Flt4 affinity chromatography. Several 6 μm-thick cryostat sections of the tissues were fixed with acetone and treated with 0.3% $H_2O_2$ in methanol for 30 minutes to block endogenous peroxidase activity. After washing, the sections were incubated with 5% normal swine serum. Sections were then incubated with antibodies against Flt4 and washed. Bound antibodies were detected with peroxidase-conjugated swine anti-rabbit IgG followed by staining for peroxidase activity using 0.2% 3,3-diaminobenzidine (Amersham) as a substrate. The sections were counterstained in Meyer's hematoxylin.

Anti-Flt4 immunoperoxidase staining of human fetal mesenterium showed Flt4 protein in the endothelium of several vessels, while control stainings with antigen-blocked anti-Flt4 antibodies and preimmune sera were negative. For comparison, sections were stained with an antiserum against the Factor VIII-related antigen, which is specific for vascular endothelial cells. Immunoperoxidase Staining for Flt4 was observed over endothelial cells of vessels, which did not contain red blood cells, while blood vessels were negative. The vessels without red blood cells are likely to be lymphatic endothelial cells; such vessels are particularly frequent in the mesenterium. The antibodies against Factor VIII related antigen stained endothelial cells in all vessels.

Example 25

Production of Monoclonal Antibodies Against Flt4

Fusion I:

Recombinant Flt4 extracellular domain protein was produced by expressing the Flt4EC-6×His-pVTBac plasmid construct (Example 14) in High-Five cells. The Flt4 extracellular domain (Flt4EC) was purified from the culture medium of the infected High-Five cells using Ni-NTA affinity chromatography according to manufacturer's instructions (Qiagen) for binding and elution of the 6×His tag encoded in the COOH-terminus of the recombinant Flt4 extracellular domain.

Four month old Balb/c male mice were immunized by intraperitoneal injection of the purified, recombinantly produced Flt4 extracellular domain protein (150 μg/mouse) emulsified with Freund's complete adjuvant. Booster injections of 150 μg were given at three to four week intervals and a final booster (10 μg Flt4 EC in PBS, administered intraperitoneally) was given after another three-week interval. Four days after the final booster dose, the mice were sacrificed and mouse splenic lymphoid cells were fused with SP 2/0 plasmacytoma cells at a 2:1 ratio, respectively.

The fused cells were harvested in 96-well culture plates (NUNC) in Ex-Cell 320 medium (SERALAB) containing 20% fetal calf serum and HAT supplement (hypoxanthine-aminopterin-thymidine; GIBCO, 043-01060H; diluted 50-fold). Cells were cultured at +37° C., in a 5% $CO_2$ atmosphere. After 10 days, HAT-supplemented medium was changed to HT-supplemented cell culture medium (GIBCO; 043-01065H, diluted 50-fold). HT medium is identical to HAT medium, but lacks aminopterin.

In three weeks, specific antibody production was determined by the antigen-specific ImmunoFluoroMetric Assay, (IFMA), described below in Example 26. The master clones were cloned by limited dilutions as described by Staszewski et al., *Yale Journal of Biology and Medicine*, 57:865-868 (1984). Positive clones were expanded onto 24-well tissue culture plates (NUNC), recloned, and re-tested by the same method. Positive clones were tested by fluorescence-activated cell sorting (FACS).

The stable clones secreted immunoglobulins belonging to the $IgG_1$ class, except one, which produced Ig probably belonging to class IgA. The subclass of monoclonal antibody was determined using rat monoclonal antibody to mouse subclass as biotin conjugate (SEROTEC) in IFMA.

Balb/c mice were used to produce monoclonal antibodies in ascites fluid. The hybridomas described above were intraperitoneally injected into mice after pretreatment of the animals with pristane (2,6,10,14-tetramethylpentadecan 98%, ALDRICH-CHEMIE D7924 Steinheim, Cat. No. T 2,280-2). 0.5 ml of pristane (i.v.) was injected about two weeks prior to the hybridoma cells. The amount of cells injected were approximately 7.5 to $9 \times 10^6$ per mouse. Ascites was collected 10 to 14 days after injection of the hybridomas.

Fusion II:

Two month old Balb/c mice (female) were immunized by intraperitoneal injection of the recombinantly produced Flt4 extracellular domain protein (20 µg/mouse), emulsified with Freund's complete adjuvant. Booster injections of 20 µg were given at three to four week intervals and a final booster (10 µg Flt4 in PBS, administered i.v.) was given after another three-week interval. Four days after the final booster dose, the mice were sacrificed and mouse splenic lymphoid cells were fused with SP 2/0 plasmacytoma cells at a 2:1 ratio, respectively.

The fused cells were harvested in 96-well culture plates (FALCON) in OptiMEM 1 (with Glutamax, 1, 51985-026, GIBCO BRL) medium containing 20% fetal calf serum and HAT supplement (hypoxanthine-aminopterin-thymidine, GIBCO BRL 21060-017; diluted 1:50 fold). Cells were cultured at 37° C., in a 5% $CO_2$ atmosphere. After 10 days, HAT-supplemented medium was changed to HT-supplemental cell culture medium (GIBCO BRL; 41065-012, diluted 1:50-fold).

In three weeks, specific antibody production was determined by the antigen-specific ImmunoFluoroMetric Assay (IFMA) described below in Example 26. The master clones were cloned by limited dilutions as described by Staszewki et al. (1984). Positive clones were expanded onto 24-well tissue culture plates (FALCON), re-cloned, and re-tested by the same method. Positive clones were tested by FACS.

The 2E11 and 6B2 clones secreted immunoglobulins belonging to the $IgG_1$ class, and 2B12 clones produced Ig belonging to subclass IgM. The mouse subclass $IgG_1$ was determined using rat monoclonal antibody against mouse subclass heavy chain as biotin conjugate (SEROTEC) in IFMA and the mouse subclass IgM was determined with Mouse Monoclonal Antibody Isotyping Kit (Dipstick Format) (19663-012, Life Technologies Inc.).

Example 26

Specificity of Monoclonal Antibodies Against Flt4

The purified, recombinant Flt4 extracellular domain-6× His fusion product (produced as described in Examples 14 and 25) was labelled with Europium according to Mukkala et al., *Anal. Biochem*, 176(2):319-325 (1989), with the following modification: a 250 times molar excess of isothiocyanate DTTA-Eu (N1 chelate, WALLAC, Finland) was added to the Flt4 solution (0.5 mg/ml in PBS) and the pH was adjusted to about 9 by adding 0.5 M sodium carbonate buffer, pH 9.8. The labelling was performed overnight at +4° C. Unbound label was removed using PD-10 (PHARMACIA, Sweden) with TSA buffer (50 mM Tris-HCl, pH 7.8, containing 0.15 M NaCl) as eluent.

After purification, 1 mg/ml bovine serum albumin (BSA) was added to the labelled Flt4 and the label was stored at +4° C. The average number of Europium ions incorporated per Flt4 molecule was 1.9, as determined by measuring the fluorescence in a ratio to that of known $EuCl_3$ standards (Hemmilä et al., *Anal. Biochem.*, 137:335-343 (1984)).

The antibodies produced in Example 25 were screened using a Sandwich-type immunofluorometric assay, using microtitration strip wells (NUNC, polysorb) coated with rabbit anti-mouse Ig (Z 259, DAKOPATTS). The pre-coated wells were washed once by Platewash 1296-024 (WALLAC) with DELFIA wash solution. The DELFIA assay buffer was used as a dilution buffer for cell culture supernatants and for serum of the splenectomized mouse (at dilutions between 1:1000 to 1:100,000) used as positive control in the preliminary screening assay.

An overnight incubation at +4° C. (or alternatively for 2 hours at room temperature) was begun by shaking on a Plateshake shaker (1296-001, WALLAC) for 5 minutes followed by washing four times with wash solution as described above.

The Europium-labelled Flt4 was added at a dilution of 1:500 in 100 µl of the assay buffer. After 5 minutes on a Plateshake shaker and one hour incubation at room temperature, the strips were washed as described above.

Enhancement solution (DELFIA) was added at 200 µl/well. The plates were then shaken for 5 minutes on a Plateshake shaker and the intensity of fluorescence was measured by ARCUS-1230 (WALLAC) for 10-15 minutes. (Lövgren et al., In: Collins W. P. (Ed.) Alternative Immunoassays, John Wiley & Sons Ltd. (1985), pp. 203-216). The DELFIA results show that all monoclonal antibodies tested bound the Flt4 EC antigen. Monoclonal antibodies reactive with the Flt4 (and the hybridomas which produce the antibodies) were selected for further screening.

The resulting monoclonal antibodies were used in double antibody immunofluorescence staining of NIH3T3 cells expressing the LTR-FLT41 construct and neomycin-resistant transfected NIH3T3 cells. The cells were detached from the culture plates using EDTA, stained, and analysed in a fluorescence-activated cell sorter (FACS). The results of FACS analysis are given as percentages of cells staining positive with the indicated monoclonal antibody (see Table 2, below).

TABLE 2

| Mab clones | LTR %[a] | NEO %[b] | DELFIA-counts |
|---|---|---|---|
| 1B1 | 67.3 | 1 | 20625 |
| 1B1D11 | 75 | 1.2 | 19694 |
| 1B1F8 | 76.1 | 1.4 | 18580 |
| 4F6 | 69.9 | 1.2 | 23229 |
| 4F6B8G12 | 75 | 0.3 | 24374 |
| 4F6B8H11 | 75.9 | 0.3 | 28281 |
| 4F6B8E12 | 74.8 | 0.4 | 27097 |
| 4F6B8G10 | 75.3 | 0.4 | 26063 |
| 9D9 | 45.1 | 0.75 | 17316 |
| 9D9D10 | 71.7 | 2.3 | 18230 |
| 9D9F9 | 73 | 1.8 | 11904 |
| 9D9G6 | 74.3 | 2.9 | 16743 |
| 9D9G7 | 70.7 | 1.3 | 17009 |
| 10E4 | 24.2 | 1.4 | 39202 |
| 10E4B10E12 | 32.3 | 0.3 | 42490 |
| 10E4B10G10 | 36.5 | 0.3 | 54815 |
| 10E4B10F12 | 45.6 | 0.4 | 43909 |
| 10E4B10G12 | 45.7 | 0.5 | 35576 |
| 11G2 | 30.2 | 1.6 | 11304 |
| 11G2D12 | 74.4 | 1.5 | 14660 |

TABLE 2-continued

| Mab clones | LTR %[a] | NEO %[b] | DELFIA-counts |
|---|---|---|---|
| 11G2G9 | 74.2 | 0.9 | 10283 |
| 11G2H7 | 74.4 | 2.1 | 25382 |

[a] FACS results with LTR transfected cells
[b] FACS results with NEO cells (control)

The FACS results with LTR-FLT41-transfected cells indicate that the antibodies effectively recognize Flt4-expressing cells. These same antibodies give only background staining of neomycin phosphotransferase-transfected NIH3T3 cells. Thus, the antibodies specifically recognize the Flt4 tyrosine kinase on the cell surface.

One clone, designated anti-Flt4 hybridoma 9D9F9, was found to stably secrete monoclonal antibody which was determined to be of immunoglobulin class $IgG_1$ by IFMA. Hybridoma 9D9F9 was deposited with the German Collection of Microorganisms and Cell Cultures, Department of Human and Animal Cell Cultures and Viruses, Mascheroder Weg 1b, 3300 Braunschweig, Germany, Mar. 23, 1995, and given accession No. ACC2210.

Fusion II Antibodies

The Europium-labelled Flt4 extracellular domain protein described above also was used to screen the Fusion II antibodies described in Example 25. The antibodies were screened using a Flt4-specific IFMA using microtitration wells (Nunc, Polysorb) coated with rabbit anti-mouse Ig (Z 259, DAKO). The precoated wells were washed once with wash solution (Wallac) by using DELFIA Plate wash.

The DELFIA assay buffer was used as dilution buffer for cell culture supernatants (dilution 1:2 in preliminary screening) and for serum of the splenectomized mouse (dilutions 1:1000 to 1:100,000) which was used as a positive control. As standard, the purified anti-Flt4 9D9F9 (mouse subclass $IgG_1$) was used at concentrations between 1.0 ng/ml and 250 ng/ml. Samples were first shaken at room temperature for five minutes on a Plateshake shaker and then incubated approximately 18 hours at +4° C. The frames were first washed four times, then the Eu-labelled Flt4 (1:2000, in 100 μl assay buffer) was added, and finally the frames were incubated for one hour at room temperature. After washing as described, the enhancement solution. (200 μl/well, Wallac) was added, and the frames were shaken for 5 minutes on the Plateshake shaker. The intensity of fluorescence was measured by ARCUS-1230 (Wallac). Monoclonal antibodies reactive with Flt4 were selected for further screening in the double antibody immunofluorescence staining assay employing Flt4-expressing NIH3T3 cells, as described above.

The resulting Fusion II monoclonal antibodies against Flt4 and corresponding results of FACS analysis (expressed as percentages of cells staining positive with the indicated monoclonal antibody) are summarized in Table 3.

A standard curve for quantitation of anti-Flt4 antibodies was made by using affinity purified anti-Flt4 9D9F9. The linear range reached from 1.0 ng/ml to 250 ng/ml.

Cell lysate of NIH3T3 cells co-tranfected with pLTR-FLT41 construct expressing full-length Flt4 on the surface was electrophoresed in 6.5% SDS-PAGE, proteins were transferred onto nitrocellulose nitrate membrane (0.45 μm, SCHLEICHER & SCHUELL) and immunoblotted with monoclonal antibody-containing hybridoma cell culture supernatants (1:10, 50 mM TRIS-40 mM glycine buffer containing methanol 4%, SDS 0.04%). The specificities of monoclonal antibodies were detected using incubation with HRP-conjugated rabbit antimouse Ig (P 161, DAKO, diluted 1:1000 in 20 mM TRIS buffer, pH 7.5, containing 150 mM saline, 5% milk powder) and ECL (Enhanced chemiluminescence, AMERSHAM).

TABLE 3

| Mab clones | LTR %[a] | NEO[b] | approx. Mab production ng/ml/$10^6$ cells[c] | WB |
|---|---|---|---|---|
| 2B12E10 | 39.5 | 6.0 | 440 | + |
| 2E11D11 | 44.6 | 8.8 | 110 | + |
| 2E11F9 | 49.5 | 4.5 | 100 | + |
| 2E11F12 | 46.0 | 4.1 | 180 | + |
| 2E11G8 | 41.2 | 7.8 | 160 | + |
| 6B2E12 | NF | NF | 1390 | + |
| 6B2F8 | NF | NF | 470 | + |
| 6B2G6 | NF | NF | 630 | + |
| 6B2H5 | NF | NF | 740 | + |
| 6B2H8 | NF | NF | 1800 | + |

[a] FACS results with LTR transfected cells
[b] FACS results with NEO cells (control)
[c] quantitation of Mab production based on affinity-purified antiFLT 9D9F9 antibody used as standard
NF not functioning in FACS
WB Used successfully in Western immunoblotting Example 27

Use of Anti-Flt4 Antibodies to Identify Flt4 in Cell Lysates and Expressed in Lymphatic Endothelial Cells in Human Tissue The monoclonal antibodies produced by hybridoma 9D9 described in the preceding examples were used in immunoprecipitation and Western blotting of lysates of HEL cells. As reported in Example 6, Flt4 mRNA expression had been previously observed in HEL cells. About $2 \times 10^7$ cultured HEL cells were lysed in RIPA buffer specified in Example 11 and immunoprecipitated with about 2 micrograms of the 9D9 antibody (as described for polyclonal antibodies in example 11). For Western analysis, immunoprecipitates were electrophoresed via SDS-PAGE (6% gel) and electroblotted onto a nitrocellulose membrane. Polypeptide bands of 175 kD and 125 kD, corresponding to Flt4 polypeptides, were detected in the Western blotting analysis of the immunoprecipitates using a 1 microgram/ml dilution of the 9D9 antibody.

Immunostaining of human skin tissue was performed using the 9D9 monoclonal antibodies and an alkaline phosphatase ABC-AP kit (Dako). Briefly, slides containing 6 μm samples of adult human skin were dried for 30 minutes at room temperature (RT), fixed for ten minutes with cold acetone, and then washed once for five minutes with phosphate-buffered saline (PBS). The samples were then incubated for 30 minutes at RT with 2% horse serum and washed three times for five minutes in PBS.

For immunostaining, the samples were incubated for one hour at RT with the 9D9 primary antibody and washed three times for five minutes with PBS. After washing, the samples were incubated for thirty minutes at RT with biotinylated rabbit anti-mouse secondary antibodies, and again washed three times for five minutes with PBS.

Bound antibodies were detected by incubating the samples for thirty minutes at RT with ABC-AP complex, washing three times with PBS, incubating for fifteen minutes at RT with AP-substrate (Sigma Fast Red TR/Naphtol AS-MX (Cat. No. F-4648)), and rinsing with water. Samples were then counter-stained with Mayer's hematoxylin for thirty seconds and rinsed with water. Aquamount and a coverslip were applied, and the samples were analyzed under a microscope. The 9D9 antibody staining was observed in lymphatic endothelial cells in these human skin sections. Blood vessel endothelia showed extremely weak or no staining. Additional analyses have served to confirm the apparent specificity for lymphatic endothelia. See Lymboussaki et al., *Am. J. Pathol.*, 153(2):395-403 (August, 1998); and Jussila et al., *Cancer Res.*, 58:1599-1604 (April, 1998), both of which are incorporated herein by reference in their entireties.

These results further confirm the utility of Flt4 as a useful marker for lymphatic endothelia and the utility of anti-Flt4 antibodies for identifying and visualizing Flt4 expressed in these cells, in a tissue sample.

Example 28

Upregulation of the VEGF-C/VEGFR-3 Signalling Pathway in Breast Cancer Angiogenesis The foregoing examples demonstrate that Flt4 (VEGFR-3) is useful as a specific antigenic marker for lymphatic endothelia in normal tissues. The following procedures additionally demonstrate that VEGFR-3 is useful as an antigenic marker (e.g., for diagnosis and screening) and as a therapeutic target in malignant breast tumors. A highly elevated number of VEGFR-3 positive vessels was found in invasive breast cancer in comparison to histologically normal breast tissue ($P<0.0001$).

Materials and Methods

Freshly frozen breast tissue samples were retrieved from the files of the Department of Pathology, University of Helsinki. The samples consisted of ductal carcinoma (n=6), lobular carcinoma (n=6), intraductal carcinoma (n=8), fibroadenoma (n=4), and histologically normal breast tissue (n=12). All samples had been frozen immediately after surgical excision in liquid nitrogen, and stored at $-70°$ C.

Mouse monoclonal antibodies (Mabs) against human Flt4 (VEGFR-3) were produced essentially as described in preceding examples, e.g., Example 25. The VEGFR-3 extracellular protein domain (VEGFR-3EC) was expressed via a recombinant baculovirus in insect cells, purified from the culture medium. Mouse monoclonal antibodies against VEGFR-3EC were then produced using standard methods and the immunoglobulin fraction was purified by protein A affinity chromatography from hybridoma ascites fluid or Tecnomouse® culture supernatants.

Five μM cryosections of the tissues samples were air-dried and fixed in cold acetone for 10 minutes. The sections were re-hydrated in phosphate buffered saline (PBS) and incubated for 30 minutes in 5% normal horse serum at room temperature. The sections were then incubated for 2 hours in a humid atmosphere at room temperature with the Mabs 9D9F9 (Example 26) at the concentration of 1.0 μg/ml. Other anti-VEGFR-3 Mab against distinct epitopes of the VEGFR-3EC were also studied; clones 2E11D11 (Example 26) and 7B8F9 (made essentially as described in Example 26) were used at the concentrations of 9.5 and 8.5 μg/ml, respectively. A subsequent incubation for 30 minutes in biotinylated anti-mouse serum was followed by a 60 minute incubation using reagents of the Vectastain Elite Mouse IgG ABC kit (Vector laboratories, Burlingame, USA). Peroxidase activity was developed with 3-amino-9-ethyl carbazole (AEC, Sigma, St. Louis, USA) for 10 minutes. Finally, the sections were stained with haematoxylin for 20 seconds. Negative controls were performed by omitting the primary antibody, or by using irrelevant primary antibodies of the same isotype. The purified baculoviral immunogen was used to block the binding of the 9D9 antibodies as another negative control. In these experiments, the antibodies were incubated overnight with a 10-fold molar excess of the VEGFR-3EC protein in PBS. After centrifugation for 4 minutes at 4000 rpm, $+4°$ C., the supernatant was carefully collected and then used as primary antibody. The 5 μm cryosections adjacent to the ones stained with the anti-VEGFR-3 antibodies were immunostained for the blood vascular endothelial marker PAL-E (0.15 μg/ml, Monosan, Uden, the Netherlands), laminin (1:4000 dilution of the supernatant of clone LAM-89, Sigma, St Louis, Mo.), collagen XVIII (1.9 μg/ml), α-smooth muscle actin (SMA, 0.5 μg/ml, clone 1A4, Sigma), VEGFR-1 (1:200 dilution of the supernatant of clone 19) or VEGFR-2 (dilution 1:100).

Pathological examination of all of the samples was performed after the staining procedures. The blood vascular densities were obtained from the slides stained for PAL-E [de Waal et al., *Am. J. Pathol.*, 150: 1951-1957 (1997)], following the guidelines recommended by Gasparini and Harris. [Gasparini G, and Harris A, *J. Clin. Oncol.*, 13: 765-782 (1995).] The VEGFR-3 positive vessel densities were studied in the same way. A slide was first scanned at low magnification, and intratumoral vessel density was then assessed by counting the number of stained vessels per a 400× magnification high power field (hpf) in the areas with the highest vascular density ("vascular hotspots") or in the areas with highest VEGFR-3 positive vessel density. A minimum of 5 fields was counted per a slide, after which the 3 highest counts were averaged.

Double staining was performed to differentiate immunohistochemical staining of lymphatic and blood vessels in two intraductal carcinomas. Acetone-fixed cryosections were incubated for 1 hour with anti-PAL-E antibodies, with biotinylated horse anti-mouse antibody (Vectastain Elite Mouse IgG ABC kit, Vector laboratories, Burlingame, USA) for 30 minutes, with ABC-peroxidase (Vectastain, 1:100) for 45 minutes, and developed finally with AEC for 10 minutes. For the second step, the sections were incubated with anti-VEGFR-3 antibodies for 1 hour (0.14 μg/ml), followed by biotinylated anti-mouse antibody for 30 minutes (1:200 dilution of the supernatant of clone), ABC-peroxidase for 30 minutes (1:100), biotinylated tyramin solution (1:2.000) containing 0.01% peroxide for 5 minutes, ABC-alkaline phosphatase (1:100) for 20 minutes, and developed With Fast Blue (Sigma, St. Louis, USA) for 20 minutes, according to a procedure previously described in the literature for ISH signal enhancement. [Kerstens et al., *J. Histochem. Cytochem.*, 43: 347-352 (1995).] Cryosections (5 μm) adjacent to the double-stained sections were also immunostained with VEGFR-3 antibodies only; as described above.

Polyclonal antibodies were produced in rabbits against a synthetic peptide corresponding to the amino acid residues 2-18 of the N-terminus of mature, secreted human vascular endothelial growth factor C (VEGF-C) (residues 104-120 of the VEGF-C prepro-VEGF-C polypeptide) as described in the literature. [Joukov et al., *EMBO J.*, 16: 3898-3911 (1997), incorporated herein by reference in its entirety.] The antisera were affinity-purified using the immunogenic polypeptide coupled to an epoxy-activated sepharose-6B column and tested for specific staining of VEGF-C using cells infected with an adenoviral vector expressing VEGF-C or control β-galactosidase.

The eight intraductal carcinomas and all of the invasive carcinomas analysed for VEGFR-3 were chosen for further analyses of the expression of VEGF-C. Five micrometer cryosections adjacent to the sections stained with the anti-VEGFR-3 antibodies were air-dried and fixed in cold acetone for 10 minutes. The sections were rehydrated in PBS and incubated for 30 minutes in 5% normal goat serum and then for 2 hours in a humid atmosphere at room temperature with the rabbit polyclonal antibodies against human VEGF-C, diluted 1:200 in PBS. A subsequent incubation for 30 minutes in biotinylated anti-rabbit serum was followed by a 60 minutes incubation using reagents of the Vectastain Elite Rabbit IgG ABC kit (Vector laboratories, Burlingame, USA). The sections were further processed as described above. As a negative control, the purified immunogen was used to block the binding of the VEGF-C antibodies. In these experiments, VEGF-C antibodies were incubated overnight with a 10-fold molar excess of the VEGF-C protein in PBS. After centrifugation for 4 minutes at 4000 rpm at +4° C., the supernatant was carefully collected and used in the immunostainings.

Monoclonal antibodies to human type XVIII collagen were generated by DiaBor Ltd. (Oulu, Finland) by immunization of mice with the recombinant polypeptide QH48.18 [Saarela et al., *Matrix Biology*, 16: 319-28 (1998)], corresponding to the common region of the N-terminal NC1 domain of human type XVIII collagen. The clones were screened by ELISA assay and Western analysis using the polypeptide QH48.18, and also by immunofluorescence staining of frozen human tissue sections. The screening of the hybridoma clones resulted in three monoclonal antibodies, which were positive in all three assays mentioned (ELISA, Western, immunofluorescence staining). One of the antibodies which gave the strongest signals, DB144-N2, was used in subsequent experiments. It gave an identical staining pattern (e.g., in adult human skin and kidney samples) to that of the polyclonal anti-all hu(XVIII).

Results

A. VEGFR-3 in Histologically Normal Breast Tissue and in Benign Fibroadenomas

Immunohistochemical staining of VEGFR-3 in normal breast tissue showed a very weak staining in capillaries of the interductal stroma. These vessels did not form any specific pattern, but were scattered throughout the stroma. The density of the VEGFR-3 positive vessels in the normal breast tissue samples ranged from 6 to 17 per hpf, median 9 (n=12). Most of such vessels were strongly stained for the blood vascular endothelial marker PAL-E and for the basal lamina component, collagen XVIII, suggesting that VEGFR-3 was expressed weakly in the blood vessels of normal breast tissue. However, some thin vessels in the stroma, which were clearly stained for VEGFR-3 were negative for PAL-E and only weakly positive for the collagen type XVIII, suggesting that they were lymphatic vessels. VEGFR-3 positive vessels were also uniformly found in benign fibroadenomas, where their density (median 8 vessels per hpf; range 3-19; n=4) did not differ from that of the histologically normal breast tissue (median 8 vs. 9; P>0.1, the Mann-Whitney test).

B. VEGFR-3 Positive Vessels in Intraductal Carcinomas

Figures 5E, 5F:
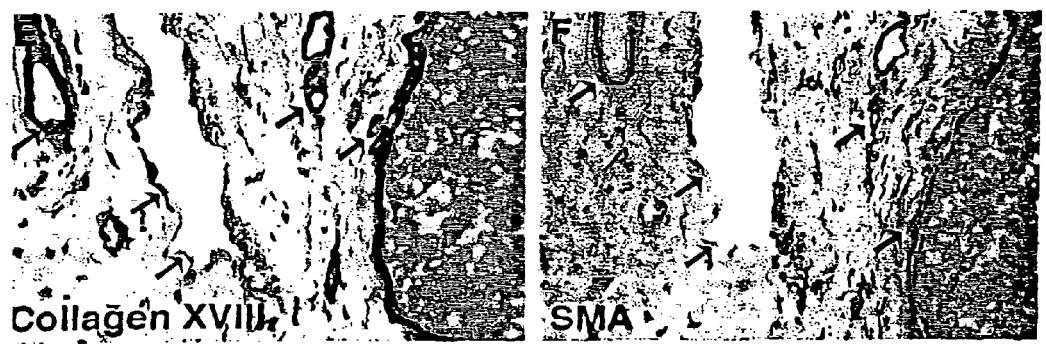
Figures 5G, 5H:
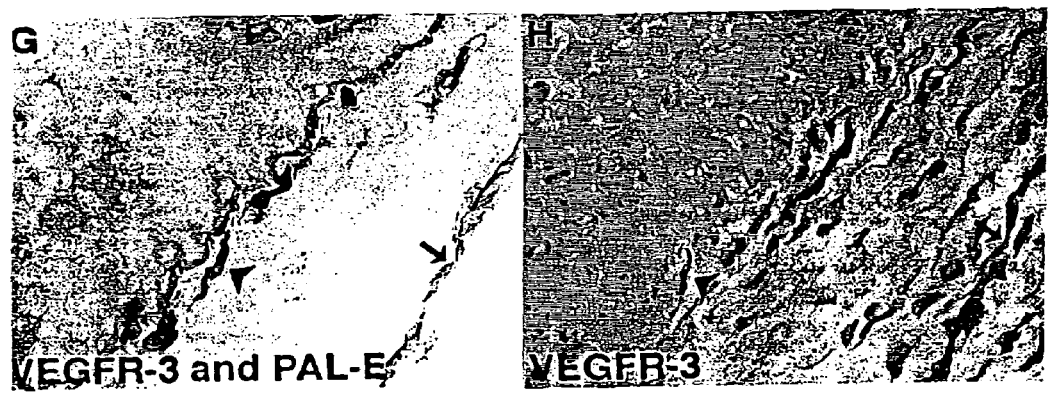

In intraductal carcinomas, a distinctive pattern of strongly-stained VEGFR-3 positive vessels was observed. The vessels formed arch-like structures around the affected ducts (FIG. 5A). This "necklace" pattern also was observed in staining of adjacent sections for the blood vessel endothelial marker, PAL-E (FIG. 5B), suggesting that VEGFR-3 expression was enhanced in capillary endothelium. In order to more definitively differentiate between blood and lymphatic vessels and to search for the presence of smooth muscle cells and pericytes in the vessel walls, additional stainings were done using antibodies against smooth muscle α-actin (SMA) and basal lamina components laminin and type XVIII collagen. According to this staining, the small vessels close to the intraductal carcinomas expressed simultaneously VEGFR-3 and the basal lamina proteins, but stained more weakly for SMA, indicating that they are incompletely covered by pericytes/smooth muscle cells in the vessel wall (black arrows in FIGS. 5C-5F). In contrast, larger blood vessels at some distance from the intraductal lesions were in general negative for VEGFR-3, but positive for laminin, collagen XVIII and SMA (red arrows). In addition, vessels were found, which were positive for VEGFR-3, but only very weakly stained for the basal lamina proteins laminin and type XVIII collagen and not at all for SMA (green arrows). These were considered to represent lymphatic vessels.

C. Differential Double-Staining of Blood and Lymphatic Vessels

Two intraductal carcinomas were chosen for the immunohistochemical double-staining procedure to more clearly differentiate lymphatic vessels from blood vessels. [See de Waal et al., *Am. J. Pathol.*, 150: 1951-1957 (1997).] Using this method, the VEGFR-3 positive vessels were stained blue, while the PAL-E positive vessels and basal laminae were stained brown. Both tested samples showed a similar pattern of staining: the vessels lining the tumor filled ducts were predominantly PAL-E positive (arrowhead in FIGS. 5G and 5H) while the presumably lymphatic, VEGFR-3 positive vessels a short distance away in the interductal stroma were PAL-E negative (black arrows in FIGS. 5G and 5H). In order to exclude misinterpretation due to possible double-staining artefacts, adjacent 5 μm sections were stained with anti-VEGFR-3 alone. This staining confirmed that several of the PAL-E positive blood vessels are also positive for VEGFR-3.

D. VEGF-C, VEGFR-1, and VEGFR-2 in the Intraductal Carcinoma Cells and its Receptors in Adjacent Vessels Polyclonal affinity-purified antibodies against human VEGF-C were used to stain the 8 intraductal carcinoma samples. All tested samples contained at least some VEGF-C, but considerable heterogeneity was observed in the intensity of staining and in the expression patterns. In some cases, most of the carcinoma cells were strongly positive for VEGF-C, while in others, only some carcinoma cells gave a staining signal. In contrast, very little or no staining was observed in the normal tissues surrounding the affected ducts, although weak signal was also obtained in unaffected normal ductal epithelium. Antigen blocking experiments indicated that the staining for VEGF-C was specific. The other VEGF-C receptor, VEGFR-2, as well as the other VEGF receptor (VEGFR-1), were both expressed in the same "necklace" vessels adjacent to the intraductal carcinoma cells.

E. VEGFR-3 Positive Vessels and VEGF-C in Invasive Breast Carcinoma

Strongly-stained VEGFR-3 positive vessels were also present in all invasive ductal carcinomas and lobular carcinomas studied. The VEGFR-3 positive vessels did not appear to form any specific distribution pattern; most of these vessels were also immunoreactive for the PAL-E antigen. The intratumoral VEGFR-3 positive vessel density (median 21, range 9-56 vessels per hpf; n=12) was significantly elevated in the invasive breast carcinomas when compared with normal breast tissue (median 21 vs. 9; P<0.0001, the Mann-Whitney test). Occasionally, invasion of the carcinoma cells into the VEGFR-3 positive lymphatic vessels could be observed.

Immunostaining for VEGF-C varied strongly among the invasive carcinomas studied (n=12). Some carcinoma cells were strongly positive for VEGF-C, while others stained very weakly or, in some cases, no staining was observed. Like in the intraductal carcinomas, very little or no staining was observed in the connective tissue in these sections.

The foregoing data reveals that VEGFR-3, which had otherwise appeared to be a predominantly lymphatic endothelial marker in most adult tissues, is very weakly expressed also in capillary endothelium of normal breast tissue. More significantly, in intraductal carcinomas, a "necklace" pattern of strongly-stained VEGFR-3 positive vessels was detected lining the tumor-filled ducts. Most of these vessels expressed the blood vessel endothelial marker PAL-E and the basal lamina components laminin and collagen XVIII, but apparently had less pericytes/smooth muscle cells than blood vessels located further away from the tumor cells, as shown by staining using antibodies against SMA. These features suggest that the "necklace" vessels were undergoing angiogenesis. A second group of vessels lying a distance away from the affected ducts were positive for VEGFR-3 but very weakly positive for the basal lamina components and negative for PAL-E, suggesting that they are lymphatic vessels. These vessels also lacked SMA-positive pericytic components. Also in invasive breast carcinomas, VEGFR-3 was upregulated in PAL-E positive blood vessels, although the vessel patterns seen were more randomly organized in the connective tissue stroma around the tumor cells. The results indicate that VEGFR-3 expression is upregulated in breast carcinomas during angiogenesis associated with tumor growth. The highly elevated number of VEGFR-3 positive vessels found in carcinoma in situ is compatible with the hypothesis that the carcinoma cells produce factors, which activate the growth of blood vessels in the immediate vicinity of the carcinoma cells.

Since VEGF-C binds both VEGFR-3 and VEGFR-2 with high affinity, and since both intraductal and invasive carcinoma cells often stained positive for VEGF-C protein, this growth factor is a candidate growth factor for the VEGFR-3 and VEGFR-2 positive vessels in the carcinomas. These data are in agreement with another study, in which nearly half of thirty-five unselected malignant invasive tumors (including breast carcinomas, squamous cell carcinomas, lymphomas, melanomas, and sarcomas) contained VEGF-C mRNA in Northern blotting analyses. [See Salven et al., *Am. J. Pathol.*, 153(1): 103-108 (July, 1998), incorporated herein by reference in its entirety.] Collectively, the data reported herein provide an indication for treatment of breast carcinomas and possibly other, non-lymphatic carcinomas with agents that block the VEGF-C mediated stimulation of VEGFR-3 and/or VEGFR-2. Contemplated blocking agents include: anti-VEGF-C antibodies; anti-VEGFR-3 antibodies; anti-VEGFR-2 antibodies; bispecific antibodies that bind to VEGFR-3 and either VEGFR-2 or VEGFR-1; soluble extracellular domain fragments of VEGFR-3 that will bind circulating VEGF-C; VEGF-C fragments and analogs that bind VEGFR-3 and/or VEGFR-2 and that inhibit activation of such receptors; VEGF-C polypeptides, fragments, and analogs that bind VEGFR-3 and/or VEGFR-2 and that are conjugated to a suitable therapeutic agent; VEGFR-3 tyrosine kinase inhibitors; and small molecules that bind and inhibit these receptors. In addition, since VEGF-D binds both VEGFR-3 and VEGFR-2, it is contemplated that anti-VEGF-D antibodies and inhibitory VEGF-D fragments and analogs are suitable blocking agents. Human or humanized antibodies and fragments thereof are preferred, to the extent that antibody agents are selected for human therapy. Additionally, it is contemplated, as an additional aspect of the invention, to use any of the foregoing agents to evaluate mammalian tissue in vitro or in vivo, e.g., for the purposes of diagnosis and screening for malignancies and the spread of malignancies.

For any of the foregoing agents, it is contemplated that the agent may be further improved for diagnosis and screening by the attachment of a detectable label, including but not limited to radioisotopes (e.g.; $^{14}C$, $^{133}I$ and $^{125}I$), chromophores (e.g., fluorescein, phycobiliprotien; tetraethyl rhodamine; enzymes which produce a fluorescent or colored product for detection by fluorescence; absorbance, visible color, or agglutination, which produces an electron-dense product for detection by electron microscopy); or electron dense molecules such as ferritin, peroxidase, or gold beads. Likewise, the agents may be further improved for therapeutic purposes by attachment (e.g., conjugation) or co-administration with molecules having anti-neoplastic properties, such as toxins of plant, animal, microbial, or fungal origin; radioisotopes; drugs; enzymes; and/or cytokines and other therapeutic proteins. (See, e.g., Pietersz & McKenzie, "Antibody Conjugates for the treatment of Cancer," *Immunological Reviews,* 129:57-80 (1992), incorporated by reference herein.

Example 29

Anti-Flt4 Antibodies for Administration as a Therapeutic to Humans

A. Humanization of Anti-Flt4 Monoclonal Antibodies

The biology of Flt4 as reported herein, e.g., in Example 28, indicates therapeutic uses for Flt4 inhibitors (antagonists) that block ligand-mediated signalling of the Flt4 receptor. Flt4-neutralizing antibodies comprise one class of therapeutics useful as Flt4 antagonists. Following are protocols to improve the utility of anti-Flt4 monoclonal antibodies as therapeutics in humans, by "humanizing" the monoclonal antibodies to improve their serum half-life and render them less immunogenic in human hosts (i.e., to prevent human antibody response to non-human anti-Flt4 antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest, such as the anti-Flt4 monoclonal antibodies described herein, with the constant domains of human antibody molecules. (See, e.g., Morrison and Oi, *Adv. Immunol.*, 44:65-92 (1989).) The variable domains of Flt4 neutralizing anti-Flt4 antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. [See, e.g., Jones et al., *Nature,* 321:522-525 (1986); Riechmann et al., *Nature,* 332:323-327 (1988); Verhoeyen et al., *Science.* 239: 1534-36 (1988); and Tempest et al., *Bio/Technology,* 9:266-71 (1991).] If necessary, the β-sheet framework of the human antibody surrounding the CDR3 regions also is modified to more closely mirror the three dimensional structure of the antigen-binding domain of the original monoclonal antibody. (See Kettleborough et al., *Protein Engin.*, 4:773-783 (1991); and Foote et al., *J. Mol. Biol.,* 224:487-499 (1992).)

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, *Molecular Immunol.*, 28(4/5):489-98 (1991).

The foregoing approaches are employed using Flt4-neutralizing anti-Flt4 monoclonal antibodies and the hybridomas that produce them, such as antibodies 9D9F9, to generate humanized Flt4-neutralizing antibodies useful as therapeutics to treat or palliate conditions wherein Flt4 expression is detrimental.

B. Human Flt4-Neutralizing Antibodies from Phage Display

Human Flt4-neutralizing antibodies are generated by phage display techniques such as those described in Aujame et al., *Human Antibodies*, 8(4):155-168 (1997); Hoogenboom, TIBTECH, 15:62-70 (1997); and Rader et al., *Curr. Opin. Biotechnol.* 8:503-508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is panned (screened) for Flt4-specific phage-antibodies using labelled or immobilized Flt4 as antigen-probe.

C. Human Flt4-Neutralizing Antibodies from Transgenic Mice

Human Flt4-neutralizing antibodies are generated in transgenic mice essentially as described in Bruggemann and Neuberger, *Immunol. Today*, 17(8):391-97 (1996) and Bruggemann and Taussig, *Curr. Opin. Biotechnol.*, 8:455-58 (1997). Transgenic mice carrying human V-gene segments in germline configuration and that express these transgenes in their lymphoid tissue are immunized with an Flt4 composition using conventional immunization protocols. Hybridomas are generated using B cells from the immunized mice using conventional protocols and screened to identify hybridomas secreting anti-Flt4 human antibodies (e.g., as described above).

D. Bispecific Antibodies

Bispecific antibodies that specifically bind to Flt4 and that specifically bind to other antigens relevant to pathology and/or treatment are produced, isolated, and tested using standard procedures that have been described in the literature. See, e.g., Pluckthun & Pack, *Immunotechnology*, 3:83-105 (1997); Carter et al., *J. Hematotherapy*, 4: 463-470 (1995); Renner & Pfreundschuh, *Immunological Reviews*, 1995, No. 145, pp. 179-209; Pfreundschuh U.S. Pat. No. 5,643,759; Segal et al., *J. Hematotherapy*, 4: 377-382 (1995); Segal et al., *Immunobiology*. 185: 390-402 (1992); and Bolhuis et al., *Cancer Immunol. Immunother.*, 34: 1-8 (1991), all of which are incorporated herein by reference in their entireties.

Example 30

Animal Models to Demonstrate the Efficacy of Anti-Flt4 Therapies for Treatment of Cancers It is contemplated that any accepted animal for cancer therapies would be useful to demonstrate the efficacy of anti-Flt4 therapies for cancer treatment. Exemplary models for demonstrating the efficacy for treatment of breast cancers, using standard dose-response studies, include those described in Tekmal and Durgam, *Cancer Lett.*, 118(1): 21-28 (1997); Moshakis et al., *Br. J. Cancer*, 43: 575-580 (1981); and Williams et al., *J. Nat. Cancer Inst.*, 66: 147-155 (1981). In addition to murine models, dog and pig models are contemplated because at least certain anti-human Flt4 antibodies (e.g., the 9D9 antibodies) also recognize Flt4 from dog and pig. Tumor size and side effects are monitored to demonstrate therapeutic efficacy versus controls.

Example 31

Soluble Flt4 Inhibits VEGF-C Mediated Tumor Growth and Metastasis

To further demonstrate the in vivo role of VEGF-C in tumorigenesis, MCF-7 human breast carcinoma cells overexpressing recombinant VEGF-C were orthotopically implanted into SCID mice. The VEGF-C overexpression increased tumor growth but, unlike VEGF-A overexpression, it had little effect on tumor angiogenesis. On the other hand, VEGF-C strongly promoted the growth of tumor associated lymphatic vessels, which in the tumor periphery were commonly infiltrated with the tumor cells. These effects of VEGF-C were inhibited by a soluble VEGFR-3 fusion protein. These data indicate that VEGF-C can upregulate tumor growth and/or metastasis via the lymphatic vessels, and that these effects can be inhibited by blocking the interaction between VEGF-C and its receptor(s). In particular, a soluble VEGFR-3/Flt4 can be used to block this interaction.

Materials and Methods

A. Preparation of Plasmid Expression Vectors

The cDNAs coding for the human VEGF-C or $VEGF_{165}$ were introduced into the pEBS7 plasmid (Peterson and Legerski, *Gene*, 107: 279-84, 1991.). The same vector was used for the expression of the soluble receptor chimeras VEGFR-3-Ig, containing the first three immunoglobulin homology domains of VEGFR-3 fused to the Fc-domain of human immunoglobulin γ chain and VEGFR-1-Ig, containing the first five Ig homology domains of VEGFR-1 in a similar construct (Achen, et al., *Proc Natl Acad Sci USA*, 95: 548-53, 1998).

B. Production and Analysis of Transfected Cells

The MCF-7S1 subclone of the human MCF-7 breast carcinoma cell line was transfected with the plasmid DNA by electroporation and stable cell pools were selected and cultured as previously described (Egeblad and Jaattela, *Int J Cancer*, 86: 617-25, 2000). The cells were metabolically labeled in methionine and cysteine free MEM (Gibco) supplemented with 100 µCi/ml [$^{35}$S]-methionine and [$^{35}$S]-cysteine (Redivue Pro-Mix, Amersham Pharmacia Biotech). The labeled growth factors were immunoprecipitated from the conditioned medium using antibodies against VEGF-C (Joukov, et al., *EMBO J*, 16: 3898-911, 1997) or VEGF (MAB293, R & D Systems). The immunocomplexes and the VEGFR-Ig fusion proteins were precipitated using protein A sepharose (Amersham Pharmacia Biotech), washed twice in 0.5% BSA, 0.02% Tween 20 in PBS and once in PBS and analyzed in SDS-PAGE under reducing conditions.

C. Cell Proliferation and Tumorigenesis Assays

Cells (20 000/well) were plated in quadruplicate in 24-wells, trypsinized on replicate plates after 1, 4, 6, or 8 days and counted using a hemocytometer. Fresh medium was provided after 4 and 6 days. For the tumorigenesis assay, sub-confluent cultures were harvested by trypsination, washed twice and $10^7$ cells in PBS were inoculated into the fat pads of the second (axillar) mammary gland of ovariectomized SCID mice, carrying subcutaneous 60-day slow-release pellets containing 0.72 mg 17β-estradiol (Innovative Research of America). The ovarectomy and implantation of the pellets were performed 4-8 days before tumor cell inoculation. Tumor length and width were measured twice weekly in a blinded manner, and the tumor volume was calculated as the length×width×depth×0.5, assuming that the tumor is a hemi-ellipsoid and the depth is the same as the width (Benz et al., *Breast Cancer Res Treat*, 24: 85-95, 1993).

D. Histology and Quantitation of the Blood Vessels

The tumors were excised, fixed in 4% paraformaldehyde (pH 7.0) for 24 hours, and embedded in paraffin. Sections (7 μm) were immunostained with monoclonal antibodies against PECAM-1 (Pharmingen), VEGFR-3 (Kubo et al. *Blood*, 96: 546-553, 2000) or PCNA (Zymed Laboratories) or polyclonal antibodies against LYVE-1 (Banerji et al., *J Cell Biol*, 144: 789-801, 1999), VEGF-C (Joukov et al., *EMBO J*, 16: 3898-911, 1997) or laminin according to published protocols (Partanen et al., *Cancer*, 86: 2406-12, 1999). The average of the number of the PECAM-1 positive vessels was determined from three areas (60× magnification) of the highest vascular density (vascular hot spots) in a section. All histological analysis was performed using blinded tumor samples.

E. Adenoviral Expression of Soluble VEGFR-3 and Evan's Blue Draining Assay

The cDNA coding for the VEGFR-3-Ig fusion protein was subcloned into the pAdBglII plasmid and the adenoviruses produced as previously described (Laitinen et al., *Hum Gene Ther.*, 9: 1481-6, 1998). The VEGFR-3-Ig or LacZ control (Laitinen et al., *Hum Gene Ther.*, 9: 1481-6, 1998) adenoviruses, $10^9$ pfu/mouse, were injected intravenously into the SCID mice 3 hours before the tumor cell inoculation. After 3 weeks, four mice from each group were narcotized, the ventral skin was opened and a few microliters 3% Evan's blue dye (Sigma) in PBS were injected into the tumor. The drainage of the dye from the tumor was followed macroscopically.

Results

A. Expression of VEGF-C or VEGFR-3-Ig does not Affect MCF-7 Cell Growth In Vitro The MCF-7 human breast carcinoma cells were transfected with expression plasmids coding for full length human VEGF-C or a soluble VEGFR-3 fusion protein (VEGFR-3-Ig) as described above and stable cell pools were selected. For comparison, human $VEGF_{165}$ or VEGFR-1-Ig were expressed in the same cells. Immunoprecipitation was used to analyze the conditioned media of these cells for the efficient production and secretion of the proteins. Immunoprecipitates of VEGF-C, VEGF or the soluble receptor proteins from metabolically labeled MCF-7 cells were analyzed in PAGE under reducing conditions.

This investigation revealed that overexpression of VEGF-C, VEGF, soluble VEGFR-3 fusion protein or soluble VEGFR-1 fusion protein does not affect the proliferation of the MCF-7 breast carcinoma cells in vitro. When the cells were seeded in 24-well plates and their growth was measured using hemacytometer, it was found that the growth rate of the transfected cells was not affected.

B. VEGF-C Increases Tumor Growth without Affecting Tumor Angiogenesis

To determine the in vivo effects of VEGF-C, the MCF-7 cell pools were implanted into the mammary fad pads of ovariectomized SCUD mice carrying slow-release estrogen pellets to provide a constant level of the hormone needed to support the growth of the MCF-7 tumors.

Overexpression of VEGF-C increased tumor growth significantly (VEGF-C: 545 $mm^3 \pm 110$ $mm^3$, control: 268 $mm^3 \pm 69$ $mm^3$ at 13 days, n=8, p<0.0001, Student's t-test). However, the effect of VEGF-C overexpression on tumor growth was much less dramatic than that of VEGF-A (VEGF-A: 1136 $mm^3 \pm 339$ $mm^3$, control: 189 $mm^3 \pm 57$ $mm^3$, at 15 days, n=6, p<0.0001, Student's t-test). The increased tumor growth was neutralized by mixing the VEGF-C or VEGF overexpressing MCF-7 cells with cells expressing the soluble VEGFR-3 or VEGFR-1 fusion proteins, respectively. Further, it was found that the increased growth of the VEGF-C overexpressing tumors also was inhibited by a circulating soluble VEGFR-3-Ig expressed in the liver by an intravenously injected recombinant adenovirus.

To investigate the effect of VEGF-C on tumor angiogenesis, sections of the tumors were stained for PECAM-1, an endothelial antigen primarily expressed in blood vessels and only weakly in lymphatic vessels. Quantitation of the PECAM-1 positive vessels in the tumors revealed that overexpression of VEGF-C had very little effect on the density of the tumor blood vessels ($40.2 \pm 12.2$ vessels/microscopic field for VEGF-C tumors, n=18 and $36.6 \pm 11.6$ for control tumors, n=23, average of three different experiments). In contrast, overexpression of VEGF-A increased the vascular density approximately two-fold.

C. VEGF-C Overexpression is Associated with Lymphangiogenesis and Intralymphatic Growth of Tumor Cells The effect of VEGF-C on tumor associated lymphatic vessels was analysed by immunostaining for the lymphatic specific marker LYVE-1 (Banerji et al., *J Cell Biol*, 144: 789-801, 1999.). This marker revealed highly hyperplastic lymphatic vessels in the periphery of the VEGF-C overexpressing tumors. The proliferating cell nuclear antigen (PCNA) was detected in many of the LYVE-1 positive endothelial cells, showing that these lymphatic vessels were actively proliferating. Confirmation of the lymphatic identity of the vessels was obtained by staining for VEGFR-3 and by the lack of staining for the basal lamina component laminin. Thin lymphatic vessels were also present inside some of the VEGF-C overexpressing tumors.

The lymphatic vessels in the tumor periphery were commonly infiltrated by the VEGF-C positive tumor cells. In a striking contrast, the VEGF overexpressing and control tumors contained no or only few lymphatic vessels.

D. VEGF-C Induced Lymphangiogenesis is Inhibited by a Circulating Soluble VEGFR-3 Fusion Protein In human breast cancer, the centinel node method is used to trace lymphatic drainage and metastatic spread (for a review, see Parker et al. *Radiol Clin North Am*, 38: 809-23, 2000). In order to trace lymphatic drainage of the MCF-7 tumors, Evan's blue dye was injected into VEGF-C overexpressing or control tumors in mice infected with VEGFR-3-Ig or control adenovirus. Control experiments indicated that infection of cultured human embryonic kidney cells with the VEGFR-3-Ig adenovirus resulted in the secretion of high amounts of the soluble VEGFR-3-Ig fusion protein and intravenous infection of mice led to high systemic levels of the VEGFR-3-Ig fusion protein in the serum. Injection of Evan's blue dye into the tumors resulted in the staining of lymphatic but not blood vessels and revealed an increased number of enlarged lymphatic vessels surrounding the VEGF-C overexpressing tumors when compared to control tumors. Most of the enlarged lymphatic vessels were absent from VEGF-C overexpressing tumors in mice treated with the VEGFR-3-Ig adenovirus.

The foregoing data demonstrate that VEGF-C overexpression in MCF-7 mammary tumors strongly and specifically induces the growth of tumor associated lymphatic vessels, but does not have major effects on tumor angiogenesis. Furthermore, it demonstrated that VEGF-C-mediated increased tumor growth and tumor-associated lymphangiogenesis were inhibited by a soluble VEGF-R-3 fusion protein, i.e., an agent selected to block VEGF-C-mediated stimulation of endothelial cells that express VEGFR-3.

Due to the lack of specific markers, it has in the past been difficult to determine whether tumors can actively induce lymphangiogenesis or merely encompass the already existing lymphatic vessels by overgrowth and compress them due to the high interstitial fluid pressure inside the tumor. Data from various experimental models has recently suggested the latter occurs (Leu et al., Cancer Res, 60: 4324-7, 2000; Stohrer et al., Cancer Res, 60: 4251-5, 2000.). Here, for the first time, it is shown that overexpression of VEGF-C can induce the growth of lymphatic vessels in association with experimental tumors. The VEGF-C induced lymphatic vessels in the tumor periphery were highly hyperplastic and mostly filled with tumor cells, whereas the lymphatic vessels inside the tumor were flattened and without a lumen. Unlike lymphatic endothelial cells in normal adult tissues, the lymphatic endothelial cells associated with the MCF-7 tumors were actively proliferating. Thus, it would appear that most of the peri- and intratumoral lymphatic vessels were generated by proliferation of the endothelial cells of pre-existing lymphatic vessels.

The spread of cancer through the lymphatics into the regional lymph nodes has long been an important prognostic indicator in clinical use. The growth of tumor cells inside the enlarged lymphatic vessels associated with the VEGF-C-overexpressing tumors as demonstrated in this Example, closely resembles the peritumoral lymphatic invasion, that correlates with metastatic spread to the lymph nodes and poor survival in human breast cancer (Lauria et al., Cancer, 76: 1772-8, 1995). Thus, the data reported herein provides evidence that expression of VEGF-C promotes tumor metastasis via the lymphatic system. Thus, whereas Example 28 and other data indicates that VEGFR-3 is upregulated in the blood vessels of many kinds of solid tumors (Valtola et al., Am J Pathol, 154: 1381-90, 1999; Partanen et al., Cancer, 86: 2406-12, 1999; Kubo et al., Blood, 96: 546-553, 2000), the present Example demonstrates a tumor model wherein overexpression of VEGF-C effects were mainly lymphangiogenic.

The effect of VEGF-C on tumor growth was not simply due to variation between the cell pools, as shown by the ability of the VEGFR-3 fusion protein to inhibit the growth of VEGF-C overexpressing tumors. By injecting Evan's blue dye into the tumors, it was demonstrated that an increased number of large draining lymphatic vessels were associated with the VEGF-C overexpressing tumors. It is possible that the higher number of functional lymphatic vessels may result in a better lymphatic drainage and thus a lower interstitial pressure and enhanced blood perfusion of the VEGF-C overexpressing tumors. Irrespective of whether VEGF-C/D-VEGFR-3 mediated tumor progression for a particular tumor proceeds through angiogenesis lymphangiogenesis, or both, the therapeutic methods of the invention should inhibit these processes.

In conclusion, the results above show that VEGF-C produced by tumor cells can induce the growth of lymphatic vessels around tumors and thus facilitate the intralymphatic spread of cancer. The data indicates that inhibition of tumor associated lymphangiogenesis, for example by gene therapy employing soluble VEGFR-3 proteins, represents a valuable way of inhibiting tumor metastasis.

Example 32

Inhibition of Lymphangiogenesis in Mice Expressing Soluble VEGFR-3/Flt4

The previous Example demonstrated that VEGF-C increased in vivo tumor growth and this promotion of tumor growth of tumor was associated lymphatic vessels. These effects of VEGF-C were inhibited by a soluble VEGFR-3 fusion protein. The present Example provides further evidence that soluble VEGFR-3 is a potent inhibitor of VEGF-C/VEGF-D signaling and, when expressed in the skin of transgenic mice, it inhibits lymphangiogenesis and induces a regression of already formed lymphatic vessels while the blood vasculature remains intact.

More particularly, the present example shows that a chimeric protein consisting of the ligand-binding portion of the extracellular portion of VEGFR-3, joined to the Fc domain of immunoglobulin (Ig) γ-chain (VEGF-R-3-Ig) neutralizes the activity of VEGF-C and VEGF-D and inhibits the formation of the dermal lymphatic vasculature when expressed in mouse epidermis under the keratin-14 (K14) promoter. As the blood vessel network remained normal in these mice, the inhibition appears to be specific to the lymphatic vessels. VEGFR-3-Ig induced regression of lymphatic vessels during embryonic development, indicating that continuous signaling by this receptor is essential for the maintenance of the lymphatic vasculature.

Materials and Methods

A. Production of VEGF-C, VEGF-D and VEGFR-1 g Fusion Proteins

The mature form of human VEGF-C as described above in Example 31 and by Joukov et al., (EMBO J. 16:3898-3911, 1997). VEGF-D was obtained from R&D Systems (Minneapolis, Minn.). The VEGFR-1-Ig and VEGFR-3-Ig proteins consisting of the ligand-binding domains of human VEGFRs fused to human IgG1 Fc domain were produced in Drosophila S2 cells (Invitrogen, Carlsbad, Calif.).

B. VEGFR-3 Bioassay

Ba/F3 cells expressing the VEGFR-3/EpoR chimera (Achen, Eur. J. Biochem. 267, 2505-2515, 2000) were seeded, in 96-well microtiter plates at 15,000 cells/well in triplicates supplied with 100 ng/ml of VEGF-C and with indicated concentrations of VEGFR-Ig proteins. After 48 h, the viability of the cells was determined by adding MTT (3-(4,5-dimethylthiazol-2-yl)-2,5-diphenyl tetrazolium bromide (Sigma), 0.5 mg/ml), followed by further 2 h of culture, addition of an equal volume of cell lysis solution (10% SDS, 10 mM HCl) and incubation overnight at 37° C. Absorbance was measured at 540 nm.

C. Generation of the Transgenic Mice

The sequence encoding human VEGFR-3 Ig-homology domains 1-3 was amplified using PCR. The primers employed for this purpose were: 5'-TACAAAGCTTTTCGC-CACCATGCAG-3' (SEQ ID NO:23) and '5-TACAGGATC-CTCATGCACAATGACCTC-3' (SEQ ID NO:24).

The PCR product was cloned into the plg-plus vector (Ingenius, R&D Systems) in frame with human IgG1 Fc tail. The VEGFR-3-Ig construct was then transferred into the human keratin-14 promoter-expression vector. The expression cassette fragment was injected into fertilized mouse oocytes of the FVB/NIH and DBAxBalbC hybrid strains to create seven lines of K14-VEGFR-3-Ig mice. Transgene expression was analyzed and the phenotype was confirmed from all three founder lines expressing the transgene as described below.

D. Analysis of Transgene Expression

For northern blotting, 10 µg of total RNA extracted from skin in 1% agarose was subjected to electrophoresis, transferred to nylon filters (Nytran), hybridized with the corresponding [$^{32}$P]-labeled cDNA probes and exposed autoradiography. For western blotting, skin biopsies were homogenized into the lysis buffer (20 mM Tris, pH 7.6, 1 mM EDTA, 50 mM NaCl, 50 mM NaF, 1% Triton-X100) supplemented with 1 mM PMSF, 1 mU/ml approtinin, 1 mM Na$_3$VO$_4$ and 10 µg/ml leupeptin. The Ig-fusion proteins were precipitated from 1 mg of total protein and separated in SDS-PAGE, transferred to nitrocellulose and detected using the horseradish peroxidase conjugated rabbit antibodies against human IgG (DAKO, Carpinteria, Calif.) and the enhanced chemiluminescence detection system.

E. Immunohistochemistry and TUNEL Staining

Paraffin sections (5 µm) from 4% paraformaldehyde (PFA) fixed tissues were stained using rat monoclonal antibodies against mouse VEGFR-3 (Kubo et al., *Blood* 96:546-553, 2000) or CD31/PECAM-1 (PharMingen, San Diego, Calif.), rabbit polyclonal antibodies against mouse LYVE-1 (Banerji et al., *J Cell Biol,* 144: 789-801, 1999), or biotinylated mouse monoclonal antibodies against human IgG Fc domain (Zymed, San Diego, Calif.). For TUNEL staining, detection of DNA fragmentation was done using in situ Cell Death Detection Kit (fluorescein; Roche, Indianapolis, Ind.).

F. Visualization of Blood and Lymphatic Vessels

For visualization of blood vessels (Thurston et al. *Science* 286, 2511-2514 (1999), 100 µl of 1 mg/ml biotinylated *Lycopersicon esculentum* lectin (Sigma) was injected (IV) by the femoral vein and allowed to circulate for 2 min. After fixation by perfusion with 1% PFA/0.5% glutaraldehyde in PBS, bound lectin was visualized by the ABC-3,3'-diaminobenzidine peroxidase reaction. In VEGFR-3+/LacZ mice the lymphatic vessels were then stained by the β-galactosidase substrate X-Gal (Sigma, St. Louis, Mo.). For the visualization of functional lymphatic vessels, Evans blue dye (5 mg/ml; Sigma, St. Louis, Mo.) was injected into the footpad of the hindlimb or TRITC-dextran (Sigma, 8 mg/ml) was injected into the ear or tail and the lymphatic vessels were analysed by light or fluorescence microscopy, respectively.

G. Detection of the VEGFR-3-Ig Protein in Serum

ELISA plates (Nunc Maxisorp, Copenhagen, Denmark) were coated with mouse antibodies against human IgG (Zymed, 2 µg/ml in PBS) or human VEGFR-3 (clone 7B8, 4 µg/ml). The mouse sera were diluted into the incubation buffer (5 mg/ml BSA, 0.05% Tween 20 in PBS) and allowed to bind for 2 h at room temperature. The plates were then washed 3 times with incubation buffer before addition of mouse anti-human IgG1 (Zymed, 1:500) for 1 h. Streptavidin conjugated with alkaline phosphatase (Zymed, 1:5000) was then incubated in the wells for 30 min, followed by addition of the substrate (1 mg/ml p-Nitrophenyl phosphate in 0.1 M diethanolamine, pH 10.3) and absorbance reading at 405 nm.

H. Magnetic Resonance Imaging

MRI data was acquired using a s.m.i.s. console (Surrey Medical Imaging Systems, Guildford, UK) interfaced to a 9.4 T vertical magnet (Oxford Instruments, Oxford, UK). A single loop surface coil (diameter 35 mm) was used for signal transmission and detection. A T$_2$-weighted (TR 2000 ms, TE 40 ms, 4 scans/line) multislice spin-echo sequence was used with an FOV of 25.6 mm$^2$ (matrix size: 256×128) and slice thickness of 1.3 mm in transverse orientation. Saturation pulses centered at 1.2 ppm were used to decrease fat signals in T$_2$-images. Diffusion weighted MRI was acquired using monopolar diffusion gradients (b-value=800 s/mm$^2$) along slice axis in the spin-echo sequence (TR 2000 ms, TE 40 ms), and water apparent diffusion coefficient (ADC) was computed by fitting the MRI data as function of b-values into a single exponential.

Results

A. Soluble VEGFR-3 Inhibits VEGF-C-Mediated Signaling In Vitro

To inhibit VEGF-C signaling through VEGFR-3, a fusion protein consisting of the first three Ig-homology domains of VEGFR-3 and IgG Fc domain was employed. The VEGFR-3-Ig bound VEGF-C and VEGF-D with the same efficiency as the full-length extracellular domain and inhibited VEGF-C-induced VEGFR-3 phosphorylation and subsequent p42/p44 mitogen-activated protein kinase (MAPK) activation in VEGFR-3 expressing endothelial cells. In contrast, a similar VEGFR-1-Ig fusion protein, which does not bind VEGF-C, did not affect p42/p44 MAPK activation.

The effect of soluble VEGFR-3 on VEGF-C signaling also was determined in a bioassay using a chimeric VEGFR-3/erythropoietin (Epo) receptor capable of transmitting VEGF-C dependent survival and proliferation signals for the IL-3 dependent Ba/F3 cells in the absence of IL-3 (Achen et al., Eur. J. Biochem., 267:2505-2515, 2000). In this cellular assay, there was a complete inhibition of VEGF-C-dependent cell survival at a 0.5:1 molar ratio (VEGFR-3-Ig:VEGF-C), whereas VEGFR-1-Ig had no effect. Similarly, VEGFR-3-Ig also abolished VEGF-D-induced survival of the VEGFR-3/EpoR cells. In contrast, even a ten-fold molar excess of VEGFR-2-Ig only partially abolished VEGF-C dependent viability, perhaps because of lower affinity of VEGF-C to VEGFR-2.

B. Soluble VEGFR-3 Inhibits the Formation of Lymphatic Vessels In Vivo

To determine the inhibitory effect of VEGFR-3-Ig in vivo, the fusion protein was expressed under the control of K14 promoter, which directs transgene expression to the basal epidermal cells of the skin. VEGFR-3-Ig expression was detected in mice by northern blotting of skin RNA and by western blotting of protein extracts from the skin. These mice appeared healthy and fertile and had a normal lifespan. Histological examination of the skin revealed a thickened dermis and subcutaneous layer. Antibody staining confirmed VEGFR-3-Ig expression in the basal keratinocytes. When the skin sections were stained for markers of the lymphatic endothelium, VEGFR-3 (Jussila et al., *Cancer Res.* 58:1599-1604, 1998; Kubo et al. *Blood,* 96 546-553, 2000) and LYVE-1 (Banerji et al. *J Cell Biol,* 144: 789-801, 1999), no lymphatic vessels were observed in the transgenic mice, even though lymphatic vessels were stained in the skin of control mice. In contrast, blood vessels were stained for the panendothelial marker PECAM-1/CD31 in both transgenic and wild-type skin.

C. Soluble VEGFR-3 Suppresses Lymphangiogenesis but not Angiogenesis

In order to visualize better the lymphatic vessels, the K14-VEGFR-3-Ig mice were mated with heterozygous VEGFR-3+/LacZ mice that express β-gal in the Flt4 locus (Dumont et al. *Science* 282, 946-949, 1998). When whole-mount tissue preparations of the ear skin were stained using the substrate X-gal, no lymphatic vessels were detected, whereas, in the control mice, blue-staining lymphatic vessels were visualized. In vascular perfusion staining using biotin-labeled lectin (Thurston et al. *Science* 286, 2511-2514, 1999), the blood vessels appeared normal in the K14-VEGFR-3-Ig mice.

The absence of the lymphatic vessels also was confirmed using a functional assay, monitoring the fate of Evans blue dye or TRITC-dextran injected into the skin. The dye was rapidly collected into the lymphatic vessels surrounding the ischiatic vein after injection into the hindlimb footpads of wild-type mice, whereas no dye was seen in such vessels in the transgenic mice where collecting lymphatic vessels were either absent or rudimentary. The lymphatic vessels in control mice also were visualized using fluorescence microscopy for TRITC-dextran injected intradermally into the ear or tail, whereas no such vessels were seen in the transgenic mice.

D. Circulating Soluble VEGFR-3 is Associated with a Transient Loss of Lymphatic Tissue in Internal Organs By the age of two weeks, the VEGFR-3-Ig/VEGFR-3+/LacZ mice had only a few thin and rudimentary, if any, lymphatic vessels in organs such as diaphragm, heart, lungs, caecum, pancreas, mesenterium and esophagus when compared with the control VEGFR-3+/LacZ littermate mice. Such findings, obtained by X-Gal staining, were confirmed by immunostaining for VEGFR-3 and LYVE-1. In addition, the lack of lymphatic vessels in heart pericardium was associated with pericardial fluid accumulation in at least some of the mice. At three weeks of age, regrowth of the lymphatic vessels was apparent. In adult transgenic mice, only some organs such as heart and diaphragm had abnormally patterned and incompletely developed lymphatic vessels.

The effects seen in the internal organs indicate that the soluble VEGFR-3-Ig protein circulates in the bloodstream. Indeed the fusion protein was detected in the serum of the transgenic mice using a specific enzyme-linked immunosorbent assay; the levels ranged between 100-200 ng/ml, being highest in the young mice. Based on our in vitro experiments, such concentrations would neutralize about 20-40 ng/ml of VEGF-C. The VEGFR-3-Ig protein was relatively stable in the bloodstream, as intravenously injected recombinant VEGFR-3-Ig was in the serum for at least nine hours.

E. The Transgenic Phenotype has Features of Human Lymphedema

The K14-VEGFR-3-Ig mice were distinguished from their wild-type littermates by the swelling of their feet, which was already visible at birth. Older mice showed thickening of the skin, dermal fibrosis and increased deposition of subcutaneous fat. Magnetic resonance imaging (MRI) revealed prominent $T_2$-hyperintense regions in foot skin and subcutaneous tissues of the transgenic mice indicating increased fluid accumulation, whereas similar regions were absent in littermate controls. The apparent diffusion coefficient (ADC) for these hyperintense areas was $1.99 [0.60] \times 10^{-3}$ mm$^2$/s, being higher than for normal tissue where ADC was $1.32 [0.21] \times 10^{-3}$ mm$^2$/s, and about 1-2 orders of magnitude greater than the values for fat (Thurston, et al. *Science* 286, 2511-2514 (1999). In addition, size and appearance of lymph nodes varied, especially in the large para-aortic lymph nodes surrounding the inferior vena cava. However, mesenteric lymph nodes and Peyer patches were seen in the VEGFR-3-Ig mice.

F. Regression of the Developing Lymphatic Vessels by Endothelial Cell Apoptosis

During embryogenesis, a dramatic increase in K14-driven transgene expression occurs at E14.5, and by E16.5 the expression encompasses the whole embryonic skin (Byrne, et al., *Development* 120, 2369-2383, 1994). When analyzed in the VEGFR-3+/LacZ background by X-Gal staining, the lymphatic networks of the skin were indistinguishable between transgenic and wild-type embryos at E15. At E15.5-16.5, the lymphatic vessels of the transgenic embryos had regressed in some areas. At E17.5, the lymphatic vessels still formed a continuous network but were thinner than in control embryos. At E18.5, the whole cutaneous lymphatic network was disrupted in the transgenic embryos and after birth, none or only a few single disrupted lymphatic vessels were in the skin, mainly accompanying the large dermal blood vessels. Thus, the lymphatic vessels initially form in the skin during embryogenesis, but regress when the expression of the transgene is turned on. However, the formation of the dermal blood vasculature was not inhibited in the K14-VEGFR-3-Ig embryos as shown by X-Gal staining in the Tie-promoter-LacZ background (Korhonen et al. *Blood* 86, 1828-1835 (1995).

TUNEL staining was used to detect apoptosis in endothelial cells, which were identified by simultaneous staining for PECAM-1. Apoptotic endothelial cells were seen in the dermis of the transgenic embryos first at E17.5 and E18.5. No endothelial cell apoptosis was seen in wild-type embryos. The TUNEL-positive cells were detected almost exclusively in VEGFR-3 positive endothelia in the transgenic skin, indicating that VEGFR-3-Ig mediated apoptosis was targeted to the lymphatic endothelium.

The present Example shows that soluble VEGFR-3 fusion protein inhibits lymphangiogenesis and leads to regression of existing fetal lymphatic vessels in vivo. Continuous VEGFR-3 signaling is thus essential for the fetal development and maintenance of the lymphatic vascular system.

The absence of lymphatic vessels in the skin of K14-VEGFR-3-Ig mice was associated with a thickening of the dermis and especially the subcutaneous fat layer as in human lymphedema—a disorder caused by insufficiency of the lymphatic system and characterized by swelling of the extremities of increasing severity (Witte et al., Lymphangiogenesis: Mechanisms, significance and clinical implications in *Regulation of Angiogenesis* (eds. Goldberg, I. D. & Rosen, E. M.) 65-112 (Birkhäuser Verlag, Basel, Switzerland) 1997; Mortimer, Cancer 83, 2798-2802 (1998). In primary lymphedema, which is an inherited disease, the superficial or subcutaneous lymphatic vessels are usually hypoplastic or aplastic, and they fail to transport the lymphatic fluid into the venous circulation. Noninherited secondary or acquired lymphedema develops when the lymphatic vessels are damaged by surgery, radiation, infection or trauma. In lymphedema, a protein-rich fluid accumulates in interstitial space, leading to tissue fibrosis and adipose degeneration, interference with wound healing, and susceptibility to infections. In K14-VEGFR-3-Ig mice, there was a lack of macromolecular transport in the dermis and, especially in older mice, signs of dermal fibrosis. Moreover, the swelling of the feet and increased fluid accumulation in the skin and subcutaneous tissue in the transgenic mice were similar to symptoms of human lymphedema. The skin phenotype of the K14-VEGFR-3-Ig mice thus shares several features with human lymphedema. In studies of some lymphedema families, heterozygous inactivating missense mutations have been detected in the tyrosine kinase encoding region of Flt4 (Karkkainen et al., *Nature Genet.*, 25:153-159, 2000; Irrthum et al., Am. J. Hum. Gen. 67:259-301 2001). At least some lymphedema patients have dysfunctional lymphatics due to defective VEGFR-3 signaling. In concurrence with this observation, the results in this Example show that the disruption of VEGFR-3 signaling by the soluble VEGFR-3 protein can completely destroy the lymphatic network and lead to a lymphedema-like phenotype. Moreover, as in some cases of lymphedema, the size and appearance of certain regional lymph nodes was variable, indicating that lymph flow and a functional lymphatic vasculature are essential for the formation of normal lymph nodes.

VEGFR-3-Ig also induced regression of the already-formed lymphatics. Thus, inhibition of VEGF-C and/or VEGF-D binding to VEGFR-3 during development leads to apoptosis of the lymphatic endothelial cells and to the disruption of the lymphatic network, which indicates that continuous VEGFR-3 signaling is required for the survival of the lymphatic endothelial cells. In cell culture, VEGFR-3 activates biochemical signaling cascades associated with endothelial cell survival. Although transgenic mice that overexpress either VEGF-C (Jeltsch et al., Science, 276:1423-1425, 1997) or VEGF-D in the skin develop a hyperplastic dermal lymphatic vasculature, their dermal lymphatic vessels also regress when mated with K14-VEGFR-3-Ig mice. As both VEGFR-3 ligands are also expressed in the skin, the phenotype observed in K14-VEGFR-3-Ig mice might be due to a simultaneous inhibition of both VEGF-C and VEGF-D.

Although VEGF-C and VEGF-D are mitogenic for blood vascular endothelial cells both in vitro and in vivo (Joukov et al. EMBO J 16, 3898-3911, 1997; Achen et al., Proc. Natl. Acad. Sci. USA 95, 548-553, 1998; Cao et al., Proc. Natl. Acad. Sci. USA 95, 14389-14392 1998; Witzenbichler et al., Am. J. Pathol. 153, 381-394, 1998; Marconcini et al., Proc. Natl. Acad. Sci. USA 96, 9671-9676, 1999), VEGFR-3-Ig did not seem to affect the blood vessels. The late onset of K14-promoter expression may explain the lymphatic specificity of the VEGFR-3-Ig protein. A substantial increase in K14-promoter activity is not seen until around E14.5-16.5 (Byrne et al., Development 120:2369-2383, 1994). Although the expression of endogenous VEGFR-3 is first detected at E8.5 in developing blood vessels, by E14.5-16.5 it has been largely down-regulated in healthy blood vascular endothelia (Dumont et al., Science 282, 946-949 1998; Kaipainen, et al., Proc. Natl. Acad. Sci. USA 92, 3566-3570, 1995). Therefore, during the developmental period when VEGFR-3 no longer occurs normally in the blood vessel endothelium of healthy tissues, VEGFR-3 signaling plays a more minimal role in angiogenesis in the skin than do other receptors.

In young VEGFR-3-Ig mice, several internal organs were almost completely devoid of lymphatic vessels, but they regrow in adult mice, although into an abnormal pattern in some organs. The growth and maintenance of lymphatic vasculature can therefore be reactivated in adult organs. Decreasing levels of VEGFR-3 inhibition or independent signals from, for example, maturing connective tissue matrix might have reactivated lymphangiogenesis, but there was no evidence obtained that would suggest that increased VEGF-C or VEGF-D levels were responsible. However, administration of VEGF-C through an adenovirus vector in quantities exceeding those usually found in interstitial fluids can lead to lymphatic growth in adult tissues. The use in gene therapy of a modified VEGF-C that no longer binds VEGFR-2 (U.S. Pat. No. 6,130,071 Joukev et al., J. Biol. Chem., 273:6599-6602) might prevent its potential effects on the blood vascular endothelium.

Thus, soluble VEGFR-3 is a potent and specific inhibitor of lymphangiogenesis in vivo. The soluble VEGFR-3 may comprise the extracellular fragment of Flt4 as described elsewhere in the specification. As seen above a preferred soluble VEGFR-3 is one which comprises the first three domains of VEGFR-3, however it should be understood that the soluble VEGFR-3 may be a fragment of VEGFR-3 which comprises more or less of the wild-type sequence of VEGFR-3 that is depicted in FIG. 2. For example, the soluble peptide also may comprise one or more of IgIV, IgV, IgVI, IgVII. Alternatively, it may be that a soluble VEGFR-3 may comprise only IgI in any combination with one or more of the domains selected from the group consisting of IgII, IgIII, IgIV, IgV, IgVI and IgVII.

In addition, the present Example also establishes a mouse model that has features of human lymphedema. As lymphedema always involves the skin, this mouse model is useful in understanding and characterizing this disease and in testing of new therapies that could be applied to human patients.

All documents including patents and journal articles that are cited in the summary or detailed description of the invention are hereby incorporated by reference, in their entirety.

While the invention here has been described in connection with specific embodiments thereof, it will be understood that it is capable of further modifications and this application is intended to cover any variations, uses, or adaptions of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A polynucleotide comprising a nucleotide sequence that encodes a fusion protein comprising:
   (a) a polypeptide comprising a portion of a human Vascular Endothelial Growth Factor Receptor-3 (VEGFR-3) extracellular domain (EC); wherein said portion and said polypeptide bind to VEGFR-3 ligands VEGF-C and VEGF-D and comprise at least the first, second, and third immunoglobulin-like domains of the VEGFR-3-EC, wherein the polypeptide lacks VEGFR-3-EC immunoglobulin-like domains IV-VII; and (b) an immunoglobulin-like domain of human VEGFR-2 or an immunoglobulin Fc peptide, wherein (a) is fused to (b), and wherein the fusion protein binds VEGF-C and VEGF-D, is soluble, and lacks any transmembrane domain.

2. The polynucleotide of claim 1, wherein the portion of the VEGFR-3-EC consists of the first, second, and third immunoglobulin-like domains of the VEGFR-3-EC.

3. The polynucleotide according to claim 1, wherein the portion of the VEGFR-3-EC consists of the first through third immunoglobulin-like domains of SEQ ID NO: 2.

4. The polynucleotide of claim 1, wherein the polypeptide comprises amino acids 47-314 of SEQ ID NO: 2.

5. The polynucleotide of claim 1, wherein the polypeptide in the fusion protein is fused to an immunoglobulin-like domain of human VEGFR-2.

6. The polynucleotide of claim 1, wherein the polypeptide in the fusion protein is fused to an immunoglobulin Fc peptide.

7. The polynucleotide according to claim 1, further comprising an expression control sequence operatively linked to the sequence that encodes the fusion protein.

8. An expression vector comprising an expression control sequence operatively linked to the polynucleotide according to claim 1.

9. The expression vector according to claim 8, wherein the expression control sequence comprises a promoter that promotes expression in a mammalian cell.

10. The expression vector according to claim 9 that is a viral vector selected from the group consisting of retrovirus, adenovirus, adeno-associated virus, vaccinia virus, and herpesvirus vectors.

11. A host cell transformed or transfected with a vector according to claim 9.

12. The polynucleotide according to claim 1, wherein the encoded fusion protein is capable of inhibiting at least one of: VEGF-C-mediated stimulation of endothelial cells that express VEGFR-3; and VEGF-C-induced phosphorylation of VEGFR-3.

13. The polynucleotide according to claim 1, wherein the encoded fusion protein is capable of inhibiting VEGF-C-induced and VEGF-D-induced signaling of VEGFR-3.

14. A polynucleotide comprising a nucleotide sequence that encodes a fusion protein comprising a polypeptide consisting essentially of: (i) a fragment of human Vascular Endothelial Growth Factor Receptor-3 (VEGFR-3) consisting essentially of the first through third immunoglobulin-like domains of human VEGFR-3 extracellular domain (EC), and (ii) an immunoglobulin Fc peptide, wherein (i) is fused to (ii), and wherein the polypeptide binds both VEGF-C and VEGF-D.

15. The polynucleotide according to claim 14, wherein the fragment comprises amino acids 47-314 of SEQ ID NO: 2.

16. The polynucleotide according to claim 14, further comprising an expression control sequence operatively linked to the sequence that encodes the fusion protein.

17. An expression vector comprising an expression control sequence operatively linked to the polynucleotide according to claim 14.

18. The expression vector according to claim 17, wherein the expression control sequence comprises a promoter that promotes expression in a mammalian cell.

19. The expression vector according to claim 18 that is a viral vector selected from the group consisting of retrovirus, adenovirus, adeno-associated virus, vaccinia virus, and herpesvirus vectors.

20. A host cell transformed or transfected with a vector according to claim 18.

21. The polynucleotide according to claim 14, wherein the encoded fusion protein is capable of inhibiting at least one of: VEGF-C-mediated stimulation of endothelial cells that express VEGFR-3; and VEGF-C-induced phosphorylation of VEGFR-3.

22. The polynucleotide according to claim 14, wherein the encoded fusion protein is capable of inhibiting VEGF-C-induced and VEGF-D-induced signaling of VEGFR-3.

23. A polynucleotide comprising a nucleotide sequence that encodes a chimeric polypeptide comprising a fragment of a human Vascular Endothelial Growth Factor Receptor-3 (VEGFR-3) extracellular domain (EC) fused to a heterologous polypeptide;

wherein said fragment binds to VEGF-C and VEGF-D and comprises at least the first through third immunoglobulin-like domains of the VEGFR-3-EC, wherein the polypeptide lacks VEGFR-3-EC immunoglobulin-like domains IV-VII; and wherein the polypeptide is a soluble polypeptide lacking any transmembrane domain.

24. The polynucleotide according to claim 23, wherein the heterologous polypeptide increases serum solubility or serum half-life of the fragment of human VEGFR-3-EC.

25. The polynucleotide according to claim 23, wherein the fragment comprises amino acids 47-314 of SEQ ID NO: 2.

26. The polynucleotide of claim 23, wherein the heterologous polypeptide is an immunoglobulin Fc peptide.

27. The polynucleotide according to claim 23, further comprising an expression control sequence operatively linked to the sequence that encodes the chimeric polypeptide.

28. An expression vector comprising an expression control sequence operatively linked to the polynucleotide according to claim 23.

29. The expression vector according to claim 28, wherein the expression control sequence comprises a promoter that promotes expression in a mammalian cell.

30. The expression vector according to claim 29 that is a viral vector selected from the group consisting of retrovirus, adenovirus, adeno-associated virus, vaccinia virus, and herpesvirus vectors.

31. A host cell transformed or transfected with a vector according to claim 29.

32. The polynucleotide according to claim 23, wherein the encoded chimeric polypeptide is capable of inhibiting at least one of: VEGF-C-mediated stimulation of endothelial cells that express VEGFR-3; and VEGF-C-induced phosphorylation of VEGFR-3.

33. The polynucleotide according to claim 23, wherein the encoded chimeric polypeptide is capable of inhibiting VEGF-C-induced and VEGF-D-induced signaling of VEGFR-3.

* * * * *

SEQUENCE LISTING

```
<160> NUMBER OF SEQ ID NOS: 24

<210> SEQ ID NO 1
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 1
ccacgcgcag cggccggag atg cag cgg ggc gcc gcg ctg tgc ctg cga ctg      52
                    Met Gln Arg Gly Ala Ala Leu Cys Leu Arg Leu
                    1               5                   10 tgg ctc tgc ctg gga ctc ctg gac ggc ctg gtg agt ggc tac tcc atg      100
Trp Leu Cys Leu Gly Leu Leu Asp Gly Leu Val Ser Gly Tyr Ser Met
            15                  20                  25 acc ccc ccg acc ttg aac atc acg gag gag tca cac gtc atc gac acc      148
Thr Pro Pro Thr Leu Asn Ile Thr Glu Glu Ser His Val Ile Asp Thr
        30                  35                  40 ggt gac agc ctg tcc atc tcc tgc agg gga cag cac ccc ctc gag tgg      196
```

```
Gly Asp Ser Leu Ser Ile Ser Cys Arg Gly Gln His Pro Leu Glu Trp
 45                  50                  55 gct tgg cca gga gct cag gag gcg cca gcc acc gga gac aag gac agc    244
Ala Trp Pro Gly Ala Gln Glu Ala Pro Ala Thr Gly Asp Lys Asp Ser
 60                  65                  70                  75 gag gac acg ggg gtg gtg cga gac tgc gag ggc aca gac gcc agg ccc    292
Glu Asp Thr Gly Val Val Arg Asp Cys Glu Gly Thr Asp Ala Arg Pro
                 80                  85                  90 tac tgc aag gtg ttg ctg ctg cac gag gta cat gcc aac gac aca ggc    340
Tyr Cys Lys Val Leu Leu Leu His Glu Val His Ala Asn Asp Thr Gly
             95                 100                 105 agc tac gtc tgc tac tac aag tac atc aag gca cgc atc gag ggc acc    388
Ser Tyr Val Cys Tyr Tyr Lys Tyr Ile Lys Ala Arg Ile Glu Gly Thr
         110                 115                 120 acg gcc gcc agc tcc tac gtg ttc gtg aga gac ttt gag cag cca ttc    436
Thr Ala Ala Ser Ser Tyr Val Phe Val Arg Asp Phe Glu Gln Pro Phe
     125                 130                 135 atc aac aag cct gac acg ctc ttg gtc aac agg aag gac gcc atg tgg    484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg    532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac    580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac    628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc    676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg    724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac    772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac    820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc    868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac    916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc    964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc   1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca   1060
Phe Ile Ser Val Glu Trp Leu Lys Gly Pro Ile Leu Glu Ala Thr Ala
            335                 340                 345 gga gac gag ctg gtg aag ctg ccc gtg aag ctg gca gcg tac ccc ccg   1108
Gly Asp Glu Leu Val Lys Leu Pro Val Lys Leu Ala Ala Tyr Pro Pro
        350                 355                 360
```

```
ccc gag ttc cag tgg tac aag gat gga aag gca ctg tcc ggg cgc cac      1156
Pro Glu Phe Gln Trp Tyr Lys Asp Gly Lys Ala Leu Ser Gly Arg His
365                 370                 375 agt cca cat gcc ctg gtg ctc aag gag gtg aca gag gcc agc aca ggc      1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac      1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag      1300
Ile Ser Leu Glu Leu Val Val Asn Val Pro Pro Gln Ile His Glu Lys
            415                 420                 425 gag gcc tcc tcc ccc agc atc tac tcg cgt cac agc cgc cag gcc ctc      1348
Glu Ala Ser Ser Pro Ser Ile Tyr Ser Arg His Ser Arg Gln Ala Leu
        430                 435                 440 acc tgc acg gcc tac ggg gtg ccc ctg cct ctc agc atc cag tgg cac      1396
Thr Cys Thr Ala Tyr Gly Val Pro Leu Pro Leu Ser Ile Gln Trp His
    445                 450                 455 tgg cgg ccc tgg aca ccc tgc aag atg ttt gcc cag cgt agt ctc cgg      1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg      1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg      1540
Val Thr Thr Gln Asp Ala Val Asn Pro Ile Glu Ser Leu Asp Thr Trp
                495                 500                 505 acc gag ttt gtg gag gga aag aat aag act gtg agc aag ctg gtg atc      1588
Thr Glu Phe Val Glu Gly Lys Asn Lys Thr Val Ser Lys Leu Val Ile
            510                 515                 520 cag aat gcc aac gtg tct gcc atg tac aag tgt gtg gtc tcc aac aag      1636
Gln Asn Ala Asn Val Ser Ala Met Tyr Lys Cys Val Val Ser Asn Lys
        525                 530                 535 gtg ggc cag gat gag cgg ctc atc tac ttc tat gtg acc acc atc ccc      1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc      1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat      1780
Gln Pro Val Leu Leu Ser Cys Gln Ala Asp Ser Tyr Lys Tyr Glu His
                575                 580                 585 ctg cgc tgg tac cgc ctc aac ctg tcc acg ctg cac gat gcg cac ggg      1828
Leu Arg Trp Tyr Arg Leu Asn Leu Ser Thr Leu His Asp Ala His Gly
            590                 595                 600 aac ccg ctt ctc ctc gac tgc aag aac gtg cat ctg ttc gcc acc cct      1876
Asn Pro Leu Leu Leu Asp Cys Lys Asn Val His Leu Phe Ala Thr Pro
        605                 610                 615 ctg gcc gcc agc ctg gag gag gtg gca cct ggg gcg cgc cac gcc acg      1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat      1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag      2020
Val Cys Glu Val Gln Asp Arg Arg Ser His Asp Lys His Cys His Lys
                655                 660                 665 aag tac ctg tcg gtg cag gcc ctg gaa gcc cct cgg ctc acg cag aac      2068
Lys Tyr Leu Ser Val Gln Ala Leu Glu Ala Pro Arg Leu Thr Gln Asn
            670                 675                 680
```

```
ttg acc gac ctc ctg gtg aac gtg agc gac tcg ctg gag atg cag tgc    2116
Leu Thr Asp Leu Leu Val Asn Val Ser Asp Ser Leu Glu Met Gln Cys
    685                 690                 695 ttg gtg gcc gga gcg cac gcg ccc agc atc gtg tgg tac aaa gac gag    2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag    2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg    2260
Lys Leu Ser Ile Gln Arg Val Arg Glu Glu Asp Ala Gly Arg Tyr Leu
            735                 740                 745 tgc agc gtg tgc aac gcc aag ggc tgc gtc aac tcc tcc gcc agc gtg    2308
Cys Ser Val Cys Asn Ala Lys Gly Cys Val Asn Ser Ser Ala Ser Val
        750                 755                 760 gcc gtg gaa ggc tcc gag gat aag ggc agc atg gag atc gtg atc ctt    2356
Ala Val Glu Gly Ser Glu Asp Lys Gly Ser Met Glu Ile Val Ile Leu
    765                 770                 775 gtc ggt acc ggc gtc atc gct gtc ttc ttc tgg gtc ctc ctc ctc ctc    2404
Val Gly Thr Gly Val Ile Ala Val Phe Phe Trp Val Leu Leu Leu Leu
780                 785                 790                 795 atc ttc tgt aac atg agg agg ccg gcc cac gca gac atc aag acg ggc    2452
Ile Phe Cys Asn Met Arg Arg Pro Ala His Ala Asp Ile Lys Thr Gly
                800                 805                 810 tac ctg tcc atc atc atg gac ccc ggg gag gtg cct ctg gag gag caa    2500
Tyr Leu Ser Ile Ile Met Asp Pro Gly Glu Val Pro Leu Glu Glu Gln
            815                 820                 825 tgc gaa tac ctg tcc tac gat gcc agc cag tgg gaa ttc ccc cga gag    2548
Cys Glu Tyr Leu Ser Tyr Asp Ala Ser Gln Trp Glu Phe Pro Arg Glu
        830                 835                 840 cgg ctg cac ctg ggg aga gtg ctc ggc tac ggc gcc ttc ggg aag gtg    2596
Arg Leu His Leu Gly Arg Val Leu Gly Tyr Gly Ala Phe Gly Lys Val
    845                 850                 855 gtg gaa gcc tcc gct ttc ggc atc cac aag ggc agc agc tgt gac acc    2644
Val Glu Ala Ser Ala Phe Gly Ile His Lys Gly Ser Ser Cys Asp Thr
860                 865                 870                 875 gtg gcc gtg aaa atg ctg aaa gag ggc gcc acg gcc agc gag cac cgc    2692
Val Ala Val Lys Met Leu Lys Glu Gly Ala Thr Ala Ser Glu His Arg
                880                 885                 890 gcg ctg atg tcg gag ctc aag atc ctc att cac atc ggc aac cac ctc    2740
Ala Leu Met Ser Glu Leu Lys Ile Leu Ile His Ile Gly Asn His Leu
            895                 900                 905 aac gtg gtc aac ctc ctc ggg gcg tgc acc aag ccg cag ggc ccc ctc    2788
Asn Val Val Asn Leu Leu Gly Ala Cys Thr Lys Pro Gln Gly Pro Leu
        910                 915                 920 atg gtg atc gtg gag ttc tgc aag tac ggc aac ctc tcc aac ttc ctg    2836
Met Val Ile Val Glu Phe Cys Lys Tyr Gly Asn Leu Ser Asn Phe Leu
    925                 930                 935 cgc gcc aag cgg gac gcc ttc agc ccc tgc gcg gag aag tct ccc gag    2884
Arg Ala Lys Arg Asp Ala Phe Ser Pro Cys Ala Glu Lys Ser Pro Glu
940                 945                 950                 955 cag cgc gga cgc ttc cgc gcc atg gtg gag ctc gcc agg ctg gat cgg    2932
Gln Arg Gly Arg Phe Arg Ala Met Val Glu Leu Ala Arg Leu Asp Arg
                960                 965                 970 agg cgg ccg ggg agc agc gac agg gtc ctc ttc gcg cgg ttc tcg aag    2980
Arg Arg Pro Gly Ser Ser Asp Arg Val Leu Phe Ala Arg Phe Ser Lys
            975                 980                 985 acc gag ggc gga gcg agg cgg gct tct cca gac caa gaa  gct gag gac    3028
Thr Glu Gly Gly Ala Arg Arg Ala Ser Pro Asp Gln Glu  Ala Glu Asp
```

-continued

```
           990                 995                 1000
ctg tgg ctg agc ccg ctg acc atg gaa gat ctt gtc tgc tac agc      3073
Leu Trp Leu Ser Pro Leu Thr Met Glu Asp Leu Val Cys Tyr Ser
    1005                1010                1015 ttc cag gtg gcc aga ggg atg gag ttc ctg gct tcc cga aag tgc      3118
Phe Gln Val Ala Arg Gly Met Glu Phe Leu Ala Ser Arg Lys Cys
    1020                1025                1030 atc cac aga gac ctg gct gct cgg aac att ctg ctg tcg gaa agc      3163
Ile His Arg Asp Leu Ala Ala Arg Asn Ile Leu Leu Ser Glu Ser
    1035                1040                1045 gac gtg gtg aag atc tgt gac ttt ggc ctt gcc cgg gac atc tac      3208
Asp Val Val Lys Ile Cys Asp Phe Gly Leu Ala Arg Asp Ile Tyr
    1050                1055                1060 aaa gac cct gac tac gtc cgc aag ggc agt gcc cgg ctg ccc ctg      3253
Lys Asp Pro Asp Tyr Val Arg Lys Gly Ser Ala Arg Leu Pro Leu
    1065                1070                1075 aag tgg atg gcc cct gaa agc atc ttc gac aag gtg tac acc acg      3298
Lys Trp Met Ala Pro Glu Ser Ile Phe Asp Lys Val Tyr Thr Thr
    1080                1085                1090 cag agt gac gtg tgg tcc ttt ggg gtg ctt ctc tgg gag atc ttc      3343
Gln Ser Asp Val Trp Ser Phe Gly Val Leu Leu Trp Glu Ile Phe
    1095                1100                1105 tct ctg ggg gcc tcc ccg tac cct ggg gtg cag atc aat gag gag      3388
Ser Leu Gly Ala Ser Pro Tyr Pro Gly Val Gln Ile Asn Glu Glu
    1110                1115                1120 ttc tgc cag cgg ctg aga gac ggc aca agg atg agg gcc ccg gag      3433
Phe Cys Gln Arg Leu Arg Asp Gly Thr Arg Met Arg Ala Pro Glu
    1125                1130                1135 ctg gcc act ccc gcc ata cgc cgc atc atg ctg aac tgc tgg tcc      3478
Leu Ala Thr Pro Ala Ile Arg Arg Ile Met Leu Asn Cys Trp Ser
    1140                1145                1150 gga gac ccc aag gcg aga cct gca ttc tcg gag ctg gtg gag atc      3523
Gly Asp Pro Lys Ala Arg Pro Ala Phe Ser Glu Leu Val Glu Ile
    1155                1160                1165 ctg ggg gac ctg ctc cag ggc agg ggc ctg caa gag gaa gag gag      3568
Leu Gly Asp Leu Leu Gln Gly Arg Gly Leu Gln Glu Glu Glu Glu
    1170                1175                1180 gtc tgc atg gcc ccg cgc agc tct cag agc tca gaa gag ggc agc      3613
Val Cys Met Ala Pro Arg Ser Ser Gln Ser Ser Glu Glu Gly Ser
    1185                1190                1195 ttc tcg cag gtg tcc acc atg gcc cta cac atc gcc cag gct gac      3658
Phe Ser Gln Val Ser Thr Met Ala Leu His Ile Ala Gln Ala Asp
    1200                1205                1210 gct gag gac agc ccg cca agc ctg cag cgc cac agc ctg gcc gcc      3703
Ala Glu Asp Ser Pro Pro Ser Leu Gln Arg His Ser Leu Ala Ala
    1215                1220                1225 agg tat tac aac tgg gtg tcc ttt ccc ggg tgc ctg gcc aga ggg      3748
Arg Tyr Tyr Asn Trp Val Ser Phe Pro Gly Cys Leu Ala Arg Gly
    1230                1235                1240 gct gag acc cgt ggt tcc tcc agg atg aag aca ttt gag gaa ttc      3793
Ala Glu Thr Arg Gly Ser Ser Arg Met Lys Thr Phe Glu Glu Phe
    1245                1250                1255 ccc atg acc cca acc acc tac aaa ggc tct gtg gac aac cag aca      3838
Pro Met Thr Pro Thr Thr Tyr Lys Gly Ser Val Asp Asn Gln Thr
    1260                1265                1270 gac agt ggg atg gtg ctg gcc tcg gag gag ttt gag cag ata gag      3883
Asp Ser Gly Met Val Leu Ala Ser Glu Glu Phe Glu Gln Ile Glu
    1275                1280                1285 agc agg cat aga caa gaa agc ggc ttc agg tagctgaagc agagagagag    3933
```

-continued

```
Ser Arg His Arg Gln Glu Ser  Gly Phe Arg
   1290                1295
```

```
aaggcagcat acgtcagcat tttcttctct gcacttataa gaaagatcaa agactttaag    3993
actttcgcta tttcttctac tgctatctac tacaaacttc aaagaggaac caggaggaca    4053
agaggagcat gaaagtggac aaggagtgtg accactgaag caccacaggg aagggggttag   4113 gcctccggat gactgcgggc aggcctggat aatatccagc ctcccacaag aagctggtgg    4173
agcagagtgt tccctgactc ct                                             4195
```

```
<210> SEQ ID NO 2
<211> LENGTH: 1298
<212> TYPE: PRT
<213> ORGANISM: Homo sapiens

<400> SEQUENCE: 2
```

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
```

```
        305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
                340                 345                 350
Lys Leu Pro Val Lys Leu Ala Ala Tyr Pro Pro Glu Phe Gln Trp
                355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
                420                 425                 430
Ser Ile Tyr Ser Arg His Ser Arg Gln Ala Leu Thr Cys Thr Ala Tyr
                435                 440                 445
Gly Val Pro Leu Pro Leu Ser Ile Gln Trp His Trp Arg Pro Trp Thr
    450                 455                 460
Pro Cys Lys Met Phe Ala Gln Arg Ser Leu Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
                500                 505                 510
Gly Lys Asn Lys Thr Val Ser Lys Leu Val Ile Gln Asn Ala Asn Val
                515                 520                 525
Ser Ala Met Tyr Lys Cys Val Val Ser Asn Lys Val Gly Gln Asp Glu
                530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
                580                 585                 590
Leu Asn Leu Ser Thr Leu His Asp Ala His Gly Asn Pro Leu Leu Leu
                595                 600                 605
Asp Cys Lys Asn Val His Leu Phe Ala Thr Pro Leu Ala Ala Ser Leu
                610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
                660                 665                 670
Gln Ala Leu Glu Ala Pro Arg Leu Thr Gln Asn Leu Thr Asp Leu Leu
                675                 680                 685
Val Asn Val Ser Asp Ser Leu Glu Met Gln Cys Leu Val Ala Gly Ala
                690                 695                 700
His Ala Pro Ser Ile Val Trp Tyr Lys Asp Glu Arg Leu Leu Glu Glu
705                 710                 715                 720
Lys Ser Gly Val Asp Leu Ala Asp Ser Asn Gln Lys Leu Ser Ile Gln
                725                 730                 735
```

-continued

```
Arg Val Arg Glu Glu Asp Ala Gly Arg Tyr Leu Cys Ser Val Cys Asn
            740                 745                 750

Ala Lys Gly Cys Val Asn Ser Ala Ser Val Ala Val Glu Gly Ser
        755                 760                 765

Glu Asp Lys Gly Ser Met Glu Ile Val Ile Leu Val Gly Thr Gly Val
        770                 775                 780

Ile Ala Val Phe Phe Trp Val Leu Leu Leu Ile Phe Cys Asn Met
785             790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
            850                 855                 860

Phe Gly Ile His Lys Gly Ser Ser Cys Asp Thr Val Ala Val Lys Met
865             870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
            930                 935                 940

Ala Phe Ser Pro Cys Ala Glu Lys Ser Pro Glu Gln Arg Gly Arg Phe
945             950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140
```

```
Ile Arg Arg Ile Met Leu Asn Cys Trp Ser Gly Asp Pro Lys Ala
1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Arg
    1295

<210> SEQ ID NO 3
<211> LENGTH: 4795
<212> TYPE: DNA
<213> ORGANISM: Homo sapiens
<220> FEATURE:
<221> NAME/KEY: CDS
<222> LOCATION: (20)..(4108)

<400> SEQUENCE: 3
ccacgcgcag cggccggag atg cag cgg ggc gcc gcg ctg tgc ctg cga ctg      52
                    Met Gln Arg Gly Ala Ala Leu Cys Leu Arg Leu
                     1               5                  10 tgg ctc tgc ctg gga ctc ctg gac ggc ctg gtg agt ggc tac tcc atg     100
Trp Leu Cys Leu Gly Leu Leu Asp Gly Leu Val Ser Gly Tyr Ser Met
         15                  20                  25 acc ccc ccg acc ttg aac atc acg gag gag tca cac gtc atc gac acc     148
Thr Pro Pro Thr Leu Asn Ile Thr Glu Glu Ser His Val Ile Asp Thr
     30                  35                  40 ggt gac agc ctg tcc atc tcc tgc agg gga cag cac ccc ctc gag tgg     196
Gly Asp Ser Leu Ser Ile Ser Cys Arg Gly Gln His Pro Leu Glu Trp
 45                  50                  55 gct tgg cca gga gct cag gag gcg cca gcc acc gga gac aag gac agc     244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc     292
Glu Asp Thr Gly Val Val Arg Asp Cys Glu Gly Thr Asp Ala Arg Pro
                 80                  85                  90 tac tgc aag gtg ttg ctg ctg cac gag gta cat gcc aac gac aca ggc     340
Tyr Cys Lys Val Leu Leu Leu His Glu Val His Ala Asn Asp Thr Gly
             95                 100                 105 agc tac gtc tgc tac tac aag tac atc aag gca cgc atc gag ggc acc     388
Ser Tyr Val Cys Tyr Tyr Lys Tyr Ile Lys Ala Arg Ile Glu Gly Thr
         110                 115                 120 acg gcc gcc agc tcc tac gtg ttc gtg aga gac ttt gag cag cca ttc     436
Thr Ala Ala Ser Ser Tyr Val Phe Val Arg Asp Phe Glu Gln Pro Phe
     125                 130                 135
```

```
atc aac aag cct gac acg ctc ttg gtc aac agg aag gac gcc atg tgg      484
Ile Asn Lys Pro Asp Thr Leu Leu Val Asn Arg Lys Asp Ala Met Trp
140             145                 150                 155 gtg ccc tgt ctg gtg tcc atc ccc ggc ctc aat gtc acg ctg cgc tcg      532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac      580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac      628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc      676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg      724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac      772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac      820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc      868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac      916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc      964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc     1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca     1060
Phe Ile Ser Val Glu Trp Leu Lys Gly Pro Ile Leu Glu Ala Thr Ala
            335                 340                 345 gga gac gag ctg gtg aag ctg ccc gtg aag ctg gcg gcg tac ccc ccg     1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac     1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc     1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac     1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag     1300
Ile Ser Leu Glu Leu Val Val Asn Val Pro Pro Gln Ile His Glu Lys
            415                 420                 425 gag gcc tcc tcc ccc agc atc tac tcg cgt cac agc cgc cag gcc ctc     1348
Glu Ala Ser Ser Pro Ser Ile Tyr Ser Arg His Ser Arg Gln Ala Leu
        430                 435                 440 acc tgc acg gcc tac ggg gtg ccc ctg cct ctc agc atc cag tgg cac     1396
Thr Cys Thr Ala Tyr Gly Val Pro Leu Pro Leu Ser Ile Gln Trp His
```

```
                445                 450                 455
tgg cgg ccc tgg aca ccc tgc aag atg ttt gcc cag cgt agt ctc cgg    1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg    1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg    1540
Val Thr Thr Gln Asp Ala Val Asn Pro Ile Glu Ser Leu Asp Thr Trp
        495                 500                 505 acc gag ttt gtg gag gga aag aat aag act gtg agc aag ctg gtg atc    1588
Thr Glu Phe Val Glu Gly Lys Asn Lys Thr Val Ser Lys Leu Val Ile
            510                 515                 520 cag aat gcc aac gtg tct gcc atg tac aag tgt gtg gtc tcc aac aag    1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc    1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc    1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat    1780
Gln Pro Val Leu Leu Ser Cys Gln Ala Asp Ser Tyr Lys Tyr Glu His
        575                 580                 585 ctg cgc tgg tac cgc ctc aac ctg tcc acg ctg cac gat gcg cac ggg    1828
Leu Arg Trp Tyr Arg Leu Asn Leu Ser Thr Leu His Asp Ala His Gly
            590                 595                 600 aac ccg ctt ctg ctc gac tgc aag aac gtg cat ctg ttc gcc acc cct    1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg    1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat    1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag    2020
Val Cys Glu Val Gln Asp Arg Arg Ser His Asp Lys His Cys His Lys
        655                 660                 665 aag tac ctg tcg gtg cag gcc ctg gaa gcc cct cgg ctc acg cag aac    2068
Lys Tyr Leu Ser Val Gln Ala Leu Glu Ala Pro Arg Leu Thr Gln Asn
            670                 675                 680 ttg acc gac ctc ctg gtg aac gtg agc gac tcg ctg gag atg cag tgc    2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag    2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag    2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg    2260
Lys Leu Ser Ile Gln Arg Val Arg Glu Glu Asp Ala Gly Arg Tyr Leu
        735                 740                 745 tgc agc gtg tgc aac gcc aag ggc tgc gtc aac tcc tcc gcc agc gtg    2308
Cys Ser Val Cys Asn Ala Lys Gly Cys Val Asn Ser Ser Ala Ser Val
            750                 755                 760 gcc gtg gaa ggc tcc gag gat aag ggc agc atg gag atc gtg atc ctt    2356
```

```
Ala Val Glu Gly Ser Glu Asp Lys Gly Ser Met Glu Ile Val Ile Leu
        765                 770                 775 gtc ggt acc ggc gtc atc gct gtc ttc ttc tgg gtc ctc ctc ctc ctc        2404
Val Gly Thr Gly Val Ile Ala Val Phe Phe Trp Val Leu Leu Leu Leu
780                 785                 790                 795 atc ttc tgt aac atg agg agg ccg gcc cac gca gac atc aag acg ggc        2452
Ile Phe Cys Asn Met Arg Arg Pro Ala His Ala Asp Ile Lys Thr Gly
                    800                 805                 810 tac ctg tcc atc atc atg gac ccc ggg gag gtg cct ctg gag gag caa        2500
Tyr Leu Ser Ile Ile Met Asp Pro Gly Glu Val Pro Leu Glu Glu Gln
                815                 820                 825 tgc gaa tac ctg tcc tac gat gcc agc cag tgg gaa ttc ccc cga gag        2548
Cys Glu Tyr Leu Ser Tyr Asp Ala Ser Gln Trp Glu Phe Pro Arg Glu
            830                 835                 840 cgg ctg cac ctg ggg aga gtg ctc ggc tac ggc gcc ttc ggg aag gtg        2596
Arg Leu His Leu Gly Arg Val Leu Gly Tyr Gly Ala Phe Gly Lys Val
    845                 850                 855 gtg gaa gcc tcc gct ttc ggc atc cac aag ggc agc agc tgt gac acc        2644
Val Glu Ala Ser Ala Phe Gly Ile His Lys Gly Ser Ser Cys Asp Thr
860                 865                 870                 875 gtg gcc gtg aaa atg ctg aaa gag ggc gcc acg gcc agc gag cac cgc        2692
Val Ala Val Lys Met Leu Lys Glu Gly Ala Thr Ala Ser Glu His Arg
                    880                 885                 890 gcg ctg atg tcg gag ctc aag atc ctc att cac atc ggc aac cac ctc        2740
Ala Leu Met Ser Glu Leu Lys Ile Leu Ile His Ile Gly Asn His Leu
                895                 900                 905 aac gtg gtc aac ctc ctc ggg gcg tgc acc aag ccg cag ggc ccc ctc        2788
Asn Val Val Asn Leu Leu Gly Ala Cys Thr Lys Pro Gln Gly Pro Leu
            910                 915                 920 atg gtg atc gtg gag ttc tgc aag tac ggc aac ctc tcc aac ttc ctg        2836
Met Val Ile Val Glu Phe Cys Lys Tyr Gly Asn Leu Ser Asn Phe Leu
925                 930                 935 cgc gcc aag cgg gac gcc ttc agc ccc tgc gcg gag aag tct ccc gag        2884
Arg Ala Lys Arg Asp Ala Phe Ser Pro Cys Ala Glu Lys Ser Pro Glu
940                 945                 950                 955 cag cgc gga cgc ttc cgc gcc atg gtg gag ctc gcc agg ctg gat cgg        2932
Gln Arg Gly Arg Phe Arg Ala Met Val Glu Leu Ala Arg Leu Asp Arg
                960                 965                 970 agg cgg ccg ggg agc agc gac agg gtc ctc ttc gcg cgg ttc tcg aag        2980
Arg Arg Pro Gly Ser Ser Asp Arg Val Leu Phe Ala Arg Phe Ser Lys
                975                 980                 985 acc gag ggc gga gcg agg cgg gct tct cca gac caa gaa gct gag gac        3028
Thr Glu Gly Gly Ala Arg Arg Ala Ser Pro Asp Gln Glu Ala Glu Asp
                990                 995                 1000 ctg tgg ctg agc ccg ctg acc atg gaa gat ctt gtc tgc tac agc        3073
Leu Trp Leu Ser Pro Leu Thr Met Glu Asp Leu Val Cys Tyr Ser
    1005                1010                1015 ttc cag gtg gcc aga ggg atg gag ttc ctg gct tcc cga aag tgc        3118
Phe Gln Val Ala Arg Gly Met Glu Phe Leu Ala Ser Arg Lys Cys
    1020                1025                1030 atc cac aga gac ctg gct gct cgg aac att ctg ctg tcg gaa agc        3163
Ile His Arg Asp Leu Ala Ala Arg Asn Ile Leu Leu Ser Glu Ser
    1035                1040                1045 gac gtg gtg aag atc tgt gac ttt ggc ctt gcc cgg gac atc tac        3208
Asp Val Val Lys Ile Cys Asp Phe Gly Leu Ala Arg Asp Ile Tyr
    1050                1055                1060 aaa gac cct gac tac gtc cgc aag ggc agt gcc cgg ctg ccc ctg        3253
Lys Asp Pro Asp Tyr Val Arg Lys Gly Ser Ala Arg Leu Pro Leu
    1065                1070                1075
```

| | | | | | | | | | | | |
|---|---|---|---|---|---|---|---|---|---|---|---|
| aag | tgg | atg | gcc | cct | gaa | agc | atc | ttc | gac | aag | gtg | tac | acc | acg | 3298 |
| Lys | Trp | Met | Ala | Pro | Glu | Ser | Ile | Phe | Asp | Lys | Val | Tyr | Thr | Thr | |
| 1080 | | | | 1085 | | | | | 1090 | | | | | | | cag agt gac gtg tgg tcc ttt ggg gtg ctt ctc tgg gag atc ttc    3343
Gln Ser Asp Val Trp Ser Phe Gly Val Leu Leu Trp Glu Ile Phe
1095             1100                 1105 tct ctg ggg gcc tcc ccg tac cct ggg gtg cag atc aat gag gag    3388
Ser Leu Gly Ala Ser Pro Tyr Pro Gly Val Gln Ile Asn Glu Glu
1110             1115                 1120 ttc tgc cag cgg ctg aga gac ggc aca agg atg agg gcc ccg gag    3433
Phe Cys Gln Arg Leu Arg Asp Gly Thr Arg Met Arg Ala Pro Glu
1125             1130                 1135 ctg gcc act ccc gcc ata cgc cgc atc atg ctg aac tgc tgg tcc    3478
Leu Ala Thr Pro Ala Ile Arg Arg Ile Met Leu Asn Cys Trp Ser
1140             1145                 1150 gga gac ccc aag gcg aga cct gca ttc tcg gag ctg gtg gag atc    3523
Gly Asp Pro Lys Ala Arg Pro Ala Phe Ser Glu Leu Val Glu Ile
1155             1160                 1165 ctg ggg gac ctg ctc cag ggc agg ggc ctg caa gag gaa gag gag    3568
Leu Gly Asp Leu Leu Gln Gly Arg Gly Leu Gln Glu Glu Glu Glu
1170             1175                 1180 gtc tgc atg gcc ccg cgc agc tct cag agc tca gaa gag ggc agc    3613
Val Cys Met Ala Pro Arg Ser Ser Gln Ser Ser Glu Glu Gly Ser
1185             1190                 1195 ttc tcg cag gtg tcc acc atg gcc cta cac atc gcc cag gct gac    3658
Phe Ser Gln Val Ser Thr Met Ala Leu His Ile Ala Gln Ala Asp
1200             1205                 1210 gct gag gac agc ccg cca agc ctg cag cgc cac agc ctg gcc gcc    3703
Ala Glu Asp Ser Pro Pro Ser Leu Gln Arg His Ser Leu Ala Ala
1215             1220                 1225 agg tat tac aac tgg gtg tcc ttt ccc ggg tgc ctg gcc aga ggg    3748
Arg Tyr Tyr Asn Trp Val Ser Phe Pro Gly Cys Leu Ala Arg Gly
1230             1235                 1240 gct gag acc cgt ggt tcc tcc agg atg aag aca ttt gag gaa ttc    3793
Ala Glu Thr Arg Gly Ser Ser Arg Met Lys Thr Phe Glu Glu Phe
1245             1250                 1255 ccc atg acc cca acg acc tac aaa ggc tct gtg gac aac cag aca    3838
Pro Met Thr Pro Thr Thr Tyr Lys Gly Ser Val Asp Asn Gln Thr
1260             1265                 1270 gac agt ggg atg gtg ctg gcc tcg gag gag ttt gag cag ata gag    3883
Asp Ser Gly Met Val Leu Ala Ser Glu Glu Phe Glu Gln Ile Glu
1275             1280                 1285 agc agg cat aga caa gaa agc ggc ttc agc tgt aaa gga cct ggc    3928
Ser Arg His Arg Gln Glu Ser Gly Phe Ser Cys Lys Gly Pro Gly
1290             1295                 1300 cag aat gtg gct gtg acc agg gca cac cct gac tcc caa ggg agg    3973
Gln Asn Val Ala Val Thr Arg Ala His Pro Asp Ser Gln Gly Arg
1305             1310                 1315 cgg cgg cgg cct gag cgg ggg gcc cga gga ggc cag gtg ttt tac    4018
Arg Arg Arg Pro Glu Arg Gly Ala Arg Gly Gly Gln Val Phe Tyr
1320             1325                 1330 aac agc gag tat ggg gag ctg tcg gag cca agc gag gag gac cac    4063
Asn Ser Glu Tyr Gly Glu Leu Ser Glu Pro Ser Glu Glu Asp His
1335             1340                 1345 tgc tcc ccg tct gcc cgc gtg act ttc ttc aca gac aac agc tac    4108
Cys Ser Pro Ser Ala Arg Val Thr Phe Phe Thr Asp Asn Ser Tyr
1350             1355                 1360 taagcagcat cggacaagac ccccagcact tgggggttca ggcccggcag ggcgggcaga    4168
gggctggagg cccaggctgg gaactcatct ggttgaactc tggtggcaca ggagtgtcct    4228

-continued

```
cttccctctc tgcagacttc ccagctagga agagcaggac tccaggccca aggctcccgg    4288
aattccgtca ccacgactgg ccagggcacg ctccagctgc cccggcccct ccccctgaga    4348
ttcagatgtc atttagttca gcatccgcag gtgctggtcc cggggccagc acttccatgg    4408
gaatgtctct ttggcgacct cctttcatca cactgggtgg tggcctggtc cctgtttttcc   4468 cacgaggaat ctgtgggtct gggagtcaca cagtgttgga ggttaaggca tacgagagca    4528
gaggtctccc aaacgccctt tcctcctcag gcacacagct actctcccca cgagggctgg    4588
ctggcctcac ccaccctgc acagttgaag ggaggggctg tgtttccatc tcaaagaagg     4648
catttgcagg gtcctcttct gggcctgacc aaacagccaa ctagcccctg ggtggccac     4708 cagtatgaca gtattatacg ctggcaacac agaggcagcc cgcacacctg cgcctgggtg    4768
ttgagagcca tcctgcaagt ctttttc                                         4795
```

<210> SEQ ID NO 4
<211> LENGTH: 1363
<212> TYPE: PRT
<213> ORGANISM: Homo sapiens

<400> SEQUENCE: 4

```
Met Gln Arg Gly Ala Ala Leu Cys Leu Arg Leu Trp Leu Cys Leu Gly
  1               5                  10                  15

Leu Leu Asp Gly Leu Val Ser Gly Tyr Ser Met Thr Pro Pro Thr Leu
             20                  25                  30

Asn Ile Thr Glu Glu Ser His Val Ile Asp Thr Gly Asp Ser Leu Ser
         35                  40                  45

Ile Ser Cys Arg Gly Gln His Pro Leu Glu Trp Ala Trp Pro Gly Ala
     50                  55                  60

Gln Glu Ala Pro Ala Thr Gly Asp Lys Asp Ser Glu Asp Thr Gly Val
 65                  70                  75                  80

Val Arg Asp Cys Glu Gly Thr Asp Ala Arg Pro Tyr Cys Lys Val Leu
                 85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270
```

```
Ala Glu Arg Gly Lys Trp Val Pro Glu Arg Ser Gln Gln Thr His
        275                 280                 285

Thr Glu Leu Ser Ser Ile Leu Thr Ile His Asn Val Ser Gln His Asp
        290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
                340                 345                 350

Lys Leu Pro Val Lys Leu Ala Ala Tyr Pro Pro Glu Phe Gln Trp
        355                 360                 365

Tyr Lys Asp Gly Lys Ala Leu Ser Gly Arg His Ser Pro His Ala Leu
        370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
                420                 425                 430

Ser Ile Tyr Ser Arg His Ser Arg Gln Ala Leu Thr Cys Thr Ala Tyr
                435                 440                 445

Gly Val Pro Leu Pro Leu Ser Ile Gln Trp His Trp Arg Pro Trp Thr
        450                 455                 460

Pro Cys Lys Met Phe Ala Gln Arg Ser Leu Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
                500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
        530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
                580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
        610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
        675                 680                 685
```

```
Val Asn Val Ser Asp Ser Leu Glu Met Gln Cys Leu Val Ala Gly Ala
    690             695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
        980                 985                 990

Arg Arg Ala Ser Pro Asp Gln Glu Ala Glu Asp Leu Trp Leu Ser Pro
    995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
```

```
                  1100             1105             1110
Pro Tyr Pro Gly Val Gln Ile Asn Glu Glu Phe Cys Gln Arg Leu
    1115             1120             1125

Arg Asp Gly Thr Arg Met Arg Ala Pro Glu Leu Ala Thr Pro Ala
    1130             1135             1140

Ile Arg Arg Ile Met Leu Asn Cys Trp Ser Gly Asp Pro Lys Ala
    1145             1150             1155

Arg Pro Ala Phe Ser Glu Leu Val Glu Ile Leu Gly Asp Leu Leu
    1160             1165             1170

Gln Gly Arg Gly Leu Gln Glu Glu Glu Val Cys Met Ala Pro
    1175             1180             1185

Arg Ser Ser Gln Ser Ser Glu Glu Gly Ser Phe Ser Gln Val Ser
    1190             1195             1200

Thr Met Ala Leu His Ile Ala Gln Ala Asp Ala Glu Asp Ser Pro
    1205             1210             1215

Pro Ser Leu Gln Arg His Ser Leu Ala Ala Arg Tyr Tyr Asn Trp
    1220             1225             1230

Val Ser Phe Pro Gly Cys Leu Ala Arg Gly Ala Glu Thr Arg Gly
    1235             1240             1245

Ser Ser Arg Met Lys Thr Phe Glu Glu Phe Pro Met Thr Pro Thr
    1250             1255             1260

Thr Tyr Lys Gly Ser Val Asp Asn Gln Thr Asp Ser Gly Met Val
    1265             1270             1275

Leu Ala Ser Glu Glu Phe Glu Gln Ile Glu Ser Arg His Arg Gln
    1280             1285             1290

Glu Ser Gly Phe Ser Cys Lys Gly Pro Gly Gln Asn Val Ala Val
    1295             1300             1305

Thr Arg Ala His Pro Asp Ser Gln Gly Arg Arg Arg Pro Glu
    1310             1315             1320

Arg Gly Ala Arg Gly Gly Gln Val Phe Tyr Asn Ser Glu Tyr Gly
    1325             1330             1335

Glu Leu Ser Glu Pro Ser Glu Asp His Cys Ser Pro Ser Ala
    1340             1345             1350

Arg Val Thr Phe Phe Thr Asp Asn Ser Tyr
    1355             1360

<210> SEQ ID NO 5
<211> LENGTH: 1311
<212> TYPE: PRT
<213> ORGANISM: Homo sapiens
<220> FEATURE:
<221> NAME/KEY: MISC_FEATURE
<223> OTHER INFORMATION: FLT1

<400> SEQUENCE: 5

Met Val Ser Tyr Trp Asp Thr Gly Val Leu Leu Cys Ala Leu Leu
1               5                   10                  15

Cys Leu Leu Leu Thr Gly Ser Ser Gly Ser Lys Leu Lys Asp Pro
                20                  25                  30

Glu Leu Ser Leu Lys Gly Thr Gln His Ile Met Gln Ala Gly Gln Thr
                35                  40                  45

Leu His Leu Gln Cys Arg Gly Glu Ala Ala His Lys Trp Ser Leu Pro
        50                  55                  60

Glu Asn Asn Asn Asn Asn Met Val Ser Lys Glu Ser Glu Arg Leu
65                  70                  75                  80
```

```
Ser Ile Thr Lys Ser Ala Cys Gly Arg Asn Gly Lys Gln Phe Cys Ser
                85                  90                  95
Thr Leu Thr Leu Asn Thr Ala Gln Ala Asn His Thr Gly Phe Tyr Ser
            100                 105                 110
Cys Lys Tyr Leu Ala Val Pro Thr Ser Lys Lys Lys Glu Thr Glu Ser
            115                 120                 125
Ala Ile Tyr Ile Phe Ile Ser Asp Thr Gly Arg Pro Phe Val Glu Met
            130                 135                 140
Tyr Ser Glu Ile Pro Glu Ile Ile His Met Thr Glu Gly Arg Glu Leu
145                 150                 155                 160
Val Ile Pro Cys Arg Val Thr Ser Pro Asn Ile Thr Val Thr Leu Lys
                165                 170                 175
Lys Phe Pro Leu Asp Thr Leu Ile Pro Asp Gly Lys Arg Ile Ile Trp
            180                 185                 190
Asp Ser Arg Lys Gly Phe Ile Ile Ser Asn Ala Thr Tyr Lys Glu Ile
            195                 200                 205
Gly Leu Leu Thr Cys Glu Ala Thr Val Asn Gly His Leu Tyr Lys Thr
            210                 215                 220
Asn Asn Tyr Leu Thr His Arg Gln Thr Asn Thr Ile Ile Asp Val Gln
225                 230                 235                 240
Ile Ser Thr Pro Arg Pro Val Lys Leu Leu Arg Gly His Thr Leu Val
                245                 250                 255
Leu Asn Cys Thr Ala Thr Thr Pro Leu Asn Thr Arg Val Gln Met Thr
                260                 265                 270
Trp Ser Tyr Pro Asp Asn Asn Asn Glu Lys Asn Lys Arg Ala Ser Val
            275                 280                 285
Arg Arg Arg Ile Asp Gln Ser Asn Ser His Ala Asn Ile Phe Tyr Ser
            290                 295                 300
Val Leu Thr Ile Asp Lys Met Gln Asn Lys Asp Lys Gly Leu Tyr Thr
305                 310                 315                 320
Cys Arg Val Arg Ser Gly Pro Ser Phe Lys Ser Val Asn Thr Ser Val
                325                 330                 335
His Ile Tyr Asp Lys Ala Phe Ile Thr Val Lys His Arg Lys Gln Gln
            340                 345                 350
Val Leu Glu Thr Val Ala Gly Lys Arg Ser Tyr Arg Leu Ser Met Lys
            355                 360                 365
Val Lys Ala Phe Pro Ser Pro Glu Val Val Trp Leu Lys Asp Gly Leu
            370                 375                 380
Pro Ala Thr Glu Lys Ser Ala Arg Tyr Leu Thr Arg Gly Tyr Ser Leu
385                 390                 395                 400
Ile Ile Lys Asp Val Thr Glu Glu Asp Ala Gly Asn Tyr Thr Ile Leu
                405                 410                 415
Leu Ser Ile Lys Gln Ser Asn Val Phe Lys Asn Leu Thr Ala Thr Leu
            420                 425                 430
Ile Val Asn Val Lys Pro Gln Ile Tyr Glu Lys Ala Val Ser Ser Phe
            435                 440                 445
Pro Asp Pro Ala Leu Tyr Pro Leu Gly Ser Arg Gln Ile Leu Thr Cys
450                 455                 460
Thr Ala Tyr Gly Ile Pro Gln Pro Asn Thr Ile Lys Trp Phe Trp His
465                 470                 475                 480
Pro Cys Asn His Asn His Ser Glu Ala Arg Cys Asp Phe Cys Ser Asn
                485                 490                 495
Asn Glu Glu Ser Phe Ile Leu Asp Asn Asn Asn Asn Asn Asn Asn Ala
```

-continued

```
                500                 505                 510
Asp Ser Asn Met Gly Asn Arg Ile Glu Ser Ile Thr Gln Arg Met Ala
        515                 520                 525
Ile Ile Glu Gly Lys Asn Lys Met Ala Ser Thr Leu Val Val Ala Asp
        530                 535                 540
Ser Arg Ile Ser Gly Ile Tyr Ile Cys Ile Ala Ser Asn Lys Val Gly
545                 550                 555                 560
Thr Val Gly Arg Asn Ile Ser Phe Tyr Ile Thr Asp Val Pro Asn Gly
                565                 570                 575
Phe His Val Asn Leu Glu Lys Met Pro Thr Asn Asn Glu Gly Glu Asp
                580                 585                 590
Leu Lys Leu Ser Cys Thr Val Asn Lys Phe Leu Tyr Arg Asp Val Thr
        595                 600                 605
Trp Ile Leu Leu Asn Asn Asn Asn Asn Asn Asn Asn Asn Asn Asn Asn
        610                 615                 620
Asn Asn Asn Asn Asn Arg Thr Val Asn Arg Thr Met His Tyr Ser
625                 630                 635                 640
Ile Ser Lys Gln Lys Met Ala Ile Thr Lys Glu His Ser Ile Thr Leu
                645                 650                 655
Asn Leu Thr Ile Met Asn Val Ser Leu Gln Asp Ser Gly Thr Tyr Ala
                660                 665                 670
Cys Arg Ala Arg Asn Val Tyr Thr Gly Glu Glu Ile Leu Gln Lys Lys
        675                 680                 685
Glu Ile Thr Ile Arg Asp Gln Glu Ala Pro Tyr Leu Leu Arg Asn Leu
        690                 695                 700
Ser Asp His Thr Val Ala Ile Ser Ser Ser Thr Thr Leu Asp Cys His
705                 710                 715                 720
Ala Asn Gly Val Pro Glu Pro Gln Ile Thr Trp Phe Lys Asn Asn His
                725                 730                 735
Lys Ile Gln Gln Glu Pro Gly Ile Ile Leu Gly Pro Gly Ser Ser Thr
                740                 745                 750
Leu Phe Ile Glu Arg Val Thr Glu Glu Asp Glu Gly Val Tyr His Cys
        755                 760                 765
Lys Ala Thr Asn Gln Lys Gly Ser Val Glu Ser Ser Ala Tyr Leu Thr
        770                 775                 780
Val Gln Gly Thr Ser Asp Lys Ser Asn Leu Glu Leu Ile Thr Leu Thr
785                 790                 795                 800
Cys Thr Cys Val Ala Ala Thr Leu Phe Trp Leu Leu Leu Thr Leu Leu
                805                 810                 815
Ile Arg Lys Met Lys Arg Ser Ser Asn Ser Glu Ile Lys Thr Asp Tyr
                820                 825                 830
Leu Ser Ile Ile Met Asp Pro Asp Glu Val Pro Leu Asp Glu Gln Cys
        835                 840                 845
Glu Arg Leu Pro Tyr Asp Ala Ser Lys Trp Glu Phe Ala Arg Glu Arg
        850                 855                 860
Leu Lys Leu Gly Lys Ser Leu Gly Arg Gly Ala Phe Gly Lys Val Val
865                 870                 875                 880
Gln Ala Ser Ala Phe Gly Ile Lys Lys Ser Pro Thr Cys Arg Thr Val
                885                 890                 895
Ala Val Lys Met Leu Lys Glu Gly Ala Thr Ala Ser Glu Tyr Lys Ala
                900                 905                 910
Leu Met Thr Glu Leu Lys Ile Leu Thr His Ile Gly His His Leu Asn
        915                 920                 925
```

```
Val Val Asn Leu Leu Gly Ala Cys Thr Lys Gln Gly Pro Leu Met
    930             935             940

Val Ile Val Glu Tyr Cys Lys Tyr Gly Asn Leu Ser Asn Tyr Leu Lys
945             950             955             960

Ser Lys Arg Asp Leu Phe Phe Leu Asn Lys Asp Ala Ala Leu His Met
            965             970             975

Glu Pro Lys Lys Glu Lys Met Glu Pro Gly Leu Glu Gln Gly Lys Lys
                980             985             990

Pro Arg Leu Asp Ser Val Thr Ser  Ser Glu Ser Phe Ala  Ser Ser Gly
            995            1000             1005

Phe Gln  Glu Asp Lys Ser Leu  Ser Asp Val Glu Glu  Glu Glu Asp
    1010             1015             1020

Ser Asp  Gly Phe Tyr Lys Glu  Pro Ile Thr Met Glu  Asp Leu Ile
    1025             1030             1035

Ser Tyr  Ser Phe Gln Val Ala  Arg Gly Met Glu Phe  Leu Ser Ser
    1040             1045             1050

Arg Lys  Cys Ile His Arg Asp  Leu Ala Ala Arg Asn  Ile Leu Leu
    1055             1060             1065

Ser Glu  Asn Asn Val Val Lys  Ile Cys Asp Phe Gly  Leu Ala Arg
    1070             1075             1080

Asp Ile  Tyr Lys Asn Pro Asp  Tyr Val Arg Lys Gly  Asp Thr Arg
    1085             1090             1095

Leu Pro  Leu Lys Trp Met Ala  Pro Glu Ser Ile Phe  Asp Lys Ile
    1100             1105             1110

Tyr Ser  Thr Lys Ser Asp Val  Trp Ser Tyr Gly Val  Leu Leu Trp
    1115             1120             1125

Glu Ile  Phe Ser Leu Gly Gly  Ser Pro Tyr Pro Gly  Val Gln Met
    1130             1135             1140

Asp Glu  Asp Phe Cys Ser Arg  Leu Arg Glu Gly Met  Arg Met Arg
    1145             1150             1155

Ala Pro  Glu Tyr Ser Thr Pro  Glu Ile Tyr Gln Ile  Met Leu Asp
    1160             1165             1170

Cys Trp  His Arg Asp Pro Lys  Glu Arg Pro Arg Phe  Ala Glu Leu
    1175             1180             1185

Val Glu  Lys Leu Gly Asp Leu  Leu Gln Ala Asn Val  Gln Gln Asp
    1190             1195             1200

Gly Lys  Asp Tyr Ile Pro Ile  Asn Ala Ile Leu Thr  Gly Asn Ser
    1205             1210             1215

Gly Phe  Thr Tyr Ser Thr Pro  Ala Phe Ser Glu Asp  Phe Phe Lys
    1220             1225             1230

Glu Ser  Ile Ser Ala Pro Lys  Phe Asn Ser Gly Ser  Ser Asp Asp
    1235             1240             1245

Val Arg  Tyr Val Asn Ala Phe  Lys Phe Met Ser Leu  Glu Arg Ile
    1250             1255             1260

Lys Thr  Phe Glu Glu Leu Leu  Pro Asn Ala Thr Ser  Met Phe Asp
    1265             1270             1275

Asp Tyr  Gln Gly Asp Ser Ser  Thr Leu Leu Ala Ser  Pro Met Leu
    1280             1285             1290

Lys Arg  Phe Thr Trp Thr Asp  Ser Lys Pro Lys Ala  Ser Leu Lys
    1295             1300             1305

Ile Glu  Val
    1310
```

```
<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Xaa in positions 1 and 2 are selected
      independently from the group consisting of aspartic acid and
      glutamic acid.
<220> FEATURE:
<221> NAME/KEY: MOD_RES
<222> LOCATION: (4)..(4)
<223> OTHER INFORMATION: Xaa in position 4 is selected independently
      from the group consisting of methionine and valine.
<220> FEATURE:
<221> NAME/KEY: MOD_RES
<222> LOCATION: (5)..(5)
<223> OTHER INFORMATION: Xaa in position 5 is selected independently
      from the group consisting of proline, aspartic acid, and glutamic
      acid.

<400> SEQUENCE: 6

Xaa Xaa Tyr Xaa Met
1               5

<210> SEQ ID NO 7
<211> LENGTH: 70
<212> TYPE: DNA
<213> ORGANISM: Artificial Sequence
<220> FEATURE:
<223> OTHER INFORMATION: Oligonucleotide probe

<400> SEQUENCE: 7
acatgcatgc caccatgcag cggggcgccg cgctgtgcct gcgactgtgg ctctgcctgg    60
gactcctgga                                                          70

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 8
acatgcatgc cccgccggtc atcc                                          24

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
cggaattccc catgacccca ac                                            22

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide probe

<400> SEQUENCE: 10
ccatcgatgg atcctacctg aagccgcttt ctt                                33
```

<210> SEQ ID NO 11
<211> LENGTH: 34
<212> TYPE: DNA
<213> ORGANISM: Artificial Sequence
<220> FEATURE:
<223> OTHER INFORMATION: Oligonucleotide probe

<400> SEQUENCE: 11
cccaagcttg gatccaagtg gctactccat gacc                        34

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
gttgcctgtg atgtgcacca                                        20

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 13
ctggagtcga cttggcggac t                                      21

<210> SEQ ID NO 14
<211> LENGTH: 60
<212> TYPE: DNA
<213> ORGANISM: Artificial Sequence
<220> FEATURE:
<223> OTHER INFORMATION: Oligonucleotide

<400> SEQUENCE: 14
cgcggatccc tagtgatggt gatggtgatg tctaccttcg atcatgctgc ccttatcctc    60

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 15
ctggagtcga cttggcggac t                                      21

<210> SEQ ID NO 16
<211> LENGTH: 28
<212> TYPE: DNA
<213> ORGANISM: Artificial Sequence
<220> FEATURE:
<223> OTHER INFORMATION: Oligonucleotide probe

<400> SEQUENCE: 16
cgggatccct ccatgctgcc cttatcct                               28

<210> SEQ ID NO 17
<211> LENGTH: 36
<212> TYPE: DNA
<213> ORGANISM: Artificial Sequence
<220> FEATURE:

```
<223> OTHER INFORMATION: Oligonucleotide probe

<400> SEQUENCE: 17
ggcaagcttg aattcgccac catgcagcgg ggcgcc                              36

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 18
gttgcctgtg atgtgcacca                                                20

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 19
ctggagtcga cttggcggac t                                              21

<210> SEQ ID NO 20
<211> LENGTH: 44
<212> TYPE: DNA
<213> ORGANISM: Artificial Sequence
<220> FEATURE:
<223> OTHER INFORMATION: Oligonucleotide probe

<400> SEQUENCE: 20
cgcggatcca agcttactta ccttccatgc tgcccttatc ctcg                     44

<210> SEQ ID NO 21
<211> LENGTH: 419
<212> TYPE: PRT
<213> ORGANISM: Homo sapiens

<400> SEQUENCE: 21
```

Met His Leu Leu Gly Phe Phe Ser Val Ala Cys Ser Leu Leu Ala
1               5                   10                  15

Ala Leu Leu Pro Gly Pro Arg Glu Ala Pro Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

-continued

```
Arg Cys Gly Gly Cys Cys Asn Ser Glu Gly Leu Gln Cys Met Asn Thr
            165                 170                 175
Ser Thr Ser Tyr Leu Ser Lys Thr Leu Phe Glu Ile Thr Val Pro Leu
            180                 185                 190
Ser Gln Gly Pro Lys Pro Val Thr Ile Ser Phe Ala Asn His Thr Ser
            195                 200                 205
Cys Arg Cys Met Ser Lys Leu Asp Val Tyr Arg Gln Val His Ser Ile
            210                 215                 220
Ile Arg Arg Ser Leu Pro Ala Thr Leu Pro Gln Cys Gln Ala Ala Asn
225                 230                 235                 240
Lys Thr Cys Pro Thr Asn Tyr Met Trp Asn Asn His Ile Cys Arg Cys
            245                 250                 255
Leu Ala Gln Glu Asp Phe Met Phe Ser Ser Asp Ala Gly Asp Asp Ser
            260                 265                 270
Thr Asp Gly Phe His Asp Ile Cys Gly Pro Asn Lys Glu Leu Asp Glu
            275                 280                 285
Glu Thr Cys Gln Cys Val Cys Arg Ala Gly Leu Arg Pro Ala Ser Cys
            290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
            325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
            355                 360                 365
Cys Leu Leu Lys Gly Lys Lys Phe His His Gln Thr Cys Ser Cys Tyr
370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
            405                 410                 415
Gln Met Ser

<210> SEQ ID NO 22
<211> LENGTH: 354
<212> TYPE: PRT
<213> ORGANISM: Homo sapiens

<400> SEQUENCE: 22

Met Tyr Arg Glu Trp Val Val Asn Val Phe Met Met Leu Tyr Val
1               5                   10                  15
Gln Leu Val Gln Gly Ser Ser Asn Glu His Gly Pro Val Lys Arg Ser
            20                  25                  30
Ser Gln Ser Thr Leu Glu Arg Ser Glu Gln Gln Ile Arg Ala Ala Ser
            35                  40                  45
Ser Leu Glu Glu Leu Leu Arg Ile Thr His Ser Glu Asp Trp Lys Leu
            50                  55                  60
Trp Arg Cys Arg Leu Arg Leu Lys Ser Phe Thr Ser Met Asp Ser Arg
65                  70                  75                  80
Ser Ala Ser His Arg Ser Thr Arg Phe Ala Ala Thr Phe Tyr Asp Ile
            85                  90                  95
Glu Thr Leu Lys Val Ile Asp Glu Glu Trp Gln Arg Thr Gln Cys Ser
            100                 105                 110
```

```
Pro Arg Glu Thr Cys Val Glu Val Ala Ser Glu Leu Gly Lys Ser Thr
        115                 120                 125
Asn Thr Phe Phe Lys Pro Pro Cys Val Asn Val Phe Arg Cys Gly Gly
    130                 135                 140
Cys Cys Asn Glu Glu Ser Leu Ile Cys Met Asn Thr Ser Thr Ser Tyr
145                 150                 155                 160
Ile Ser Lys Gln Leu Phe Glu Ile Ser Val Pro Leu Thr Ser Val Pro
                165                 170                 175
Glu Leu Val Pro Val Lys Val Ala Asn His Thr Gly Cys Lys Cys Leu
            180                 185                 190
Pro Thr Ala Pro Arg His Pro Tyr Ser Ile Ile Arg Arg Ser Ile Gln
        195                 200                 205
Ile Pro Glu Glu Asp Arg Cys Ser His Ser Lys Lys Leu Cys Pro Ile
    210                 215                 220
Asp Met Leu Trp Asp Ser Asn Lys Cys Lys Cys Val Leu Gln Glu Glu
225                 230                 235                 240
Asn Pro Leu Ala Gly Thr Glu Asp His Ser His Leu Gln Glu Pro Ala
                245                 250                 255
Leu Cys Gly Pro His Met Met Phe Asp Glu Asp Arg Cys Glu Cys Val
            260                 265                 270
Cys Lys Thr Pro Cys Pro Lys Asp Leu Ile Gln His Pro Lys Asn Cys
        275                 280                 285
Ser Cys Phe Glu Cys Lys Glu Ser Leu Glu Thr Cys Cys Gln Lys His
    290                 295                 300
Lys Leu Phe His Pro Asp Thr Cys Ser Cys Glu Asp Arg Cys Pro Phe
305                 310                 315                 320
His Thr Arg Pro Cys Ala Ser Gly Lys Thr Ala Cys Ala Lys His Cys
                325                 330                 335
Arg Phe Pro Lys Glu Lys Arg Ala Ala Gln Gly Pro His Ser Arg Lys
            340                 345                 350
Asn Pro

<210> SEQ ID NO 23
<211> LENGTH: 25
<212> TYPE: DNA
<213> ORGANISM: Artificial Sequence
<220> FEATURE:
<223> OTHER INFORMATION: Syntheric primer

<400> SEQUENCE: 23
tacaaagctt ttcgccacca tgcag                                               25

<210> SEQ ID NO 24
<211> LENGTH: 27
<212> TYPE: DNA
<213> ORGANISM: Artificial Sequence
<220> FEATURE:
<223> OTHER INFORMATION: Synthetic primer

<400> SEQUENCE: 24
tacaggatcc tcatgcacaa tgacctc                                             27
```